US008668914B2

(12) United States Patent  
Lephart et al.

(10) Patent No.: US 8,668,914 B2
(45) Date of Patent: *Mar. 11, 2014

(54) USE OF EQUOL FOR TREATING SKIN DISEASES

(75) Inventors: Edwin Douglas Lephart, Orem, UT (US); Trent D. Lund, St. Charles, IL (US); Kenneth David Reginald Setchell, Cincinnati, OH (US); Robert J. Handa, Phoenix, AZ (US)

(73) Assignees: Brigham Young University, Provo, UT (US); Colorado State University Research Foundation, Fort Collins, CO (US); Children's Hospital Medical Center, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/533,169

(22) Filed: Jul. 31, 2009

(65) Prior Publication Data

US 2010/0076071 A1 Mar. 25, 2010

Related U.S. Application Data

(63) Continuation-in-part of application No. 11/059,951, filed on Feb. 17, 2005, now abandoned, and a continuation of application No. 10/533,045, filed on Oct. 20, 2005, now abandoned, which is a continuation of application No. PCT/US03/03441, filed on Oct. 29, 2003, application No. 12/533,169, which is a continuation-in-part of application No. 10/625,989, filed on Jul. 24, 2003, and a continuation-in-part of application No. 12/167,813, filed on Jul. 3, 2008, now Pat. No. 7,960,432, which is a continuation of application No. 10/625,934, filed on Jul. 24, 2003, now Pat. No. 7,396,855.

(60) Provisional application No. 60/521,457, filed on Apr. 28, 2004, provisional application No. 60/422,469, filed on Oct. 29, 2002, provisional application No. 60/398,270, filed on Jul. 24, 2002.

(51) Int. Cl.
*A61K 8/02* (2006.01)
*A01N 43/16* (2006.01)

(52) U.S. Cl.
USPC .......................................... 424/401; 514/456

(58) Field of Classification Search
None
See application file for complete search history.

(56) References Cited

U.S. PATENT DOCUMENTS

| 4,390,559 | A | 6/1983 | Zilliken |
| 4,814,346 | A | 3/1989 | Albert et al. |
| 5,141,746 | A | 8/1992 | Fleury et al. |
| RE34,457 | E | 11/1993 | Okamoto et al. |
| 5,352,384 | A | 10/1994 | Shen |
| 5,424,331 | A | 6/1995 | Shlyankevich |
| 5,498,631 | A | 3/1996 | Gorbach et al. |
| 5,523,087 | A | 6/1996 | Shlyankevich |
| 5,726,034 | A | 3/1998 | Bryan et al. |
| 5,733,926 | A | 3/1998 | Gorbach |
| 5,804,234 | A | 9/1998 | Suh et al. |
| 5,830,887 | A | 11/1998 | Kelly |
| 5,849,798 | A | 12/1998 | Charpentier et al. |
| 5,855,892 | A | 1/1999 | Potter et al. |
| 5,942,539 | A | 8/1999 | Hughes, Jr. et al. |
| 5,952,374 | A | 9/1999 | Clarkson et al. |
| 5,958,946 | A | 9/1999 | Styczynski et al. |
| 5,990,291 | A | 11/1999 | Waggle et al. |
| 6,004,558 | A | 12/1999 | Thurn et al. |
| 6,020,471 | A | 2/2000 | Johns et al. |
| 6,054,636 | A | 4/2000 | Fader |
| 6,060,070 | A | 5/2000 | Gorbach |
| 6,083,526 | A | 7/2000 | Gorbach |
| 6,146,668 | A | 11/2000 | Kelly et al. |
| 6,159,959 | A | 12/2000 | Miller |
| 6,194,450 | B1 | 2/2001 | Charpentier et al. |
| 6,242,594 | B1 | 6/2001 | Kelly |
| 6,258,856 | B1 | 7/2001 | Chamberlain et al. |
| 6,326,366 | B1 | 12/2001 | Potter et al. |
| 6,340,703 | B1 | 1/2002 | Kelly |
| 6,375,994 | B1 | 4/2002 | Paul et al. |
| 6,455,032 | B1 | 9/2002 | Kelly et al. |
| 6,497,906 | B1 | 12/2002 | Kelly |

(Continued)

FOREIGN PATENT DOCUMENTS

| AU | 20006896 A4 | 5/2000 |
| CA | 2389560 | 11/2002 |

(Continued)

OTHER PUBLICATIONS

JP Equol Product, New Hair Loss DHT Treatment Breakthrough "Soy Equol," Nov. 1, 2004, p. 1 of 3; http://www.multiflora.co/uk/home%20to%20hair.htm.

(Continued)

*Primary Examiner* — Kyle Purdy
(74) *Attorney, Agent, or Firm* — Brinks Gilson & Lione

(57) ABSTRACT

Equol (7-hydroxy-3(4'hydroxyphenyl)-chroman), the major metabolite of the phytoestrogen daidzein, specifically binds and blocks the hormonal action of 5α-dihydrotestosterone (DHT) in vitro and in vivo. Equol can bind circulating free DHT and sequester it from the androgen receptor, thus altering growth and physiological hormone responses that are regulated by androgens. These data suggest a novel model to explain equol's biological properties. The significance of equol's ability to specifically bind and sequester DHT from the androgen receptor have important ramifications in health and disease and may indicate a broad and important usage for equol in the treatment and prevention of androgen-mediated pathologies of skin and hair. Thus, equol can specifically bind DHT and prevent DHT's biological actions in physiological and pathophysiological processes affecting skin and hair.

18 Claims, 22 Drawing Sheets

(56) References Cited

U.S. PATENT DOCUMENTS

| | | | |
|---|---|---|---|
| 6,509,043 B1 | 1/2003 | Hoie | |
| 6,518,301 B1 | 2/2003 | Barlaam et al. | |
| 6,544,566 B1 | 4/2003 | Waggle et al. | |
| 6,562,380 B1 | 5/2003 | Kelly | |
| 6,565,864 B2 | 5/2003 | Pillai et al. | |
| 6,599,536 B1 | 7/2003 | Kelly et al. | |
| 6,628,543 B2 | 9/2003 | Stobbs | |
| 6,638,543 B2 | 10/2003 | Kang et al. | |
| 6,642,212 B1 | 11/2003 | Kelly | |
| 6,716,424 B1 | 4/2004 | Uchiyama et al. | |
| 7,396,855 B2 | 7/2008 | Setchell et al. | |
| 2002/0001565 A1 | 1/2002 | Shapiro | |
| 2002/0019377 A1 | 2/2002 | Jenkins et al. | |
| 2002/0035074 A1 | 3/2002 | Kelly | |
| 2002/0160064 A1 | 10/2002 | Zulli et al. | |
| 2002/0198248 A1 | 12/2002 | Kelly et al. | |
| 2003/0018060 A1 | 1/2003 | Kelly et al. | |
| 2003/0027772 A1 | 2/2003 | Breton | |
| 2003/0059384 A1 | 3/2003 | Kelly et al. | |
| 2003/0078214 A1 | 4/2003 | Kelly | |
| 2003/0219499 A1 | 11/2003 | Kelly | |
| 2004/0147594 A1 | 7/2004 | Setchell et al. | |
| 2004/0235758 A1 | 11/2004 | Setchell et al. | |
| 2005/0036962 A1 | 2/2005 | Kelly | |
| 2005/0245492 A1 | 11/2005 | Lephart et al. | |
| 2006/0122262 A1 | 6/2006 | Lephart et al. | |
| 2007/0043108 A1 | 2/2007 | Lephart et al. | |
| 2010/0087519 A1 | 4/2010 | Lephart | |

FOREIGN PATENT DOCUMENTS

| | | |
|---|---|---|
| EP | 1961 309 A1 | 8/2008 |
| JP | H02-124883 | 5/1990 |
| WO | WO 93/23069 | 11/1993 |
| WO | WO 94/23716 | 10/1994 |
| WO | WO 96/10341 | 4/1996 |
| WO | WO 97/06273 | 2/1997 |
| WO | WO 98/08503 | 3/1998 |
| WO | WO 98/21946 | 5/1998 |
| WO | WO 98/25588 | 6/1998 |
| WO | WO 98/26784 | 6/1998 |
| WO | WO 98/48790 | 11/1998 |
| WO | WO 98/52546 | 11/1998 |
| WO | WO 98/56373 | 12/1998 |
| WO | WO99/07392 | 2/1999 |
| WO | WO 99/36050 | 7/1999 |
| WO | WO99/36067 | 7/1999 |
| WO | WO 99/49851 | 10/1999 |
| WO | WO 99/61028 | 12/1999 |
| WO | WO 00/13661 | 3/2000 |
| WO | WO 00/30663 | 6/2000 |
| WO | WO 00/41491 | 7/2000 |
| WO | WO 00/49009 | 8/2000 |
| WO | WO 00/62765 | 10/2000 |
| WO | WO 00/62774 | 10/2000 |
| WO | WO 02/03976 | 1/2002 |
| WO | WO 02/03977 | 1/2002 |
| WO | WO 02/03992 | 1/2002 |
| WO | WO 02/11675 | 2/2002 |
| WO | WO 02/053108 | 7/2002 |
| WO | WO 02/062367 | 8/2002 |
| WO | WO02/067988 | 9/2002 |
| WO | WO 02/067988 | 9/2002 |
| WO | WO 02/087517 | 11/2002 |
| WO | WO 02/089757 | 11/2002 |
| WO | WO 2004/009035 | 1/2004 |
| WO | WO 2004/022023 | 3/2004 |
| WO | WO 2004/026274 | 4/2004 |
| WO | WO 2004/039327 | 5/2004 |

OTHER PUBLICATIONS

Literature documents cited in U.S. Appl. No. 10/625,989 filed Jul. 24, 2003, entitled "Composition and Products Containing R-equol, and Methods for their Making" by Setchell et al.

Literature documents cited in U.S. Appl. No. 10/625,934, filed Jul. 24, 2003, entitled "Composition and Products Containing S-equol, and Methods for their Making" by Setchell et al.

Literature documents cited in U.S. Appl. No. 10/533,045, filed Oct. 20, 2005, entitled "Use of Equol for Treating Androgen Mediated Diseases," by Lephart et al.

Literature documents cited in U.S. Appl. No. 11/059,951, filed Feb. 17, 2005, entitled "Use of Equol for Treating Skin Diseases," by Lephart et al.

Luk K.-C. et al., "Isolation and Identification of 'Diazepam-like' Compounds from Bovine Urine," *Journal of Natural Products*, 46(6):852-861 (1983).

Supplemental European Search Report issued Jul. 1, 2008 by the European Patent Office in corresponding European application No. 05723182.1; received from the European associate on Jul. 7, 2008.

Supplementary European Search Report, Application No. EP 03 77 7994, mailed Jun. 6, 2007, 6 pages.

Alda J. et al., "Purification and Chemical Characterization of a Potent Inhibitor of the Na-k-Cl Cotransport System in Rat Urine," *Biochemical and Biophysical Research Communications*, 221:279-285 (1996).

Aldercreutz H. et al., "Excretion of the Lignans Enterolactone and Enterodiol and of Equol in Omnivorous and Vegetarian Postmenopausal Women and in Women with Breast Cancer," *The Lancet*, pp. 1295-1299 (Dec. 11, 1982).

Aldercreutz H. et al., "Urinary Excretion of Lignans and Isoflavonoid Phytoestrogens in Japanese Men and Women Consuming a Traditional Japanese Diet," *Am. J. Clin. Nutr.*, 54:1093-1100 (1991).

Aldercreutz H. et al., "Dietary Phytoestrogens and Cancer: In Vitro and In Vivo Studies," *J Steroid Biochem Mol Biol.*, 41(3-8):331-7 (1992).

Aldercreutz H. et al., "Dietary phyto-estrogens and the Menopause in Japan," *Lancet*, 339(8803):1233 (1992).

Aldercreutz H. et al., "Effect of Dietary Components, Including Lignans and Phytoestrogens, an Enterohepatic Circulation and Liver Metabolism of Estrogens and on Sex Hormone Binding Globulin (SHBG)," *J Steroid Biochem*, 27(4-6):1135-44 (1987).

Aldercreutz H., et al., "Diet and Breast Cancer," *Acta Oncol*, 31(2):175-81 (1992).

Aldercreutz H. et al., "Determination of Urinary Lignans and Phytoestrogen Metabolites, Potential Antiestrogen and Anticarcinogens in Urine of Women on Various Habitual Diets," *J. Steroid Biochem*, 25:791-797 (1996).

Akaza H. et al., "Is Daidzein Non-metabolizer a High Risk for Prostate Cancer? A Case-Controlled Study of Serum Soybean Isoflavone Concentration," *Jpn J Clin Oncol*, 32(8):296-300 (2002).

Albert A. et al., "Efficacy and Safety of a Phytoestrogen Preparation Derived from Glycine max (L.) Merr in Climacteric Symptomatology: A multicentric, Open, Prospective and Non-randomized Trial," *Phytomedicine*, 9(2):85-92 (2002).

Alvira E. et al., "Molecular Modeling Study for Chiral Separation of Equol Enantiomers by β-cyclodextrin," *Chemical Physics* 240, pp. 101-108, Elsevier Science B.V. (1999).

Anderson Edith L. et al., "The Identification of Equol as 7-Hydroxy-3-(4'-Hydroxyphenyl) Chroman, and the Synthesis of Racemic Equol Methyl Ether," *J. Biol. Chem.*, 127:649-56 (1939).

Atkinson C. et al., "In Vitro Incubation of Human Feces with Daidzein and Antibiotics Suggests Interindividual Differences in the Bacteria Responsible for Equol Production," *Amer. Society for Nutritional Sciences*, 134:596-599 (Mar. 2004).

Axelson M. et al., "Soya—A Dietary Source of the Non-steroidal Estrogen Equol in Man and Animals," *J Endocrinol*, 102(1):49-56 (1984).

Axelson M. et al., "The Identification of the Weak Oestrogen Equal [7-hydroxy-3-4'-hydroxyphenyl)chroman] in Human Urine," *J. Biochem*, 201:353-357 (1982).

Atsutane O. et al., "A Combination of Dietary Fructooligosaccharides and Isoflavone Conjugates Increases Femoral Bone Mineral Density and Equol production in Ovarioctomized Mice," *American Society for Nutritional Sciences*, pp. 2048-2054 (2002).

Bowey E. et al., "Metabolism of Isoflavones and Lignans by the Out Micronora: a Study in Germ-Free and Human Flora Associated Rats," *Food Chem Toxicol*, 41(5):631-6 (May 2003).

(56) References Cited

OTHER PUBLICATIONS

Brown N.M. et al., "Animal Modes Impacted by Phytoestrogens in Commercial Chow: Implications for Pathways Influenced by Hormones," *Laboratory Investigation*, 81(5) P2S:735•747 (May 2001).
Cassidy A., "Physiological Effects of Phyto-estrogens in Relation to Cancer and Other Human Health Risks," *Proc: Nutr Soc.*, 55(1B):399-417 (1996).
Cassidy A. et al., "Biological Effects of Isoflavones in Young Women: Importance of the Chemical Composition of Soybean Products," *Br J Nutr*, 74(4):587-601 (1995).
Chang Y.C., and Nair M.G., "Metabolism of Daidzein and Genistein by Intestinal Bacteria," *J. of Natural Products*, 58(12):1892-1896 (1995).
Chiralcel® OD, Instruction Sheet, Daicel Chemical Industries, Ltd., Japan (May 1, 1995).
Chiralcel® OD, Instruction Sheet, Daicel Chemical Industries, Ltd., Exton PA, (Dec. 6, 1994).
Duncan A. M. et al., "Premenopausal Equol Excretors Show Plasma Hormone Profiles Associated with Lowered Risk of Breast Cancer," *Cancer Epidemiol, Biomarkers Prev* 9:581-596 (Jun. 2000).
Gambacciani M. et al., "Effects of Low-Dose, Continuous Combined Estradiol and Noretisterone Acetate on Menopausal Quality of Life in Early Postmenopausal Women," *Maturitas*, 44(2):157-63 (2003).
Garreau B. et al., "Phytoestrogens: New Ligands for Rat and Human Alpha-Fetoprotein," *Biochem Biophys Act*, 1094(3):339-45 (1991).
Girt A.K. and L.J. Lu, "Genetic Damage and the Inhibition of 7,12-Dimethylbenz[a]anthracene-induced Genetic Damage by the Phytoestrogens, Genistein and Daidzein, in Female ICR mice," *Cancer Lett*, 95(1-2):125-33 (1995).
Goldin B.R. and S.L. Gorbach, "Phytoestrogens: Possible Role in Preventing Human Disease," *Nutrition*, 12(3): 216-7 (1996).
Hartley D.E. et al., "The Soya Isoflavone Content of Rat Diet Can Increase Anxiety and Stress Hormone Release in the Male Rat," *Psychopharmacology (Berl)*, 167(1):46-53 (2003).
Havsteen B., "Flavonoids, A Class of Natural Products of High Pharmacological Potency," *Biochem Pharmacol*, 32(7):1141-8 (1983).
Hedlund T.E. et al., "Soy Isoflavonoid Equol Modulates the Growth of Benign and Malignant Prostatic Epithelial Cells In Vitro," *Prostate*, 54(I):68-78 (2003).
Hwang J. et al., "The Phytoestrogen Equol Increases Nitric Oxide Availability by Inhibiting Superoxide Production: An Antioxidant Mechanism for Cell-Mediated LDL Modification," *Free Radical Biology & Medicine*, 34(10):1271-1282 (2003).
Ingram D. et al., "Case-control Study of Phyto-oestrogens and Breast Cancer," *The Lancet*, 350:990-994 (Oct. 4, 1997).
Joannou G.E. et al., A Urinary Profile Study of Dietary Phytoestrogens. The Identification and Mode of Metabolism of New Isoflavonoids, J. Steroid Biochem. Molec. Biol., 54(3/4):167-184 (1995).
Kao P.C. and K. P'Eng F, How to Reduce the Risk Factors of Osteoporosis in Asia Zhonghua Yi Xue Za Zhi (Taipei), 55(3): 209-13 (1995).
Kaziro R. et al., "The Oestrogenicity of Equol in Sheep," *J Endocrinol*, 103(3):395-9 (1984).
Kinjo J., "Phytoestrogens," *Japanese Journal of Clinical Medicine*, 58(12):2434-8 (Dec. 2000).
Kohli J.C. et al., "Specific Separation of Equol from Estrogens by Thin-Layer Chromatography," *Journal of Chromatography*, Elsevier Scientific Publ. Co., Amsterdam, 129:473-474 (1976).
Kostelac D. et al., "Phytoestrogens Modulate Binding Response of Estrogen Receptors Alpha and Beta to the Estrogen Response Element," *J Agric 7632-5 Food Chem*, 51(26):7632.5 (2003).
Kurosawa K., et al., "The Absolute Configurations of the Annual Metabolite, Equol, Three Naturally Occurring Isoflavans, and One Natural Isoflavanquinone," *Chemical Communications*, 1265-1264 (1968).
Lamartiniere C.A., et al., "Daidzein: Bioavailability, Potential for Reproductive Toxicity, and Breast Cancer Chemo Prevention in Female Rats," *Toxicol Sci*, 65(2):228.38 (2002).

Lamberton John A. et al., "Catalytic Hydrogenation of Isoflavones. The Preparation of (±)-Equal and Related Isoflavans," *Aust. J. Chem.*, pp. 455-457 (1978).
Landstrom M., et al., "Inhibitory Effects of Soy and Rye Diets on the Development of Dunning R3327 Prostate Adenocarcinoma in Rats," *Prostate*, 36(3):151-61 (1998).
LC Laboratories and US Biological product list.
Lephart E.D., "Brain 5alpha-Reductase: Cellular, Enzymatic, and Molecular Perspectives and Implications for Biological Function," *Molecular and Cellular Neurosciences*, (4):e473-484 (1993).
Lephart E.D. et al., "Brain Androgen and Progesterone Metabolizing Enzymes: Biosynthesis, Distribution and Function," *Brain Res Brain Res Rev*, 37(1-3):25-37 (2001).
Lephart E.D. et al., "Neurobehavioral Effects of Dietary Soy Phytoestrogens," *Neurotoxicol Teratol*, 24(1):5-16 (2002).
Lephart E.D., "Estrogens and Phytoestrogens: Brain Plasticity of Sexually Dimorphic Brain Volumes," *J. Steroid Biochem Mot Biol.*, 85(2-5):299-309 (2003).
Lephart E.D., "Dietary Soy Phytoestrogen Effects on Brain Structure and Aromatase in Long-Evans Rats," *Neuro Report*, 12(16):3451-3455 (Nov. 2001).
Lephart E.D., "Behavioral Effects of Endocrine-Disrupting Substances: Phytoestrogens," *IIAR J*, 45(4):443-54 (2004).
Lephart E.D., "Dietary Isofavones Alter Regulatory Behaviors, Metabolic Hormones and Neuroendocrine Function in Long-Evans Male Rats," *Nutrition & Metabolism*, 1(16):1-14 (2004).
Lephart E. D., "Equol Reduces Prostate Size and Tail Skin Temperature in Male Rats," *Experimental Biology*, San Diego, CA, Abstract # 280.9 (Apr. 2005).
Lephart E. D., "Antiaging Effects of Equol: A Unique Antiandrogenic Isoflavone Metabolite and its Influence in Stimulating Collagen Deposition in Human Dermal Monolayer Fibroblasts," *American Academy of Dermatology*, 63rd Annual Meeting, New Orleans, LA, 52(3):1005 (Feb. 18-22, 2005).
Lephart E.D., "Equol: A Unique Anti-Androgenic Isofavone Metabolite Stimulates Collagen (I & III), Elastin and Human Fibroblast Proliferation and Inhibits MMPs and Elastase in 3-D Cultures via FACS Analysis," (Sep. 28, 2005).
Lu L.J. et al., "Effects of Soya Consumption for One Month on Steroid Hormones in Premenopausal Women: Implications for Breast Cancer Risk Reduction," *Cancer Epidemiol Biomarkers Prev*, 5(1): 63-70 (1996).
Lund T.D. et al., "Equol is a Novel Anti-Androgen that Inhibits Prostate Growth and Hormone Feedback," *Biol. Reprod.*, 70(4) 118895, E-Pub. Dec. 17, 2003; (Apr. 2004).
Lund T. D., "The Phytoestrogen Metabolite Equol Acts as a Novel Anti-Androgen to Inhibit Prostate Growth and Hormone Feedback," Abstract Published for Endo 2003 Program; Endocrine Society 85*th* Annual (2003); Abstract.
Lund T.D., "Altered Sexually Dimorphic Nucleus of the Preoptic Area (SDN•POA) Volume in Adult Long. Evans Rats by Dietary Soy Phytoestrogens," *Brain Research*, vol. 914, Issues 1-2; Abstract.
Lyn-Cook B.D., et al., Methylation Profile and Amplification of Proto-Oncogenes in Rat Pancreas Induced with Phytoestrogens, *Proc Soc Exp Biol. Med*, 208(1):116-9 (1995).
Magee P. et al., "Equol: A Comparison of the Effects of the Racemic Compound with That of the Purified S-Enantiomer on the Growth, Invasion, and DNA Integrity of Breast and Prostate Cells In Vitro," *Nutrition and Cancer*, 54(2):232-242 (2006).
Martin M.E., et al., "Interactions Between Phytoestrogens and Human Sex Steroid Binding Protein," *Life Sci.*, 58(5):429-36 (1996).
Marrian G.F. and Haslewood, G.D., "CXLV. Equol, a New Inactive Phenol Isolated from the Ketohydroxy-Oestrin Fraction of Mares' Urine," *University College, London, Department of Physiology and Biochemistry*, 1227-1232 (1932).
Mitchell J.H. et al., "Effects of Phytoestrogens on Growth and DNA Integrity in Human Prostate Tumor Cell Lines: PC-3 and LNCaP," *Nutr Cancer*, 38(2):223-8 (2000).
Morito K. et al., "Interaction of Phytoestrogens with Estrogen Receptors Alpha and Beta," *Biol Pharm Bull*, 24(4):351-6 (2001).
Murkies A. L. et al., "Dietary Flour Supplementation Decreases Post-Menopausal Hot Flushes: Effect of Soy and Wheat," *Maturitas*, 21(3):189-95 (1995).

(56) References Cited

OTHER PUBLICATIONS

Muthyala R.S. et al., "Equol, a Natural Estrogenic Metabolite from Soy Isoflavones: Convenient Preparation and Resolution of R- and S-equols and their Differing Binding and Biological Activity through Estrogen Receptors Alpha and Beta," *Bioorganic & Medicinal Chemistry*, 12:1559-1567 (2004).

Naim M. et al., "Antioxidative and Antihemolytic Activities of Soybean Isoflavones," *J Agric Food Chem*, 24(6):1174-7 (1976).

Ogawara H., "A Specific Inhibitor for Tyronsine Protein Kinase from *Pseudomonas*," *The Journal of Antibiotics*, 39(4):606-608 (Apr. 1936).

Ohta A. et al., "A Combination of Dietary Frictooligosaccharides and Isoflavone Conjugates Increases Femoral Bone Mineral Density and Equol Production in Ovariectomized Mice," *American Society for Nutritional Sciences*, pp. 2048-2054 (2002).

Pelissero et al., *J. Steroid Biochem. Molec. Biol.*, 38(3):293-299 (1991).

Rafii F. et al, "Variations in Metabolism of the Soy Isoflavonid Daidzen by Human Intestinal Microfloras from Different Individuals," *Arch Microbiol.*, 180(1):11-6 (2003).

Rimbach G. et al., "Antioxidant and Free Radical Scavenging Activity of Isoflavone Metabolites," *Xenobiotica*, 33(9):913-25 (2003).

Rowland I.R. et al., "Interindividual Variation in Metabolism of Soy Isoflavones and Lignans: Influence of Habitual Diet on Equol Production by the Gut Microflora," *Nutrition and Cancer*, 36(1):27-32 (2000).

Sathyamoorthy N. et al, "Differential Effects of Dietary Phytoestrogens Daidzein and Equol on Human Breast Cancer MCF-7 Cells," *European Journal of Cancer*, 33(14):2384-2389 (1997).

Sharma O.P. et al., "Soy of Dietary Source Plays a Preventive Role Against the Pathogenesis of Prostatitis in Rats," *J Steroid Biochem Mol Biol*, 43(6):557-64 (1992).

Sharpe R.M. and N.E. Skakkebaek, "Are Oestrogens Involved in Falling Sperm Counts and Disorders of the Male Reproductive Tract?" *Lancet*, 341(8857):1392-5 (1993).

Shelnutt S.R. et al., "Pharmacokinetics of the Glucuronide and Sulfate Conjugates of Genistein and Daidzein in Men and Women After Consumption of a Soy Beverage," *Am J Clin Nutr*, 76:588-594 (2002).

Sigma-Aldrich webpage, (±)-Equol Product No. 45405 (Oct. 23, 2003).

Sigma-Aldrich webpage, Equol, Product No. 45405 (Jul. 10, 2003).

Spinozzi F. et al., "The Natural Tyrosine Kinase Inhibitor Genistein Produces Cell Cycle Arrest and Apoptosis in Jurkat T-leukemia Cells," *Leuk Res*, 18(6):431-9 (1994).

Setchell K.D. et al., "S-Equol, A Potent Ligand for Estrogen Receptor β, is the Exclusive Enantiomeric form of the Soy Isoflavone Metabolite Produced by Human Intestinal Bacterial Flora," *Am. J. Clin. Nutr.*, 81:1072-1079 (2005).

Setchell D.R. and Cole, S.J., "Method of Defining Equol-Producer Status and Its Frequency among Vegetarians," *J. of Nutrition*, 2188-2192 (2006).

Setchell K.D. et al., "The Clinical Importance of the Metabolite Equol—A Clue to the Effectiveness of Soy and Its Isoflavones," *J. of Nutrition*, 132:3577-3584 (2002).

Setchell K.D. et al., "Equol—Origins, Actions, and Clinical Relevance of this Specific Soy Isoflavone Metabolite," *Fifth International Symposium on the Role of Soy in Preventing and Treating Chronic Disease*, Oral Presentation Abstracts, J. of Nutrition, 134:1234S-1247S (2004).

Setchell K. D.R. et al., "Bioavailability of Pure Isoflavones in Healthy Humans and Analysis of Commercial Soy Isoflavone Supplements," *American Society for Nutritional Sciences*, pp. 1362S•1375S (2001).

Setchell K.D.R. et al., "Evidence for Lack of Absorption of Soy Isoflavone Glycosides in Humans, Supporting the Crucial Role of Intestinal Metabolism for Bioavailability," *Am J Clin Nutri*, 76:447-453 (2002).

Setchell K.D.R. et al., "Nonsteroidal Estrogens of Dietary Origin: Possible Roles in Hormone-Dependent Disease," *The American Journal of Clinical Nutrition*, 40:569•578 (Sep. 1984).

Setchell K.D.R. et al., "Dietary Phytoestrogens and Their Effect on Bone: Evidence from In Vitro and In Vivo, Human Observational and Dietary Intervention Studies," *Am J Clin Nutr*, 78 (suppl): 593S-609S (2003).

Setchell K.D.R. et al., "Bioavailability, Disposition, and Dose-Response Effects of Soy Isoflavones When Consumed by Healthy Women at Physiologically Typical Dietary Intakes," *American Society for Nutritional Sciences*, pp. 1027-1035 (2003).

Setchell K.D.R. et al., "The Clinical Importance of the Metabolite Equol—A Clue to the Effectiveness of Soy and Its Isoflavones," *American Society for Nutritional Sciences*, pp. 3577-3584 (2002).

Setchell K.D.R. et al., "Phytoestrogens: The Biochemistry, Physiology, and Implications for Human Health of Soy Isoflavones," *Am J. Clin Nutri*, pp. 1333S-1346S (1998).

Setchell K. D. R., "Equol—Its Unique Property as a Selective Estrogen Receptor Modulator (SERM) and a Selective Androgen Modulator (SAM)," *Soy & Health*, Brugge, Belgium (Oct. 7-8, 2004).

The Merck Index, Twelfth Edition, p. 3677, 2 pages (1996).

Thompson M.A. et al., "Characterization of the Estrogenic Properties of a Nonsteroidal Estrogen, Equol, Extracted from Urine of Pregnant Macaques," *Biol Reprod.*, 31:705-713 (1984).

Verbit L. and Clark-Lewis J.W., "Optically Active Aromatic Chromophores—VIII Studies in the Isoflavonoid and Rotenoid Serices," *Tetrahedron*, 24:5519-5527 (1968).

Wang X.L. et al., "Enantioselective Synthesis of S-Equol from Dihydrodaidzein by a Newly Isolated Anaerobic Human Intestinal Bacterium," *Applied and Environmental Microbiology*, 71(1): 214-219 (2005).

Weber K. S., "Dietary Soy-Phytoestrogens Decrease Testosterone Levels and Prostate Weight Without Altering LH, Prostate 5α-reductase or Testicular Steroidogenic Acute Regulatory Peptide Levels in Adult Male Sprague-Dawley Rats," *Journal of Endocrinology*, 170:591-599 (2001).

Wahala Kristine et al., "Synthesis of the [$^2$H] -Labeled Urinary Lignans, Enterolactone and Enterodiol, and the Phytoestrogen Daidzein and its Metabolites Equol and O-Demethyl-angolensin," *J. Chem. Soc. Perkin Trans I*, pp. 95-98 (1986).

Whitehead M., "Treatments for Menopausal and Post-menopausal Problems: Present and Future," *Baillieres Clin Obstet Gynaecol*, 10(3):515-30 (1996).

Widyarini S. et al., "Isoflavonoid Compounds from Red Clover (*Trifolium pretense*) Protect from Inflammation and Immune Suppression Induced by UV Radiation," *Photochem Photobiol*, 74(3):465-70 (2001).

U.S. Appl. No. 11/059,951, filed Feb. 17, 2005, Lephart, et al.

U.S. Appl. No. 10/625,989, filed Jul. 24, 2003, Setchell, et al.

U.S. Appl. No. 10/533,045, filed Oct. 20, 2005, Lephart et al.

U.S. Appl. No. 12/167,813, filed Jul. 3, 2008, Setchell et al.

"Isoflavonoid Compounds from Red Clover (*Trifolium pretense*) Protect from Inflammation and Immune Suppression Induced by UV Radiation," *Photochemistry and Photobiology*, 74(3):465-470 (2001).

"Phytoestrogens," *Japanese J. of Clinical Medicine*, 58(12):2434-2438 (2000).

European Search Report in European Application No. EP10194495, dated Feb. 22, 2011.

Examiner's Report in Canadian Application No. 2,564,399, dated Mar. 2, 2011.

Supplementary European Search Report in EP Application No. 06813546.6-1216/2063898 dated Jan. 17, 2012.

Third Party Obseniations filed in European Patent Application No. 10194495.7, dated Aug. 10, 2011; provided with the letter from the European associate dated Aug. 22, 2011.

Gimenez et al., J. Hypertens., 15:1303-8 (1997).

Lou et al., J. Med. Food, 2(3-4):257-60 (1999).

Chin-Dusting et al., Br. J. Pharmacol., 133:596-605 (2001).

(56) References Cited

OTHER PUBLICATIONS

DeVito et al., Peptides, 31:1412-1419 (2010).
International Search Report and Written Opinion in PCT Application No. PCT/US2010/043017 dated Feb. 3, 2012.
Evans, et al., "Inhibition of 5α-reductase in genital skin fibroblasts and prostate tissue by dietary lignans and isoflavonoids," *J. Endocrinol*, 147(2):295-302 (1995).
Mitchell, et al., "Effects of Phytoestrogens on Growth and DNA Integrity in Human Prostate Tumor Cell Lines: PC-3 and LNCaP," *Nutr. Cancer*, 38(2):223-228 (2000).
US 6,448,237, 09/2002, Kelly (withdrawn)

S-equol          R-equol

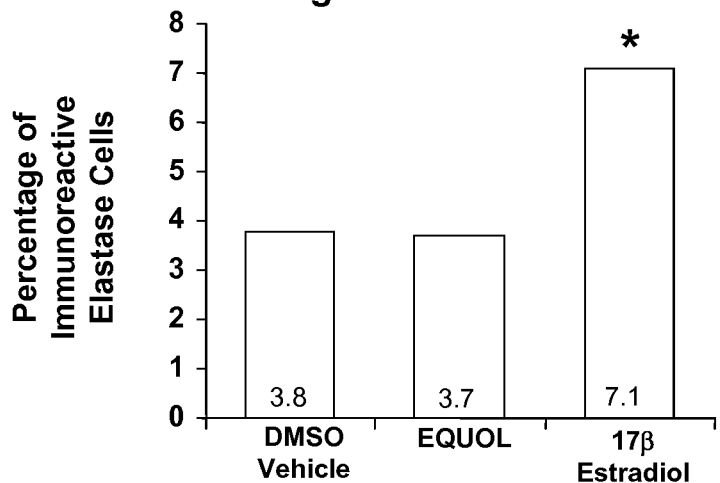
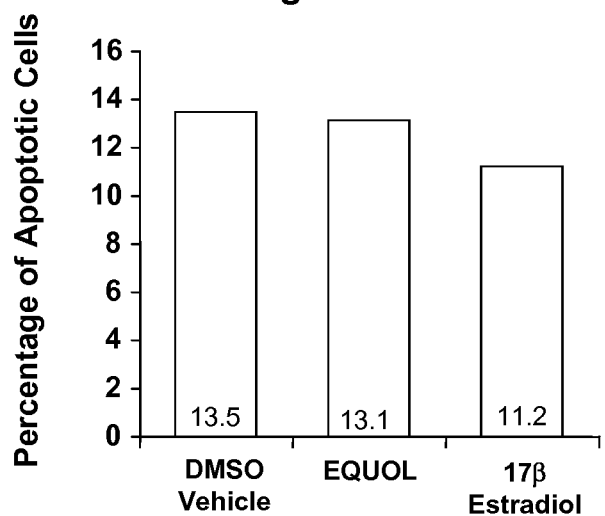
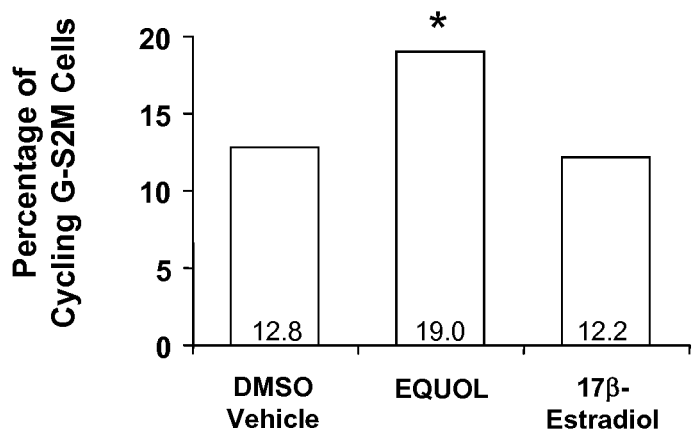

Ocular Irritection Model

Dermal Irritection Model

USE OF EQUOL FOR TREATING SKIN DISEASES

RELATED APPLICATIONS

The present patent document is a continuation-in-part of application Ser. No. 11/059,951, filed Feb. 17, 2005, which claims the benefit of the filing date under 35 U.S.C. §119(e) of Provisional U.S. Patent Application Ser. No. 60/521,457, filed Apr. 28, 2004. Also, the present patent document is a continuation-in-part of application Ser. No. 10/533,045, filed Oct. 20, 2005, which is a continuation of PCT Application Ser. No. US2003/034441, filed Oct. 29, 2003, designating the United States and published in English which claims the benefit of the filing date under 35 U.S.C. §119(e) of Provisional U.S. Patent Application Ser. No. 60/422,469, filed Oct. 29, 2002. Also, the present patent document is a continuation-in-part of application Ser. No. 10/625,989, filed Jul. 24, 2003, which claims the benefit of the filing date under 35 U.S.C. §119(e) of Provisional U.S. Patent Application Ser. No. 60/398,270, filed Jul. 24, 2002, and of application Ser. No. 12/167,813, filed Jul. 3, 2008, which is a continuation of application Ser. No. 10/625,934, filed Jul. 24, 2003 (now U.S. Pat. No. 7,396,855), which claims the benefit of the filing date under 35 U.S.C. §119(e) of Provisional U.S. Patent Application Ser. No. 60/398,270, filed Jul. 24, 2002. All of the foregoing applications are hereby incorporated by reference in their entirety.

FEDERALLY SPONSORED RESEARCH OR DEVELOPMENT

This invention was made with Government support under Grant # NS39951, awarded by the National Institute of Health (NIH), and Grants # NRI 2002-00798 and # NR12004-01811 awarded by the U.S. Dept. of Agriculture (USDA).

The Government has certain rights in this invention.

BACKGROUND

This invention relates equol and its mechanism of action and use as a therapeutic compound for treating and preventing physiological and pathophysiological conditions mediated by androgens.

In recent years phytoestrogens have received increased investigative attention due to their potential protective effects against age-related diseases (e.g. cardiovascular disease and osteoporosis) and hormone-dependent cancers (i.e., breast and prostate cancer). There are three main classifications of phytoestrogens: 1) isoflavones (derived principally from soybeans), 2) lignans (found in flaxseed in large quantities) and 3) coumestans (derived from sprouting plants like alfalfa). Of these three main classifications, human consumption of isoflavones has the largest impact due to its availability and variety in food products containing soy. Of the isoflavones, genistein and daidzein are thought to exert the most potent estrogenic hormone activity and thus most attention has been directed toward these molecules (Knight et al, *Obstet Gyneco*, 187:897-904, (1996); Setchell, K D R. *Am J Clin Nutr*, 129: 1333 S-1346S (1998); Kurzer et al, *Annu Rev Nutr*, 17:353-381 (1997)). However, these isoflavone molecules do not exist at high levels in their biologically active form in soy foods, but rather are at high abundance in a precursor form. For example, genistin, the precursor of genistein, is the glycosidic form that contains a carbohydrate portion of the molecule. Additionally, malonylglucoside and acetylglucoside forms also are found. These conjugates are metabolized in the gastrointestinal (GI) tract by intestinal bacteria, which hydrolyze the carbohydrate moiety to the biologically active phytoestrogen, genistein. The same metabolic step occurs for the aglycone daidzein, which is converted from the glycosidic form daidzin. Diadzein is then further metabolized to equol in an "equol-producing" mammal, which is then found in the plasma of an equol-producing individual. Equol is not normally present in the urine of most healthy human adults unless soy is consumed. The formation of equol in vivo is exclusively dependent on intestinal microflora as evidenced from the finding that germ-free and phytoestrogen-free fed animals do not excrete equol when fed soy, and that equol is not found in the plasma and urine of human newborn or 4-month old infants fed exclusively soy foods from birth due to the fact that the intestinal flora has not yet developed in neonates. (See Setchell et al, *The Lancet*, 1997; 350:23-27).

The phenolic ring structures of isoflavones enable these compounds to bind estrogen receptors (ER) and mimic estrogen. Although genistein and daidzein bind to ER, it is with a lower affinity when compared to estradiol, and with a greater affinity for ERβ than to ERα. Thus isoflavones, like genistein and the metabolite S-equol, act like natural selective estrogen receptor modulators (SERMs) at various tissue sites throughout the body. In some tissues, there is evidence that phytoestrogens act as estrogen agonists, whereas in others, they display antagonistic characteristics comparable to that of tamoxifen or raloxifene where SERM activity appears to be sex-hormone- and gender-dependent.

While the bulk of the scientific literature has focused on the natural isoflavones in soy or clover, little has been reported on the actions or effects of their intestinally derived metabolites. Equol (7-hydroxy-3(4'hydroxyphenyl)-chroman) represents the major metabolite of the phytoestrogen daidzin, one of the main isoflavones found abundantly in soybeans and soyfoods. Equol, however, is not a phytoestrogen, because it is not a natural constituent of plants. Equol does not occur naturally in any plant-based products. Rather, it is a non-steroidal isoflavone that is exclusively a product of intestinal bacterial metabolism, however, only about 30-40% of humans have the microflora necessary to convert soy isoflavones to equol.

Previous research with equol has identified that equol possesses some weak estrogenic properties, binds sex hormone binding globulin and α-fetoprotein, and has antioxidant activity. The S-enantiomer of equol (S-)-equol) is the exclusive equol form found in the urine and plasma of "equol-producing" mammals consuming soy, and is the only equol enantiomer made by human intestinal bacteria. The R- and S-enantiomers conformationally differ, which subsequently influences their biological activity. For example, only the S-enantiomer of equol binds ER subtypes with sufficient affinity to be relevant to usual circulating equol levels reported in humans.

The prostate gland depends on androgen hormone action for its development and growth, and the development of human benign prostatic hyperplasia (BPH) clearly requires a combination of testicular androgens during the aging process. However, testosterone is not the major androgen responsible for growth of the prostate. The principal prostatic androgen is 5α-dihydrotestosterone (5α-DHT), as evidenced by current treatments of prostatic cancer, which are directed toward reducing 5α-DHT with 5α-reductase inhibitors. Although not elevated in human BPH, 5α-DHT levels in the prostate remain at a constant with aging, despite a decrease in the plasma testosterone concentration. Testosterone is converted to 5α-DHT by 5α-reductase in prostatic stromal and basal cells. 5α-DHT is primarily responsible for prostate development and the pathogenesis of BPH. Inhibitors of 5α-reductase reduce prostate size by 20% to 30%. This reduction in glandular tissue is achieved by the induction of apoptosis, which is histologically manifested by ductal atrophy. 5α-reductase occurs as 2 isoforms, type 1 and type 2, with the prostate expressing predominantly the type-2 isoform, and the liver and skin expressing primarily the type-1 isoform. Patients have been identified with deficiencies in the type-2 5α-reductase, but not type 1. Gene-targeted knockout mice with the type-2 5α-reductase null-mutation demonstrate a phenotype similar to that seen in men with 5α-reductase deficiency. Type-15α-reductase knockout male mice are phenotypically normal with respect to reproductive function. Enzymatic activity for 5α-reductase or immunohistochemical detection has been noted in other genitourinary tissues, such as the epididymis, testes, gubernaculum, and corporal cavernosal tissue.

Quantitatively, women secrete greater amounts of androgen than that of estrogen due to the greater adrenal cortical responsiveness by gender. The major circulating steroids generally classified as androgens include dehydroepiandrosterone sulphate (DHEAS), dehydroepiandrosterone (DHEA) (originating from the adrenal cortex), androstenedione (A), testosterone (T), and 5α-DHT in descending order of serum concentration, though only the latter two bind the androgen receptor to a significant degree. The other three steroids are better considered as pro-androgens. 5α-DHT is primarily a peripheral product of testosterone metabolism. Testosterone circulates both in its free form, and bound to protein including albumin and sex steroid hormone-binding globulin (SHBG), the levels of which are an important determinant of free testosterone concentration. The postmenopausal ovary is an androgen-secreting organ and the levels of testosterone are not directly influenced by the menopausal transition or the occurrence of menopause.

The work of some research has focused on the development of steroidal compounds for the treatment of androgen dependent diseases such as: hirsutism, androgenic alopecia, benign prostatic hyperplasia (BPH) and prostate cancer. DHT has been implicated as a causative factor in the progression of these diseases, largely through the clinical evaluation of males who are genetically deficient of steroid 5α-reductase enzyme. As a result of such studies, the inhibition of this enzyme has become a pharmacological strategy for the design and synthesis of new antiandrogenic drugs. However, it is unclear whether inhibition of 5α-reductase will have a deleterious impact on the system, as evidenced by contraindications arising from reported side effects of conventional treatments using 5α-reducatse inhibitors, such as decreased libido, erectile dysfunction and ejaculatory disorders. The development of different strategies that target the inhibition of DHT effects would be a major advance in the therapy of androgen-mediated conditions.

Despite the recent gains in understanding the pharmacology of equol as it pertains to estrogen actions, our research showing potent antiandrogen effects of equol is unique and novel and opens new approaches to preventing or treating androgen-related conditions. Binding or sequestering 5α-DHT would provide a means for inhibiting its effect on 5α-DHT-sensitive tissues. There is no known ligand that is specific for 5α-DHT, but such an agent would have distinct advantages over non-discriminatory compounds that target the androgen receptor directly or the enzymes involved in androgen synthesis.

SUMMARY

The present invention relates to a method of co-mediating androgen hormone action and estrogen hormone action, that ameliorate one or more physiological and pathophysiological conditions/disorders of the skin in human and non-human species, by administering an enantiomeric equol comprising S-equol, in an amount sufficient to bind free 5α-DHT, thereby inhibiting its binding with androgen receptors, and to bind estrogen receptor subtypes.

The present invention also relates to a method of mediating androgen hormone action that ameliorates one or more physiological and pathophysiological conditions/disorders of the skin in human and non-human species, by administering an enantiomeric equol comprising R-equol, in an amount sufficient to bind free 5α-DHT and inhibit its binding with androgen receptors.

The present invention further relates to a method of treating and preventing androgen-related diseases mediated by androgen hormone action, by administering an enantiomeric equol comprising S-equol, in an amount sufficient to bind free 5α-DHT, thereby inhibiting its binding with androgen receptors, and to bind estrogen receptor subtypes.

The present invention can also relate to a method of treating and preventing androgen-related diseases mediated by androgen hormone action, by administering an enantiomeric equol comprising R-equol, in an amount sufficient to bind free 5α-DHT and inhibit its binding with androgen receptors.

The present invention also relates to a use of an enantiomer of equol comprising S-equol, for treating and preventing androgen-related diseases mediated by androgen hormone action, by administering an enantiomeric equol comprising S-equol, in an amount sufficient to bind free 5α-DHT and inhibit its binding with androgen receptors, and to bind estrogen receptor subtypes.

The present invention also relates to a method of providing a personalized treatment of one or more physiological and pathophysiological conditions/disorders of the skin in human and non-human species, mediated both by DHT and the estrogen receptors, comprising: 1) assessing the one or more disease states or conditions of a patient; 2) assessing the equol-producer status of the patient; 3) determining an optimally beneficial course of treatment, selected from the group consisting of a) a mode of administration, b) a dose amount, c) a dose interval, and d) the enantiomeric ratio of the equol dose.

The methods and compositions of the present invention are useful in the treatment and amelioration of a variety of skin condition/disorders selected from the group consisting of: skin integrity, collagen production, elastin production, elastase, skin thickness, blood flow in the skin, skin turgor, skin moisture content, vaginal dryness, prevention of collagen and elastin breakdown by matrix metalloproteinases, repair and prevention of wrinkles in skin, enhancing glycoaminoglycans and hyaluronic acid for improved skin appearance, wound healing, improvement of scars in skin, decrease oily skin by improving sebaceous gland function, skin age spots and, acne, male and female pattern baldness, hirsutism, scalp, facial and body hair health and growth, apocrine (sweat) gland function, inflammation of the skin, immune function in the skin, skin pore size, skin temperature and skin and hair abnormalities in steroid hormone synthesis/hormone action, metabolism of steroids and binding steroid receptors involving androgenic and/or estrogenic effects.

In another embodiment, the invention relates to a method of mediating androgen hormone action so as to ameliorate at least one condition of the skin or hair of a subject. The method includes administering equol, at least 1% of which is R-equol where R-equol binds free 5α-dihydrotestosterone and inhibits its binding with androgen receptor. In the method, the equol may include at least 5% of R-equol. In the method, the equol may include at least 10% of R-equol. In the method, the equol may include at least 20% of R-equol. In the method, the equol may include at least 25% of R-equol. In the method, the equol may be a racemic mixture of S-equol and R-equol. In the method, the equol may further include S-equol in an amount sufficient to bind estrogen receptor subtypes.

In yet another embodiment, the invention relates to a method of ameliorating at least one condition of the skin or hair of a subject. The method includes administering a composition comprising equol, at least 1% of which is R-equol where R-equol binds free 5α-dihydrotestosterone and inhibits its binding with androgen receptors. In the method, the equol may include at least 5% of R-equol. In the method, the equol may include at least 10% of R-equol. In the method, the equol may include at least 20% of R-equol. In the method, the equol may include at least 25% of R-equol. In the method the equol may be a racemic mixture of S-equol and R-equol. In the method, the composition may be administered topically, transdermally, or subdermally. In the method, the composition may be a topical composition comprising from at least about 0.001% to about 10% equol. In the method, the composition may further include a pharmaceutical active or an excipient. In the method, the composition may be administered orally at a dose of at least about 0.005 mg of equol per kg body weight. In the method, the composition may be in a delayed or a sustained release formulation. In the method, the composition may be administered via a lotion, a spray solution, a pad, a bandage, or a transdermal patch. In the method, the equol may further include S-equol in an amount sufficient to bind estrogen receptor subtypes. In the method, the condition of the skin or hair may be ameliorated cosmetically by at least one of: a) inducing increased skin integrity by cell renewal; b) enhancing water content or moisture of skin; c) enhancing glycoaminoglycans and hyaluronic acid for improved skin radiance; d) reducing trans epidermal water loss, skin flaking and scaling; e) invigorating for energetically healthy skin; f) improving skin thickness and enhanced cellular durability; g) strengthening skin collagen and improving skin health; h) enhancing skin tensile properties and improving the protective nature of the skin; i) increasing elastin to improve skin elasticity; j) protecting against elastase; k) protecting against collagenase; l) protecting against matrix metalloproteinases; m) repairing and reducing the appearance of dermal wrinkles and improving skin texture; n) reducing skin pores size and enhancing skin smoothness; o) rejuvenating and renewing skin; p) improving the appearance of scars and skin abrasions; q) decreasing oily skin by minimizing sebaceous gland secretion; r) reducing chronological, intrinsic and extrinsic dermal aging of the skin; s) improving skin age spots; t) enhancing hair pigmentation; and u) improving skin tone. In the method, the condition of the skin or hair is ameliorated pharmaceutically by at least one of: a) increasing blood flow in the skin; b) improving skin temperature and thermoregulation of the skin; c) increasing dermal thickness and inhibiting fibroblast cell apoptosis; d) inducing collagen production and increasing skin turgor; e) inducing elastin production and increasing skin elasticity; f) inhibiting elastase to improve skin texture and dermal lines; g) repairing and treating wrinkles and improving skin texture; h) positively influencing vascularization, skin thickness and skin turgor, and slowing down the process of aging; i) decreasing matrix metalloproteinases to positively influence skin collagen and elastin; j) enhancing skin repair and wound healing; k) improving appearance of scars and skin abrasions; l) decreasing oily skin by improving sebaceous gland function; m) stabilizing skin color changes and hair pigmentation and enhancing skin lightening; n) treating, ameliorating and protecting against hyperpigmentation, age-spots and photo-aging; o) decreasing or eliminating acne; p) decreasing scalp hair loss or enhancing the retention of scalp hair (in male and female pattern baldness); q) retarding facial and body hair growth, decreasing facial and body hair growth, and reducing hirsutism; r) reducing apocrine gland secretions and reducing excessive sweat gland function (hindradentitis and osmidrosis); s) reducing inflammation of skin and vaginal dryness; and t) attenuating skin and hair abnormalities in steroid hormone synthesis and function and metabolism of steroids and binding steroid receptors involving androgenic and/or estrogenic effects.

In yet another embodiment, the invention relates to a method of enhancing skin appearance. The method includes the step of administering a composition comprising equol, at least 1% of which is R-equol, where R-equol binds free 5α-dihydrotestosterone and inhibits its binding with androgen receptors. In the method, the equol may further include S-equol in an amount sufficient to bind estrogen receptor subtypes.

BRIEF DESCRIPTION OF THE DRAWINGS

FIG. 23 shows FACS analysis of elastase protein expression in 3-D cultures of human dermal monolayer fibroblast following incubation with vehicle, 10 nM equol or 10 nM 17β-estradiol added to tissue culture media.

FIG. 24 shows cell cycle analysis of apoptosis by FACS in 3-D cultures of human dermal monolayer fibroblast following incubation with vehicle, 10 nM equol or 10 nM 17β-estradiol added to tissue culture media.

FIG. 25 shows cell cycle analysis of cell cycling in S-G2M phases by FACS in 3-D cultures of human dermal monolayer fibroblast following incubation with vehicle, 10 nM equol or 10 nM 17β-estradiol added to tissue culture media.

DETAILED DESCRIPTION OF THE DRAWINGS AND THE PRESENTLY PREFERRED EMBODIMENTS

Figure 1:
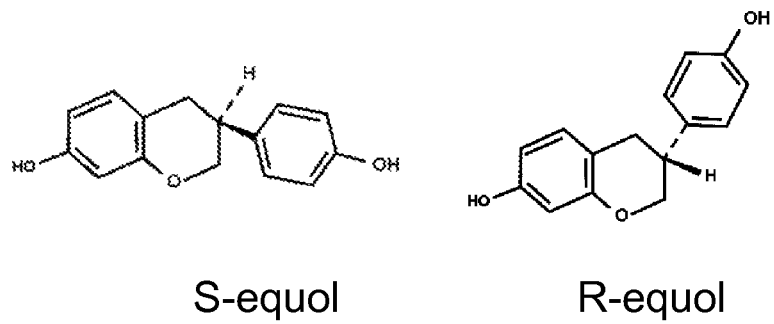
FIG. 1 shows the chemical structures of S-equol and R-equol enantiomers.

As used herein, the term "skin" refers to cell layers comprising the integument of a human or non-human individual, and its structural components such as hair, hair follicles, sebaceous glands, apocrine (sweat) glands, fingernails and toenails. Furthermore, the term "skin" as used herein encompasses tissues of the mucous membranes extending from the adjoining skin, such as the mouth and oral cavity, nose and nasal passages, eyes and eyelids, ears and outer ear canals, and the perineum and tissues of the anal and urogenital orifices.

As used herein, the term "affected area" refers to a region of the skin that is to be treated with a therapeutic molecule or compound containing a therapeutic molecule. The affected area may be the site of a skin condition or disease for which treatment is sought. In some cases, the affected area may encompass all skin on an individual. Alternatively, the affected area may be a site for which improvement of a cosmetic nature is sought, and can also include all skin on an individual.

As used herein, the term "systemic" or "systemically" refers to a mode of administration of a therapy that reaches an affected area of skin via the blood stream or lymphatic system. Examples of a systemic treatment include, but are not limited to, oral gavage or ingestion, intravenous or subdermal pump infusion, and injection via intramuscular, intraperitoneal, hypodermic or subdermic injection.

As used herein, the term "topical" or "topically" refers to a mode of administration that is applied directly to an affected area of the skin. Examples of a topical treatment include, but are not limited to application of cream, lotion, shampoo, conditioning lotion, spray, a pad, a bandage, a diaper, a proistened towelette, or transdermal patch; and local administration via intracutaneous injection or introduction of a lozenge or suppository.

As used herein, the term "skin parameters" refers to a variety of indicators of skin health, including but not limited to levels of collagen and elastin production, elastase, skin thickness, blood flow in the skin, skin turgor and moisture content, prevention of collagen and elastin breakdown by matrix metalloproteinases, absence of wrinkles in skin, presence of glycoaminoglycans and hyaluronic acid for normal skin appearance, ability of skin wounds to heal, normal sebaceous gland function, absence of skin age spots or pigmentation dysfunction, skin pore size, skin temperature, and normal growth of hair and nails.

As used herein, the term "skin integrity" refers to the presence of collagen and elastin in the extracellular matrix that gives skin its ability to stretch and retract to allow movement.

Equol (7-hydroxy-3(4'hydroxyphenyl)-chroman) represents the major metabolite of daidzin and daidzein, isoflavones found abundantly in soybeans and soy-foods, and is an important biologically active molecule. In animals, such as rodents, fed a phytoestrogen-rich diet, the major circulating isoflavone is equol, which accounts for 70-90% of the total circulating isoflavone levels. However, this is not the case in humans.

Equol is formed following the hydrolysis of the glycoside conjugates of daidzin from soy, and the methoxylated isoflavone formononetin, or its glycosidic conjugates found in clover. Once formed, equol appears to be metabolically inert, undergoing no further biotransformation, save phase II metabolism or a minor degree of additional hydroxylation in the liver. As with daidzein and genistein, the predominant phase II reactions are glucuronidation and, to a lesser extent, sulfation. Following the original discovery that equol's presence in urine was a function of soy food ingestion, it was observed that approximately 50-70% of the adult human population did not excrete equol in urine even when challenged daily with soy foods, for reasons that are unclear. Furthermore, even when the pure isoflavone compounds are administered, thereby removing any influence of the food matrix, it has been shown that many people do not convert daidzein to equol. This phenomenon has led to the terminology of a person being an 'equol-producer' or 'non-equol producer' (or 'poor equol-producer') to describe these two distinct populations.

Cut-off values have been empirically derived permitting assignment of individuals to either of these categories. People who have plasma equol concentrations of less than 10 ng/mL (40 nmol/L) can be classified as 'non-equol producers' and where levels are above 10 ng/mL (40 nmol/L) this defines 'equol producers'. This distinction can also be derived from the levels in urine, an equol producer being someone excreting greater than 1000 nmol/L. Although the excretion of equol is highly variable among individuals there is a large demarcation between those that can produce equol and those that cannot, consistent with a precursor-product relationship in enzyme kinetics catalyzing the reaction. There is consequently an inverse relationship between urinary daidzein and equol levels, and thus far no significant gender differences have been defined.

A mechanism of action for equol has been identified with important ramifications in skin health and disease and which indicates a broad and important usage for equol in the treatment of androgen and/or estrogen mediated pathologies of skin and hair. Equol can act as an anti-androgen or estrogen receptor agonist or antagonist. The anti-androgenic properties of equol are unique in that equol does not bind the androgen receptor (AR) but rather, specifically binds 5α-dihydrotestosterone (5α-DHT) with high affinity, thereby preventing 5α-DHT from binding the AR. Furthermore, both the R- and S-enantiomers of equol specifically bind 5α-DHT, sequester 5α-DHT from the AR and block 5α-DHT's actions in physiological processes in vivo. Racemic equol, which constitutes R-equol and S-equol, and R-equol or S-equol alone, selectively bind 5α-DHT.

In mammals, there are two principal androgens, testosterone and its 5α-reduced metabolite, 5α-DHT. 5α-DHT is recognized as the most potent androgen in the mammalian body. The AR, which is encoded by a single-copy gene located on the human X-chromosome, specifically mediates the actions of androgens. Although both testosterone and 5α-DHT bind the AR, certain tissues (i.e. prostate gland, hair follicles, etc.) that are only slightly influenced by testosterone are greatly influenced by 5α-DHT. Furthermore, 5α-DHT has been implicated in a number of diseases and disorders. Because equol specifically binds and prevents the actions of 5α-DHT, there is an indication for a broad and important usage for equol in the treatment of androgen-mediated pathologies of skin and hair.

Equol has a structure similar to the steroidal estrogen estradiol. FIG. 1 shows the chemical structures of R-equol and S-equol. Equol is unique among the isoflavones in that it possesses a chiral center and as such exists as two distinct enantiomeric forms, the R- and S-enantiomers. The R- and S-enantiomers conformationally differ and this is predicted to influence how an equol enantiomer fits into the binding site in the cavity of the dimerized ER complex, and how it binds with 5α-DHT.

Approximately 50% of equol circulates in the free or unbound form in humans, and this is considerably greater than the proportion of free daidzein (18.7%) or estradiol (4.6%) in plasma. Since it is the unbound fraction that is available for receptor occupancy, and presumably for binding 5α-DHT, this would effectively contribute to enhancing the overall potency of equol.

All known previous studies on equol appear to have been conducted with the racemic form of equol. There has in general been a lack of appreciation that two forms of equol exist or that the enantiomers may behave differently, and to our knowledge no previous study has reported on the specific actions or activity of the individual enantiomers. R- and S-equol specifically bind 5α-DHT. Equol racemic, R-equol or S-equol, does not bind the androgen receptor (AR). Compared to 17β-estradiol the relative binding affinities of the R- and S-equol enantiomer for ERα {fraction (1/210)} and {fraction (1/49)} less than that of 17β-estradiol, respectively. However, the S-equol enantiomer seems to be largely ERβ-selective with a relatively high affinity for ERβ. Enantiomer S-equol binds ERβ at similar concentrations to that of 17β-estradiol [equol, Kd=0.7 nM vs. 17β-estradiol, Kd=0.15 nM], but its preferential affinity for ERβ subtype defines S-equol as a SERM. The R-equol enantiomer binds at approximately {fraction (1/100)} the affinity, however, if R-equol is present in extremely high concentrations, it does have SERM properties. Thus, S- and R-equol have the capability to selectively bind the most potent circulating androgen, 5α-DHT, and S-equol has sufficient affinity for ERβ to classify it as having SERM properties.

The ability of both S-equol, the natural metabolite of daidzein, and R-equol to antagonize the actions of the potent androgen dihydrotestosterone, 5α-DHT opens up opportunities for cosmetic, dietary, nutraceutical, and pharmacological approaches to prevention and treatment of disease where the potent androgen 5α-DHT plays a detrimental role, including, but not restricted to, prostate cancer, obesity, skin diseases, and hair loss. Additionally, the estrogenic actions of S-equol can also be of benefit in treating or preventing BPH and prostate cancer because the combined actions of equol acting at the estrogen receptor level and as an antiandrogen.

R-equol, although not naturally occurring, is of considerable importance because of its ability to modulate androgen-mediated processes in the body. In binding studies, equol enantiomers specifically bind 5α-DHT, but not testosterone, DHEA or estrogen. By doing so, equol sequesters 5α-DHT from the androgen receptor without directly binding the androgen receptor itself. In vivo studies demonstrate that equol treatment of intact male rats significantly decreased prostate and epididymis but not testes weights. In castrated male rats treated with 5α-DHT after administering equol, equol blocked 5α-DHT's trophic effects on the prostate gland and its negative feedback effects on plasma luteinizing hormone (LH) levels.

Equol can act as an anti-androgen, by specifically binding 5α-DHT and preventing 5α-DHT from binding to the androgen receptor (AR) without itself binding the AR. Further, 5α-DHT that has already been bound to the AR will not be competitively bound by enantiomeric equol. The enantiomeric equol may be brought into contact with the 5α-DHT in vitro or in vivo. When the 5α-DHT is to be contacted in vivo, the equol may be administered by any route that allows absorption of equol to the blood stream or into the skin when applied topically. Biologically available 5α-DHT is free and unbound by any native ligand prior to binding with equol.

Reproductive organs such as the prostate and epididymis are known to be under androgenic control. Previous data has shown that before puberty, when circulating androgen levels are very low, rats fed a diet containing high levels of soy-derived isoflavones have prostate weights that are not altered by the consumption of this diet. However, after puberty when androgen levels increase, prostate weights are significantly decreased in phytoestrogen-rich-diet fed rats compared to animals fed a phytoestrogen-free diet. These data are similar to the present findings that equol-treated intact rats display significant decreases in prostate and epididymis weights, without alterations in testes or pituitary weights. Notably, if the prostate and epididymal values are standardized to body weight (per 100 grams) the ratios are still significantly different between equol-treated and control values. Equol also blocked 5α-DHT's androgenic trophic influence on the prostate and epididymis, without significantly altering testosterone levels.

5α-DHT has negative feedback effects on circulating plasma levels of luteinizing hormone (LH). Equol significantly increases LH levels by binding 5α-DHT and preventing this feedback effect. Equol completely reverses the inhibitory action of 5α-DHT on LH levels in gonadectomized (GDX) males, whereas 5α-DHT plus equol-treated male rats display LH levels similar to that of control values. These data further suggest that equol has the specific ability to bind 5α-DHT, presumably in the blood circulation system, and block the hormonal action of 5α-DHT in suppressing LH production or secretion. Therefore an embodiment of the present invention is a method of modulating LH levels in an individual by contacting the 5α-DHT of the individual with enantiomeric equol. The equol can be administered by any route that allows absorption of equol into the skin or blood stream, with the amount administered in accordance with the nature of the ailment to be treated and size of the individual. In some cases, it may be desirable to provide a combination of both systemic and topical treatments.

Enantiomeric equol can be prepared by chemical synthesis, and can be isolated from racemic mixtures, typically using a chiral-phase column, by known means. S-equol can be made with high enantioselectivity using a biological process that employs the equol-producing microorganism associated with metabolism of equol from isoflavones such as daidzein. These means are described in PCT Patent Publication WO04-009035, which is incorporated herein by reference in its entirety.

Treatment of Disease by Administering S-Equol, R-equol, and Mixtures:

This present invention provides a means for an individual subject to overcome the problem of not being able to produce equol in vivo, or to supply R-equol in particular, by providing delivery of equol enantiomers, the S-equol or R-equol, racemic or non-racemic mixtures of S-equol and R-equol directly, circumventing the need for intestinal bacteria for its production or for the need to consume soy foods with equol's precursor isoflavones. The delivery of S-equol can also supplement the in vivo production of S-equol in 'equol-producers', as well as in 'non-equol producers.'

Supplementing the diet of an equol producer with an equol enantiomer or mixture, can provide benefits when the ordinary level of S-equol produced by the equol producer is inadequate because of 1) insufficient consumption of isoflavones to produce equol, 2) antibiotic use that ablates the activity of intestinal bacteria to make equol from precursor isoflavones, or 3) other health factors that impact the level of equol production or absorption, such as short bowel syndrome or surgical construction of an intestinal stoma such as ileostomy. In addition, a supplemental level of equol is believed to provide enhanced effect on the health and well-being of the person.

This invention provides a method for delivering S-equol, R-equol, racemic equol, or non-racemic mixtures of equol, in sufficient amounts to have health benefits toward androgen-related diseases and conditions associated therewith. The anti-androgenic activity of equol can affect a number of tissues throughout the body. In particular, the blocking of androgenic activity of 5α-DHT can be beneficial for the treatment and prevention of: female- and male-pattern baldness, facial and body hair growth (hirsutism), skin health (acne, anti-aging such as wrinkle prevention and repair and anti-photo aging), and skin integrity (collagen and elastin robustness). The method can be a topical administration, a systemic administration, or a combination of topical and systemic administration.

For topical administration, the concentration of equol applied to an affected area of skin will range from 0.001% to 10%. In other embodiments, the concentration of equol applied to an affected area of skin will range from 0.01% to 10%. Typically, 0.01% to 1% is effective to induce increased skin integrity, collagen production, elastin production, elastase, skin thickness, blood flow in the skin, skin turgor, skin moisture content, prevention of collagen and elastin breakdown by matrix metalloproteinases, repair and prevention of wrinkles in skin, enhancing glycoaminoglycans and hyaluronic acid for improved skin appearance, wound healing, improvement of scars in skin, decrease oily skin by improving sebaceous gland function, skin age spots and skin lightening, acne, male and female pattern baldness, hirsutism, scalp, facial and body hair health and growth, apocrine (sweat) gland function, inflammation of the skin, immune function in the skin, skin pore size, skin temperature and skin and hair abnormalities in steroid hormone synthesis/hormone action, metabolism of steroids and binding steroid receptors involving androgenic and/or estrogenic effects. In some cases, a higher dose is required due to the presence of a skin condition or disease, or because the patient is a non-equol producer. In this situation, the concentration of topically-applied equol can be up to 10%, topical administration may be performed more frequently, or systemic administration may be used in combination with or in place of topical administration.

For systemic administration, the amount of composition comprising the equol is administered in an amount sufficient to produce a transient level of enantiomeric equol in the blood plasma of the mammal of at least 5 nanograms per milliliter (ng/mL), more typically at least 10 ng/mL or greater, or transient levels of enantiomeric equol in urine of greater than 1000 nmol/L. Typically, the composition is administered orally in a dose amount of at least about 0.005 mg, at least about 1 mg, more typically of at least 5 mg, and of up to 200 mg, more typically, up to 50 mg, of enantiomeric equol. Typical plasma concentrations of R-equol in plasma after oral administration of 20 mg of R-equol enantiomer to a healthy adult is shown by the pharmacokinetics of the plasma appearance/disappearance plots of R-equol in FIG. 2. A typical level of bioavailability of S-equol in plasma after oral administration of 20 mg of S-equol to a healthy adult is similar to that shown for R-equol.

The ability to deliver R- and/or S-equol in sufficient amounts is believed to provide several advantages over delivery of a racemic mixture of equol. First, the potency of R-equol or S-equol alone would typically be at least twice that of the racemic mixture. Second, the human body only produces S-equol, and therefore, a composition comprising only S-equol represents a "natural" product with an ingredient, S-equol, with which the body is familiar. Third, since the R-equol enantiomer has unique properties, a treatment composition comprising only, or substantially only, the R-enantiomer can produce beneficial and/or therapeutic effects. And fourth, administration of R-equol would supplement any endogenous S-equol present and allow for both estrogenic and anti-androgenic actions to occur in the body.

The invention includes the use of enantiomeric equol to treat and prevent diseases and conditions related to male- and female-pattern baldness. 5α-DHT is a known cause of scalp hair loss. An androgen, specifically the principal circulating androgen, testosterone, is converted to the more potent androgen, dihydrotestosterone (5α-DHT) (in the hair follicle), and the hormonal action of 5α-DHT on scalp hair follicles cause hair loss. Thus, if the hormonal action of 5α-DHT can be blocked, such as by the use in the present invention of equol to bind 5α-DHT in the circulation (within blood vessels) and within the hair follicle, then scalp hair loss can be decreased or prevented.

The invention includes the use of enantiomeric equol to treat and prevent diseases and conditions related facial and body hair. Facial and body hair are regulated by androgens, but oppositely to that of the regulation of scalp hair. Specifically, the more potent androgen, 5α-DHT, increases facial and body hair. 5α-DHT also increases the production of sebum (oil) from the sebaceous gland, which can contribute to an increase in acne. Thus, the binding of 5α-DHT by equol can cause a decrease in facial and body hair and in secretion of sebum (oil), and a reduction or prevention of acne.

The invention includes the use of enantiomeric equol to treat and prevent diseases and conditions related to skin effects, skin quality and integrity, skin aging, skin photo-aging, and skin pigmentation and lightening. Estrogens, before but especially after menopause, improve skin health by increasing elastin and collagen content to improve skin characteristics or robustness. Also, when skin is damaged by acne or other skin disruptions (scratches, popping pimples or minor cuts, etc.), the repair mechanism is faster and the skin heals better if estrogen or estrogen-like compounds, such as equol, are present. It is believed that an enantiomeric equol, and particularly S-equol or a mixture of the enantiomers or racemic equol stimulates elastin and collagen, and also can protect against photo-aging. The ability of equol to block the hormone action of 5α-DHT can decrease sebum oil production from the sebaceous gland, which can decrease or eliminate acne. Since S-equol binds estrogen receptor(s) (mainly ERβ), the protective effects of this estrogen-like molecule stimulates elastin and collagen in the skin. Additionally, since equol is a strong antioxidant, it can protect the skin from aging, including photo-aging.

Sex steroid hormones are involved in the regulation of skin development and functions, such as secretions, as well as in some skin pathological disorders. It is well established that the actions of estrogens and androgens hormone are mediated by the presence of their receptors in skin, hair and glands associated with skin. See Pelletier and Ren, *Histol Histopathology,* 19: 629-636, 2004. For example, androgen receptors (AR) have been localized in most keratinocytes in the epidermis/dermis and AR was seen in approximately 10% of fibroblasts. However, in sebaceous glands, AR is abundant in basal cells and sebocytes. In hair follicles AR expression is restricted to dermal papillar cells. ERβ is highly expressed in the epidermis, sebaceous glands (basal cells and sebocytes) and eccrine sweat glands. In hair follicles, ERβ is widely expressed in dermal papilla cells, inner sheath cells, matrix cells and outer sheath cells including the bulge region.

Since equol is a metabolite of daidzein and possesses the characteristics of selective estrogen receptor modulators (SERMS), where in some cells and tissue sites it acts like an estrogen agonist and in others an estrogen antagonist, it is reasonable to propose that equol can have dual estrogen-like hormone actions at various cells/tissue containing ERβ. It has been established that equol (racemic) has the ability to bind ERβ through its enantiomer S-equol, since R-equol has low affinity for ERα or ERβ. However, both S-equol and R-equol are of considerable importance because of their ability to specifically bind and biologically inactive 5α-DHT that plays a major role in: a) scalp and facial/body hair follicle growth, such as androgenetic alopecia or male-pattern baldness, and hirsutism in women or female-pattern baldness, b) acne and sebaceous gland function, c) wound healing and d) skin disorders such as apocrine gland dysfunction, hidradentitis suppurativa or osmidrosis. Finally, estrogens are known to positively influence skin parameters, wound healing, hair follicle health, sebaceous and apocrine gland function, epidermal and hair follicle pigmentation, and malignant melanoma.

Estrogen is known to be a major hormonal factor in the maintenance of human skin. It is known to stimulate collagen production in the dermis, increase skin thickness, increase the vascularization of the skin and increase the mitotic activity of the epidermis. See Brincat M P, *Maturitas,* 29:107-117, 2000; Punnonen R, *Acta Obstet Gynecol Scand Suppl,* 21: 3-44, 1972; Hasselquist, M B et al., *J Clin Endocrinol Metab,* 50: 76-82, 1980; and Shah M G and Maibach H I, *Am J Clin Dermatol,* 2:143-150, 2001. Specifically, estrogen is known to be a natural modulator of matrix metalloproteinases (MMP), as described by Pirila E et al., *Curr Med Chem,* 8:281-294, 2001. MMPs are known to break down collagen and elastin. This could be due to environmental (exposure to chemicals, pollution, extreme temperature environments—cold or heat), mechanical (contractions of facial muscles, such as smiling, frowning, smoking or drinking from a straw) or biological aging. These factors are influenced by genetics and the natural processes of aging, wherein the skin becomes thin, wrinkles appear due to the reduction in collagen and especially elastin, and the robust appearance of the skin declines. Estrogen treatment has also been shown to increase the concentrations of glycoaminoglycans (acid mucopolysaccharides and hyaluronic acid) that enhance the water content or moisture of skin and influence skin turgor. See also Raine-Fenning N J et al., *Am J Clin Dermatol*, 4:371-378, 2003.

The invention includes the use of S-equol, or racemic or non-racemic mixtures of S- and R-equol to ameliorate or block the negative effects of cancer therapies that involve estrogen receptors, such as tamoxifen. Tamoxifen treatment has been shown to cause vaginal dryness, which can be ameliorated by equol through its SERM actions. The invention can be used in a similar manner to ameliorate vaginal dryness that accompanies menopause or post-menopause vaginal dryness.

The invention includes the use of S-equol, or racemic or non-racemic mixtures of S- and R-equol to block the negative effects of 5α-DHT and decrease MMPs to positively influence skin collagen, elastin, vascularization and skin thickness and skin turgor and slow down the process of environmental, mechanical and biological aging.

Estrogen is important in the rate and quality of wound healing. See Pirila E et al., *Curr Med Chem*, 8:281-294, 2001 and Ashcroft G E et al., *Nat Med*, 3: 1209-1215, 1997. It has been demonstrated that ERβ is the predominant estrogen receptor in adult human scalp skin and the pilosebaceous unit (hair follicle) of the skin. See Thornton M J et al., *Exp Dermatol*, 12: 181-190, 2003 and Thornton M J, et al., *J Invest Dermatol Symp Proc*, 8: 100-103, 2003. Furthermore, it has been reported that physiological levels of 5α-DHT depress wound healing by impairing immune function and promoting inflammation. See Nitsch S M et al., *Arch Surg*, 139:157-163, 2004 and Gilliver S C et al., *Thromb Haemost*, 90: 978-985, 2003. MMPs are also involved in wound healing and are modulated by estrogens.

The invention includes the use of S-equol, racemic or non-racemic mixtures of R- and S-equol, via its R- and S-enantiomers binding to extracellular and intracelluar 5α-DHT, to biologically inactivate this potent androgen and positively influence wound healing. At the same time a racemic or non-racemic mixture of R- and S-equol will improve the rate and quality of wound healing via an ERβ hormone-mediated mechanism.

A built-in rhythm of activity in scalp hair follicles results in the growth of new hairs and the molting of old ones. This activity is known to be under the influence of steroid hormones. Scalp hair follicle growth is specifically inhibited by 5α-DHT, while at the same time, facial and body hair follicles are stimulated by 5α-DHT. It is known that postmenopausal women experience female-pattern balding patterns due to the loss of ovarian steroid hormones and the increased ratio of androgens/estrogens during this period, as described by Brincat (see reference above). Postmenopausal women also experience hirsutism, or increased facial and body hair growth, during this period, and with increased androgen production during the pre-menopausal period. Pre-menopausal women also experience hirsutism with increased androgen production. See Reed M J and Franks S, *Baillieres Clin Obstet Gynaecol*, 2: 581-595, 1988. Castrated males, who have low levels of androgens, or humans with genetic 5α-DHT-reductase deficiency do not experience male-pattern baldness (Trueb R M, *Exp Gerontol*, 37: 981-990, 2002).

It is also known from in vitro and in vivo studies that estrogens increase the hair follicle growth or life cycle and stimulate the secretion of vascular endothelial growth factor (VEGF) in dermal papilla cells that influence blood flow to the hair follicle. See also Lachgar S et al., *J Invest Dermatol Symp Proc*, 4: 290-295, 1999.

The invention includes the use of S-equol, racemic or non-racemic mixtures of R- and S-equol to biologically inactivate the potent androgen 5α-DHT and inhibit the negative effects on scalp hair follicle growth in both men and women. Equol will stimulate hair follicle life cycle and enhance vascular endothelial growth factor (VEGF) in dermal papilla cells to positively influence scalp hair growth. Conversely, R-equol and/or S-equol can block the hormonal actions of 5α-DHT, and facial and body hair growth will be reduced.

Estrogens decrease the size and inhibit sebaceous gland secretion in males and females. See Pochi P E and Strauss J S, *J Invest Dermatol*, 62: 191-210, 1974 and Lade F et al., *Horm Res*, 54: 218-229, 2000. ERβ is widely and highly expressed in the sebaceous gland and estrogen hormone action via this receptor apparently reduces oil gland secretion associated with hair follicles. On the other hand, androgen receptors in the sebaceous glands are activated by 5α-DHT. 5α-DHT in the sebaceous gland stimulates oil production that is associated with attracting bacteria and thus the promotion and production of acne.

The invention includes the use of S-equol, racemic or non-racemic mixtures of R- and S-equol to biologically inactivate the potent androgen 5α-DHT and inhibit the production of oil secretion from the sebaceous gland to reduce the incidence of acne. A combination of enantiomers (R-equol and S-equol) will reduce the size and inhibit the production of oil from the sebaceous gland to assist in the amelioration or prevention of acne.

The apocrine gland develops from the outer root sheath of the hair follicle and remains attached to it. Apocrine glands are associated with hairy regions of the body that produce sweat mostly from the armpits and groin region, as described by Jakubovic H R et al., Dermatology, Third Edition, Philadelphia, W. B. Saunders, 1992, pp. 69-77. Hidradentitis suppurativa and osmidosis are conditions due to inflammation of the large sweat glands associated with the armpits and groin. See Sato T et al., *Br J Dermatol*, 139: 806-810, 1998. Patients with these disorders have excessive or abnormal odor derived from apocrine sweat (osmidrosis). The condition is more common in females and appears to improve with estrogen and/or antiandrogen treatments, suggesting that these specialized glands are regulated by estrogens and androgens. See also Offidani A et al., *J Clin Pathol*, 52: 829-832, 1999. Specifically when androgen hormone action has been examined, high levels of 5α-reductase activity have been detected in the apocrine glands in patients who suffer from excessive or abnormal odor for their apocrine (sweat) glands, and the action of 5α-DHT has been implicated in these conditions.

The invention includes the use of S-equol, racemic or non-racemic mixtures of R- and S-equol to biologically inactivate the potent androgen hormone 5α-DHT and inhibit the production of sweat secretion from apocrine glands and reduce the incidence of hidradentitis and osmidrosis. Concomitantly, in a combination of the ratios of enantiomers (R-equol and S-equol), equol will reduce production of sweat from apocrine glands to assist in the prevention of hidradentitis and osmidrosis.

Several studies have shown that epidermal melanocytes are estrogen responsive. There are several reports of estrogen-containing oral contraceptives causing hyperpigmentation of the face in women, as described by Wade T R et al., *Obstet Gynecol*, 52: 233-242, 1978.

The invention includes the use of S-equol, or racemic or non-racemic mixtures of R- and S-equol to biologically inactivate the potent androgen hormone 5α-DHT and enhance the hormonal action of equol at estrogen receptors. Epidermal melanocytes will be inhibited via the SERM action of equol, and the result will be a skin-lightening effect. Thus, equol can be an effective treatment for age or skin spots, especially on the face and hands.

The invention includes the use of S-equol, or racemic or non-racemic mixtures of R-equol and S-equol to biologically inactivate the potent androgen hormone 5α-DHT and enhance the hormonal action of equol at estrogen receptors. Hair follicle melanocytes are stimulated via the SERM action of equol, and the result is an enhancement of hair pigmentation. See Tobin D J and Bystryn J C, *Pigment Cell Res,* 9: 304-310, 1996; Thorton M J, *Exp Dermatology,* 11: 487-502, 2002; and Ohuchi A et al., in: *Third Intercontinental Meeting of Hair Research Societies,* Japan, 2001. Thus, equol can be an effective treatment for modulating the tone and color of hair follicles and thus change hair pigmentation.

Due to the association of hair follicles with the formation of malignant melanomas, the SERM characteristics of equol may influence malignant melanomas in a positive manner. See Kanda N and Watanabe S, *J Invest Dermatol,* 117: 274-283, 2001; Richardson B et al., *Br J Cancer,* 80: 2025-2033, 1999; and Durvasula R et al., *Climacteric,* 5: 1970200, 2002. For example, treatment of human metastatic melanoma cell lines incubated with estradiol inhibited the uptake of $^3$H-thymidine, which was counteracted by the administration of an antiestrogen. Moreover, estradiol can inhibit the invasion of human melanoma cells through the activation of fibronectin. Finally the mean age of presentation of malignant melanoma in women is the early fifties, a time concomitant with the onset of menopause. Melanoma has traditionally been considered to be an estrogen-receptor positive tumor, however recent evidence now refutes this.

The invention includes the use of S-equol, or racemic or non-racemic mixtures of R-equol or S-equol to biologically inactivate the potent androgen hormone 5α-DHT and enhance the hormonal action of equol at estrogen receptors. Via the SERM action of equol, the formation of malignant melanomas will be inhibited and hair follicle melanocytes will be stabilized resulting in the prevention and treatment of malignant melanomas.

Other embodiments of the present invention include the use of equol as a diagnostic agent in androgen-related skin or hair disorders as well as disorders arising from disturbances in estrogenic/androgenic balance. In these embodiments, equol is administered to an individual to bind 5α-DHT and thereby prevent 5α-DHT binding to androgen receptors. The changes in estrogenic balance are then measured or the change in androgen-binding is assessed to diagnose or further elucidate androgen-related anomalies of skin or hair.

Equol has been found to improve skin health by increasing elastin and collagen content to improve skin characteristics or robustness. The mechanism of this action is believed to block the hormone action of 5α-DHT that would in turn decrease oil production from the sebaceous glands to decrease acne and other skin disorders. Since equol, and particularly S-equol, binds estrogen receptor(s), the protective effects of the estrogen-like molecules stimulate production of elastin and collagen in the skin that is thought to be mediated via ERβ. In addition, the antioxidant properties of equol protect against photo-aging and, in general, the aging of the skin.

Equol can be administered to bind 5α-DHT prior to or along with other therapeutic moieties in order to assess the binding capacity of 5α-DHT with respect to the therapeutic moiety in question. Also, androgen-binding moieties can be administered following administration of equol to assess the efficacy of the androgen-binding moiety to restore androgen activity and balance estrogenic activity in the absence of 5α-DHT binding. Further, equol can be administered in the presence of 5α-DHT-binding moieties in order to displace these naturally occurring or xenobiotic 5α-DHT-binding moieties from 5α-DHT.

Enantiomeric equol can be orally administered by supplying an oral dosage form of equol, which results in effective absorption of equol to the blood stream. Administration of equol may be made by routes other than oral if desired. For example, it is contemplated that rectal or urethral administration may be used to administer equol for the treatment of enlarged prostate or to prevent prostate enlargement. Additionally, it is contemplated that the active ligand binding site of the equol molecule may be isolated and synthesized for administration, which can provide 5α-DHT binding without the full equol molecule. The dose of the equol molecule or fragment thereof having 5α-DHT-binding abilities is dependent upon the route of administration and the condition to be treated. Based on our in vivo studies it is apparent that relatively low doses of equol antagonize much higher doses of 5α-DHT, and this may be explained by the marked differences in the binding of equol to serum protein compared with 5α-DHT. The latter circulates mostly bound to proteins, while equol is 50% free. Generally, a dose sufficient to produce a concentration of equol or active fragments thereof in the bloodstream of the recipient of at least about 0.2 mg equol per kg weight of the recipient and preferably at least about 0.5 mg/kg. The dose may be increased dramatically without incurring significant dose-limiting side effects to greater than about 10 mg/kg. Oral administration can be effected in microencapsulated forms that can provide delayed or sustained release of the medicament.

Equol can be administered topically, transdermally, and subdermally in a variety of forms, including lotions, ointments, foams (including shaving creams), and sprays, or as an active ingredient on a substrate suitable for topical application, such as a pad, a surgical bandage, an adhesive bandage, a premoistened towellette, an infant or adult incontinent diaper (such as described in U.S. Pat. No. 5,525,346, incorporated herein by reference), a feminine sanitary product, or a transdermal skin patch (such as described in U.S. Pat. Nos. 5,613,958 and 6,071,531, incorporated herein by reference), electromechanical devices, including micropumps systems (such as described in U.S. Pat. Nos. 5,693,018 and 5,848,991, incorporated herein by reference), and subdermal implants (such as described in U.S. Pat. No. 5,468,501, incorporated herein by reference).

A composition useful in the practice of the present invention comprises an at least physiological acceptable quantity of equol that is able to at least partially bind and sequester free 5α-DHT (but not testosterone or DHEA) thereby preventing it binding to the androgen receptor following administration to an individual thereby having important ramifications in health and disease and a broad and important use in the treatment of androgen-mediated pathologies.

A composition containing S-equol, R-equol, a racemic equol mixture, or a non-racemic equol mixture, can be made for oral consumption. The composition or a product containing the composition can be a marketed or institutional food product, a pharmaceutical, and an OTC medicament. A food composition can comprise at least 1 mg, and typically up to 200 mg, enantiomeric equol or equol mixtures, per serving. An orally-administered medicament can comprise at least 1 mg, and typically up to 200 mg, enantiomeric equol or equol mixture, per dose. A product for topical application can comprise at least 0.001% or 0.01%, and up to 10%, by weight S-equol, or R-equol, or enantiomeric mixtures. Selected concentration ranges include from about 0.001% to about 3%; from about 0.001% to about 1%; from about 0.01% to about 3%, from about 0.1% to about 1%, from about 0.1% to about 3%, from about 0.1% to about 5%, from about 0.3% to about 1%, from about 0.3% to about 3%, from about 0.3% to about 5%, from about 0.5% to about 1%, from about 0.5% to about 3%, and from about 0.5% to about 5%. Typically, 0.01% to 1% is an effective concentration range that can be applied at a variety of intervals. In some cases, it is preferred to apply equol in a concentration of up to 5% to treat some pathological conditions or diseases. There are also instances in which a concentration of up to 10% may be required, due to the severity of a condition or disease, or because an individual is a non-equol producer, thus requiring administration of a greater amount of exogenous equol.

A topical composition of the present invention can include other cosmetic and pharmaceutical actives and excipients. Such suitable cosmetic and pharmaceutical agents include, but are not limited to, antifungals, vitamins, anti-inflammatory agents, antimicrobials, analgesics, nitric oxide synthase inhibitors, insect repellents, self-tanning agents, surfactants, moisturizers, stabilizers, preservatives, antiseptics, thickeners, lubricants, humectants, chelating agents, skin penetration enhancers, emollients, fragrances and colorants.

In some individuals it is preferred to use a combination of systemic and topical administration. This can be due to the severity of the condition or disease, or because an individual is a non-equol producer, thus requiring administration of a greater amount of exogenous equol.

An enantiomeric equol can also be an enantiomeric equol conjugate, conjugated at the C-4' or the C-7 position with a conjugate selected from the group consisting of glucuronide, sulfate, acetate, propionate, glucoside, acetyl-glucoside, malonyl-glucoside, and mixtures thereof.

A composition or preparation comprising enantiomeric or mixture of equol, for administering to subjects for the treatment and/or prevention of, or for reducing the predisposition to, androgen-related diseases and conditions related thereto, can also comprise one or more pharmaceutically acceptable adjuvants, carriers and/or excipients. Pharmaceutically acceptable adjuvants, carriers and/or excipients are well known in the art, for example as described in the Handbook of Pharmaceutical Excipients, second edition, American Pharmaceutical Association, 1994 (incorporated herein by reference). The composition can be administered in the form of tablets, capsules, powders for reconstitution, syrups, food (such as food bars, biscuits, snack foods and other standard food forms well known in the art), or in drink formulations. Drinks can contain flavoring, buffers and the like.

The composition can comprise a non-racemic mixture of S-equol and R-equol, having an enantiomeric excess (EE) for S-equol of more than 0% and less than 90%. A composition that has an EE of 0% is a 50:50 racemic mixture of the two enantiomers. The composition can be made directly from a racemic mixture, by an incomplete separation and removal of either the R-equol or S-equol enantiomer from the racemic mixture. The composition can also be made by combining a first equol component comprising a mixture (either a non-racemic or racemic mixture) of equol, with a second component comprising a composition consisting essentially of S-equol or R-equol. This produces a non-racemic composition that has an excess of S-equol or R-equol. Depending upon the specific benefit or indication for the R-equol component and the S-equol component in a composition, a composition can be prepared comprising S-equol and R-equol at a ratio of S-equol to R-equol from greater than about 50:50 to about 99.5:1, more typically about 51:49 to about 99:1, and from less than about 50:50 to about 1:99.5, more typically about 49:51 to about 1:99. The composition typically does not comprise a significant amount of any other androgen-receptor binding compound. Selected ratios of S-equol to R-equol includes from about 3:1 to about 19:1, about 3:1 to about 9:1, about 4:1 to about 19:1, and about 4:1 to about 9:1.

Compositions suitable for oral administration can be presented in discrete units, such as capsules, cachets, lozenges, or tablets, each containing a predetermined amount of the extract; as a powder or granules; as a solution or a suspension in an aqueous or non-aqueous liquid; or as an oil-in-water or water-in-oil emulsion.

A fuller understanding of the invention and its uses can be derived from the following experiments.

Experiment 1. Determination of Receptor Binding Capacity of Equol S- and R-Enantiomers.

In vitro binding studies were performed to examine the relative affinities of S- and R-enantiomeric equol with the estrogen receptors ERα and ERβ. Full length rat ERα expression vector (pcDNA-ERα; RH Price UCSF) and ERβ expression vector (pcDNA-ERβ; T A Brown, Pfizer, Groton, Conn.) were used to synthesize hormone receptors in vitro using the TnT-coupled reticulocyte lysate system (Promega, Madison, Wis.) with T7-RNA polymerase, during a 90 min reaction at 30° C. Translation reaction mixtures were stored at −80° C. until further use. In order to calculate and establish the binding affinity of the S-equol and R-equol enantiomers for ERα and ERβ, 100 μL aliquots of reticulocyte lysate supernatant were incubated at optimal time and temperature; 90 min at room temperature (ERβ) or 18 hrs at 4° C. (ERα), with increasing (0.01-100 nm) concentrations of [$^3$H] 17β-estradiol (E2). These times were determined empirically and represent optimal binding of receptor with estrogen. Nonspecific binding was assessed using a 300-fold excess of the ER agonist, diethylstilbestrol, in parallel tubes. Following incubation, bound and unbound [$^3$H]E2 were separated by passing the incubation reaction through a 1 mL lipophilic Sephadex LH-20 (Sigma-Aldrich Co., Saint Louis, Mo.) column. Columns were constructed by packing a disposable pipette tip (1 mL; Labcraft, Curtin Matheson Scientific, Inc, Houston, Tex.) with TEGMD (10 mm Tris-C1, 1.5 mm EDTA, 10% glycerol, 25 mm molybdate, and 1 mm dithiothreitol, pH 7.4)-saturated Sephadex according to previously published protocols (Handa et al., 1986; O'Keefe and Handa, 1990). For chromatography, the columns were re-equilibrated with TEGMD (100 μL), and the incubation reactions were added individually to each column and allowed to incubate on the column for an additional 30 min. Following this incubation, 600 μL of TEGMD were added to each column, flow-through was collected, 4 mL scintillation fluid was added, and samples were counted (5 min each) in an 2900 TR Packard scintillation counter (Packard Bioscience, Meriden, Conn.).

Competition binding studies were used to assess the estrogenic properties of equol's S-equol and R-equol enantiomers. Based on the ability of S- and R-equol to compete with [$^3$H]E2 for ER binding, the affinities for in vitro translated ER were shown to be very different for the two enantiomers. The S-equol enantiomer showed greatest affinity for ERβ [Kd (nM)=0.73±0.2], while its affinity for ERα was relatively low by comparison [Kd(nM)=6.41±1.0]. The R-equol enantiomer possessed a much lower affinity for both ERβ [Kd (nM)= 15.4±1.3] and ERα [Kd (nM)=27.38±3.8]. For reference 17β-estradiol binds ERα with a Kd (nM)=0.13 and ERβ with a Kd (nM)=0.15 in this system.

The study showed that only the S-equol enantiomer binds ER with sufficient affinity to have potential relevance to circulating equol levels reported in humans. Compared with 17β-estradiol the relative binding affinities of the S-equol and R-equol enantiomers for ERα were {fraction (1/49)} and {fraction (1/211)} that of 17β-estradiol, respectively. However, the S-equol enantiomer seems to be largely ERβ-selective with a relatively high affinity for ERβ, while the R-equol enantiomer binds with approximately {fraction (1/100)} the affinity of S-equol. The separate and associated determination that exclusively S-equol is found in human plasma and urine is significant in view of the specificity in binding of the two enantiomers.

Experiment 2. Bioavailability of R-equol.

20 mg of pure R-equol was administered orally to a healthy adult after an overnight fast. Blood samples were collected at timed intervals over the next 24 hours and the plasma concentration of equol was determined by isotope dilution gas chromatography-mass spectrometry with selected ion monitoring.

Figure 2:
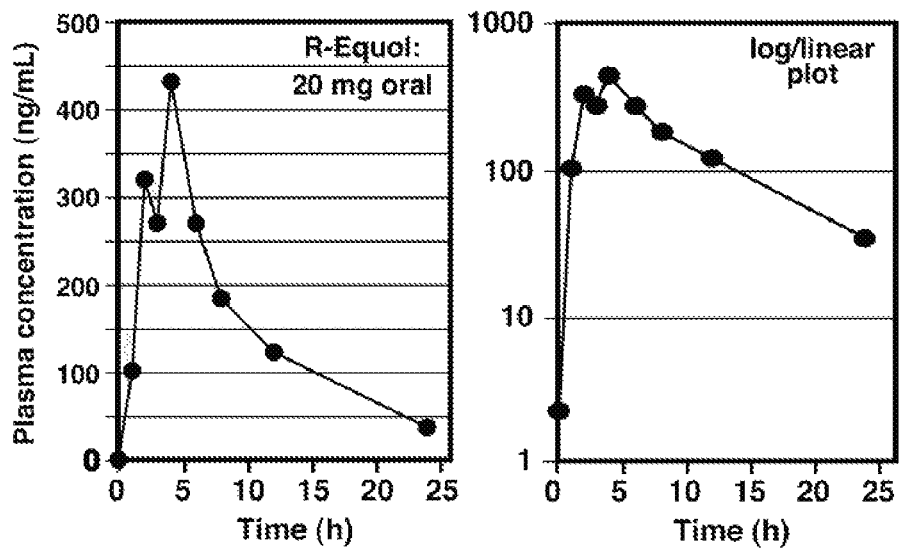
FIG. 2 shows an appearance/disappearance plot of R-equol in plasma after oral administration of R-equol to a healthy adult.

Rapid appearance of equol in the plasma with peak concentrations was observed after 8 hours. The terminal elimination half-life of R-equol was approximately 8 hours. Electrospray ionization mass spectrometry confirmed that the equol present in plasma was the R-equol enantiomer (PCT Patent Publication WO04-009035), thereby establishing that it is stable and does not undergo any racemization or further biotransformation in the intestine. FIG. 2 shows a plasma appearance/disappearance plot of R-equol. These results establish that R-equol, if administered as a pharmacologic or nutraceutical preparation, is bioavailable. Similar results have been obtained where S-equol was administered orally to a healthy adult.

EXAMPLES

The following examples demonstrate the use of the invention, and the benefits that are derived from it. In order to demonstrate the efficacy of the invention, the following protocols are used, and will be referred to in the examples that follow:

Protocols Used in Examples of the Invention

1. Preparation of Test Material Stock Solutions

Approximately 20 to 40 mg of the test material was weighed into pre-tared sterile glass vials and the precise weight was recorded. Vehicle volume was then calculated to give a 50% w/v solution, and the vehicle was added. Two different vehicles were used, as indicated in Examples. DMSO vehicle was prepared from 100% DMSO (EMD Biosciences Cat. #MX1458-6, Lot #42364321). Transcutol vehicle was prepared from 100% transcutol (Gattefosse a.s.a., Cedex, France). Samples were then vortexed vigorously until the dry powder was visually brought into solution. In some cases, samples need to be briefly warmed to 37° C. Stock solution aliquots can be frozen in small aliquots and maintained at approximately −20° C., or used immediately after preparation. Racemic mixtures of equol were prepared for testing at concentrations of 0 (control), 0.3, 1.0, and 5.0%. A positive control was prepared using ascorbic acid at a concentration of 50 μg/ml in DMEM/F-12. After stock solutions were diluted for use they were then discarded.

2. MTT Assay

MTT Assay was performed to determine toxicity of equol in tissue culture. Measurement of cell viability and proliferation forms the basis for numerous in vitro assays of a cell population's response to external factors. The reduction of tetrazolium salts is widely accepted as a reliable way to examine cell proliferation. The MTT assay is a calorimetric analysis of the metabolic activity of the cell (ATCC; Gaithersberg Md.; Catalogue #30-1010K). The yellow tetrazolium MTT (3-(4,5-dimethylthiazolyl-2)-2,5-diphenyltetrazolium bromide) is reduced by metabolically active cells to generate reducing equivalents such as NADH and NADPH. The resulting intracellular purple formazan can be solubilized and quantified by spectrophotometric means. The MTT Cell Proliferation Assay measures the cell proliferation rate and conversely, when metabolic events lead to apoptosis or necrosis, the reduction in cell viability. A linear relationship between cell number and signal produced is established, thus allowing an accurate quantification of changes in the rate of cell proliferation. In some cases or experiments, the results of the MTT Assay will be used to normalize the results of the Procollagen Type I C Peptide Assay.

A compatibility test was carried out with the test material(s) used in the test system. An aliquot of each test material was mixed with an equal volume of 2 mg/ml MTT solution, in a glass test tube. Tubes were capped and incubated in the dark at room temperature for approximately 2 hours unless conversion occurs sooner. Evidence of a color change to purple indicated that the test material may spontaneously reduce MTT, resulting in a false reaction. If a color change was noticed, "blank tissue meshes" were run. These blanks were dosed with the same amount of test material as in the assay and run for the longest time point only. Background readings are subtracted from the respective test materials if any are observed.

3. Use of TestSkin in Tissue Culture

TestSkin II tissue was used to assess the ability of the test materials to either promote or inhibit collagen synthesis. This test was also used to assess the viability of the tissues after exposure to the test materials. TestSkin II consisted of a mechanically stable and physiologically functional skin construct that closely simulated the actual structure and biological response mechanism of living human skin. The tissue had both an epidermis and a dermis. The upper epidermal layer consisted of living human keratinocytes and has a well differentiated stratum corneum. The epidermis grows on a supporting dermal layer that consisted of a bovine collagen lattice interspersed with living human dermal fibroblasts that align the collagen into a dense matrix. TestSkin was used according to the following Tissue Culture Protocol TestSkin Tissue Culture Protocol, Day One:

Enough six-well plates were taken to complete the assay and placed under the hood. The package containing each plate was opened, the plate cover removed and turned upside down on the working surface. One Millicell per well was placed into each well of a six-well plate, along with 1 ml of DMEM/F-12. The plate cover was replaced and the six-well plate set aside until the TestSkin II unit was sectioned and ready for storage. To section the TestSkin II unit, the outer surface of the sealed pouch is wiped with 70% ethanol. The pouch was opened using sterile scissors and the tray containing the TestSkin II unit removed. The cover from the TestSkin II tray was removed and placed upside down on the working surface, so that the inside of the cover remained sterile. The TestSkin II transwell was removed by using sterile forceps and placed on the inside of the cover. To section the TestSkin II unit, a sterile biopsy punch (8 mm) was used. The punch was placed on the surface of the TestSkin II unit and slowly pressed down and twisted simultaneously. The punch was rotated back and forth approximately ¼ turn while sufficient pressure was applied to cut through both the skin and the polycarbonate membrane. The punch was not twisted completely around, as this tends to rip the skin. When the individual section was separated from the rest of the skin, it was removed with sterile needle nose forceps; only the edge of the section was grasped, and care was taken not to pinch or fold the section. The section was carefully placed dermis side down onto the Millicell, ensuring that it lied flat with no air bubbles between the bottom of the Millicell and the skin. It was helpful for one edge to be placed down first and the remaining portion slowly lowered so that no air bubbles formed. The epidermal surface remained facing up and the polycarbonate membrane with the dermal surface lied against the Millicell. This procedure was repeated until the correct number of sections have been separated and placed within the Millicells of the six-well plate. Once the sectioning was complete, the cover was placed back onto the plate and the plate was placed into an incubator at approximately 37±2° C. and 5±1% $CO_2$ for overnight (16-24 hours).

TestSkin Tissue Culture Protocol, Day Two:

The media in each well was aspirated and replaced with 1 ml fresh DMEM/F-12 media. For each treatment group (negative control, positive control, and test materials), 10 µL of material was placed onto tissues and covered with a dosing pad. The tissues were placed back into the incubator at approximately 37±2° C. and 5±1% $CO_2$ for approximately 48 hours.

TestSkin Tissue Culture Protocol, Day Three:

All test samples were dosed topically again with 10 µL of each treatment per tissue. The tissues were placed back into the incubator at approximately 37±2° C. and 5±1% $CO_2$ for approximately 24 hours.

TestSkin Tissue Culture Protocol, Day Four:

The media from each well was removed and frozen for subsequent procollagen assays. The MTT assay was performed immediately on three of the four tissue samples in each treatment set. The fourth tissue from each treatment group was fixed in formalin, paraffin-embedded, sectioned, and subjected to histological staining. The histology slides were examined by microscope for elastin and collagen analysis.

A 2 mg/ml MTT solution (enough for 2 mg/tissue) is made with DMEM/F-12 (pre-warmed to 37±2° C.). The MTT solution was mixed for 10-15 minutes at room temperature on a stir plate. The solution was then centrifuged for 5 minutes at 4000 rpm. The pellet was discarded and only the supernatant used. The MTT solution was added to the wells of a six-well plate (2 ml/well). The tissues were removed from the Millicell inserts and rinsed with at least 5 ml of PBS from a wash bottle over a beaker. The tissues were rinsed until all test material was removed. The tissues were then placed into the corresponding well of the six-well plate. The plates were incubated for approximately 2 hours at approximately 37±2° C. and 5±1% $CO_2$ on a shaker plate at 125 rpm. At the end of the 2 hr incubation, the MTT solution was removed and discarded. One ml of PBS was added to each well for 2 minutes twice. Each PBS wash was removed by aspiration.

After the MTT exposure, the tissues were incubated in a 600 µg/ml Thermolysin solution (DMEM/F-12 for a 2 ml total volume) for 30 minutes at 37±2° C. This incubation time was expected to be sufficient to allow for the separation of the dermal and epidermal layers of the tissue. The epidermis was expected to be floating on top of the dermis. The dermal portions of the tissue were placed into a separate set of 6-well plates. The MTT was extracted from both sets of plates with 1 ml per well of isopropyl alcohol. The plates were placed on a shaker plate for 1 hour. After isopropanol extraction, 200 µL of extract was transferred to the corresponding wells of a 96-well plate. The plate was read at 540 nm.

4. Human Dermal Fibroblast Tissue Culture Protocol

Primary human dermal fibroblasts from neonatal foreskin at passage 10-11 were seeded into 48 well plates at 2.5e4 cells/well/0.5 mls medium, which consisted of DMEM (MediaTech, Cat. #10-017-CV, Lot #10017103) with 1× non-essential amino acids (HyClone Cat. #SH30238.01, Lot #AMC15759), 1× antibiotic/antimycotic (Sigma Cat. # A5955, Lot#13K2363) and 2% bovine calf serum (HyClone Cat. #SH30072.03, Lot #ANF-18955). Samples from a previous lot of calf serum (Lot # AMM17780), were also used. Cells were cultured for approximately 16-24 hours in a 37° C., humidified incubator with 5% $CO_2$, then the medium was changed and equol, ascorbic acid (Sigma, Cat. #A4544, Lot#073K0139) or vehicle was added to media in the wells. Cells were cultured for approximately 48 hours in the presence of test or control materials.

5. Organotypic, Three-Dimensional Dermal Cultures

For the production of organotypic, three-dimensional (3D) cultures, dermal fibroblasts were seeded to nylon mesh and allowed to grow for approximately 8 weeks essentially as described (see Fleishmajer, *J Invest Dermatol*, 97:638-643, 1991; Contard, *Cell Tissue Res*, 273: 571-575, 1993 and Pinney, Liu, Sheeman and Mansbridge, *J Cell Physiology*, 183: 74-82, 2000). This in vitro model closely mimics the development of the dermis, offering a system for study with organotypic properties, such as the ability to support epidermal differentiation (see Slivka, *J Invest Dermatol*, 100: 40-46, 1993) and collagen fibrillogenesis (Contard, *Cell Tissue Res*, 273: 571-575, 1993). After 2 weeks all 3D cultures were supplemented with 20 µg/mL ascorbate while monolayer cultures did not. Otherwise, all materials and procedures were essentially equivalent between monolayer and 3D experiments.

To examine the effects of estrogenic test materials in an environment with undetectable levels of estrogenic activity, the 3D experiments were grown in phenol red-free medium for 3 weeks prior to addition of test materials, and were, therefore, never exposed to the phenol red dye.

6. Human Prostate Cancer Cell Cultures

Human prostate cancer cell line was obtained from ATCC (ATCC # CRL-1740, LNCAP-FGC) and was cultured in a 37° C., humidified incubator with 5% $CO_2$, in RPMI Medium (Sigma Cat. # R-8758) with 5% fetal bovine serum (Hyclone Cat. # SH30088.03, Lot number APC20780) and 5 mM Hepes (Sigma Cat. H-0887), 1× antibiotic/antimycotic (Sigma Cat. # A5955). Cells were expanded in T-150 flasks for three passages until cryopreservation and storage in liquid nitrogen in RPMI medium with 10% FBS and 10% DMSO as cryopreservative. A cryovial was then thawed in a 37° C. water bath, expanded again one or two passages, and then plated at 10,000 cells per 96 well in 0.2 mls medium in 96 well plates in RPMI 5% FBS medium. After approximately 48 hours, the medium was changed to phenol red-free DMEM/F12 (Gibco Cat. #21041-025) with 2% FBS and 1× antibiotic/antimycotic and test materials and DMSO/vehicle controls were added to the appropriate concentration from 10× stocks. Cells were cultured for approximately 48 hours in the presence of test materials and controls prior to removal of medium supernatants for prostate specific antigen (PSA) ELISA.

7. Collagen Type I C-Propeptide ELISA

Collagens (types I, II, III, IV, and V) were synthesized as precursor molecules called procollagens. These contain additional peptide sequences called propeptides that facilitate the winding of procollagen molecules into a triple-helical conformation within the endoplasmic reticulum. The propeptides are cleaved off from the collagen triple helix molecule during its secretion, after which, the triple helix collagens polymerize into extracellular collagen fibrils. Thus, the amount of the free propeptides reflects stoichiometrically the amount of collagen molecules synthesized (Takara Biomedicals, Collagen Type I C-Propeptide Kit).

Dermal fibroblasts synthesized primarily type I collagen, and the cleavage of the C-terminal propeptide was required for deposition into fibrils within the extracellular matrix. This propeptide can be measured using antisera which do not recognize the unprocessed form in cell culture supernatants, and is also used clinically as a measure of fibrosis in patient sera. The amount of cleaved propeptide is directly proportional to the amount of type I collagen deposited, and can be precisely quantified using purified standards and a commercial ELISA kit (Takara Mirus, Inc., Cat. #TAK-MK-101).

After 48 hours in the presence of test materials or controls, culture medium supernatants were removed and immediately analyzed using the ELISA kit according to manufacturer's instructions using a Molecular Devices Vmax plate 96 well plate reader and SoftMax software. Since ascorbic acid (ascorbate, Sigma Cat. #A4544, Lot #073K0139) is known to stimulate collagen deposition, it was used as a positive control, and added to media in a final concentration of 20 µg/ml. Vehicle-treated media or media alone was used as a negative or blank control.

Supernatants or media from tissue culture were collected from culture plates or wells. ample supernatants were spun in a centrifuge at 2000-3000 rpm for 5-10 minutes and collagen Type I C-propeptide was quantitated. The pellet was not used in the study. The preparation of the assay solutions was as follows:

Standard Solution (640 no PIP/mi):

The standard was rehydrated with 1 ml of distilled water and mixed slowly by rolling on the countertop intermittently for approximately 10 minutes. The standards were made as shown in TABLE 1. The standard solution was stable for 1 week at 4° C. The standards were tested in duplicate.

TABLE 1

Standard Solutions for Procollagen Type I C-Peptide

| | Standard Assay Solutions | | | | | | |
|---|---|---|---|---|---|---|---|
| Final Conc. (ng/ml) | 0 | 10 | 20 | 40 | 80 | 160 | 320 | 640 |
| Maintenance Media (µl) | 400 | 394 | 388 | 375 | 350 | 300 | 200 | 0 |
| Standard Solution (µl) | 0 | 6 | 12 | 25 | 50 | 100 | 200 | 400 |

Stop Solution (1N $H_2SO_4$):

5.8 ml of concentrated $H_2SO_4$ was carefully added to 180 ml of distilled water. Distilled water was added to give a final volume of 200 ml. The solution was mixed well. This solution can be stored at 2-26° C. for up to 6 months.

Antibody-POD Conjugate Solution:

The contents of Vial 1 were dissolved in 11 ml of distilled water and mixed gently by rolling on the countertop. The vial was wrapped in foil as it is light sensitive. The solution was mixed slowly for approximately 10 minutes and foam formation was avoided. This solution was prepared directly before use and transferred immediately to the microtiter plate. Aliquots of 100 µl of antibody-POD Conjugate Solution were pipetted into the standard wells and the sample wells. The standard and the samples (20 µl of each) were pipetted into their corresponding wells. The microtiter plate was mixed by gently tapping the side for 15 seconds, then was sealed with foil and incubated at 37° C. for approximately 3 hours. At the end of the incubation, the solutions were removed from each well by inverting the plate, and washing each well 4 times with approximately 400 µl of PBS. Between each wash, the microtiter plate was emptied by inverting it and tapping upside down on a paper towel to remove as much of the PBS as possible. Substrate solution (100 µl) was pipetted into each well. The plate was tapped gently for 15 seconds to mix, and incubated at room temperature (20-30° C.) for 15 minutes. Stop solution (100 µl) was pipetted into each well and the plate tapped gently to mix for 15 seconds. The absorbance of the samples was measured at 450 nm on the ELISA microplate reader.

Calculations and Data Analysis:

For the Collagen Type I C-Propeptide assay, if more than one reading per sample was taken, the readings for each sample were averaged. To derive the standard curve, the absorbance versus the PIP concentration in ng/ml for the standards was plotted using log-log scale. For the samples, the average absorbance value on the vertical axis was located and a horizontal line intersecting the standard curve was followed. At the point of intersection, the PIP concentration (ng/ml) was red from the horizontal axis. The procollagen values (ng) were normalized for variations in tissue size or makeup by dividing by the dermis MTT value, since the dennal layer of the tissue is responsible for collagen synthesis.

The mean OD value and standard deviation for all MTT (dermis+epidermis) replicate samples was calculated. The percent of viability was calculated by using the following equation:

Viability (%)=(Mean OD of Test Material/Mean OD of Negative Control)×100.

8. PSA ELISA

Tissue culture supernatants were diluted 10-fold in PBS and stored at −20° C., then thawed at room temperature prior to assaying. A commercial ELISA kit for free PSA (Bio-Quant, Cat. # BQ 067T) was utilized according to the manufacturer's instructions, and data was determined using a Molecular Devices Vmax 96 well plate reader and SoftMax software.

9. Intracellular FACS Analysis and Cell Cycle Determinations

Single-cell suspensions were produced by gently trypsinization of monolayers, or extensive digestion in 1 mg/ml collagenase from 3D cultures. A commercial kit was utilized for the preparation of cells for intracellular detection by flow cytometry (IntraCyte, Orion BioSolutions, Inc., Cat. # 01017) according to the manufacturer's instructions. In brief, cells were fixed with formaldehyde, permeabilized with non-ionic detergents, and non-specific protein binding was blocked. The following primary antibodies were used at 1-2 ug/ml: affinity-purified, anti-human collagen type I (Chemicon Inc., Cat. #AB758), affinity-purified anti-human type III collagen (Sothern Biotechnology Associates, Inc. Cat. # 1330-01), monoclonal anti-human elastin (Sigma, Inc., Cat. # E4013), polyclonal anti-human elastase (The Binding Site Inc., Cat. #PC052), and monoclonal anti-human MMP-3/ stromelysin-1 (Calbiochem Inc., Cat. #IM362). Negative controls included irrelevant immunoglobulins from the same species as each primary antibody and at the same concentration, as well as unstained cell, and cells without primary antibody. Primary antibody binding was detected using affinity-purified, species-specific, fluorochrome-conjugated secondary antibodies. For FACS analysis, a Coulter EPICS Elite cytometer equipped with 488 nm argon laser was used and approximately 20,000 cells per file were analyzed using Coulter ELITE software.

10. Ocular and Dermal Irritection Assay

The Ocular and Dermal Irritection assays are quantitative in vitro test methods that mimic acute ocular and dermal irritation tests. To perform the Ocular Irritection standardized assay, the test sample was applied to a synthetic biobarrier composed of a semi-permeable membrane. To perform the Dermal Irritection standardized assay, the test sample was applied to a similar synthetic biobarrier that was coated with a dye-containing keratin-collagen matrix. Following application, the sample was absorbed by and permeated through this synthetic biobarrier to gradually come into contact with a proprietary solution containing highly ordered globulins and glycoproteins. Reaction of the test sample with these proteins and macromolecular complexes promoted conformational changes that may be readily detected as an increase in the turbidity of the protein solution. With the Ocular Irritection test, turbidity may be detected spectrophotometrically at a wavelength of 405 nm. With the Dermal Irritection test, dye that has been dissociated from the biobarrier during transit of the applied sample may be detected spectrophotometrically at a wavelength of 450 nm.

The ocular irritancy potential of a test sample was expressed as an Irritection Draize Equivalent (IDE), whereas the dermal irritancy potential of a test sample was expressed as a Human Irritancy Equivalent (HIE) score. These scores are defined by comparing the increase in optical density ($OD_{405/450}$) produced by the test material to a standard curve that is constructed by measuring the increase in OD produced by a set of Calibration substances. These Calibrators were selected for use in these tests because their irritancy potential has been previously documented in a series of in vivo investigations. The predicted in vivo classification, based on these scoring systems, is shown in TABLES 2 and 3. In general, the program was designed to accept sample data as qualified if the following criteria were met: the OD values of Calibrators and internal Quality Control samples fell within previously specified ranges; sample blanks were less than 500 OD units; the net sample OD was greater than −15; and an Inhibition Check was negative.

TABLE 2

Relationship of Irritection Draize Equivalent (IDE) Score to Irritancy Classification for the Ocular Irritection Test Method.

| Irritection Draize Equivalent (IDE) Score | Predicted Ocular Irritancy Classification |
|---|---|
| 0.0-12.5 | Minimal Irritant |
| 12.5-30.0 | Mild Irritant |
| 30.0-51.0 | Moderate Irritant |
| 51.0-80.0 | Severe Irritant |

TABLE 3

Relationship of Human Irritancy Equivalent (HIE) Score to Irritancy Classification for the Dermal Irritection Test Method.

| Human Irritancy Equivalent (HIE) | Predicted Dermal Irritancy Classification |
|---|---|
| 0.00-0.90 | Non-Irritant |
| 0.90-1.20 | Non-Irritant/Irritant |
| 1.20-5.00 | Irritant |

11. Statistical Analyses

Where appropriate, data were analyzed by analysis of variance statistics (ANOVA) followed by Newman-Keuls post hoc tests. Significance was p<0.05. Curve fitting, scientific graphing, and analysis were completed using GraphPad Software (GraphPad Prism 3.0, San Diego, Calif.).

Example 1

This example demonstrated equol selectively binding in vitro to 5α-DHT.

Figure 3:
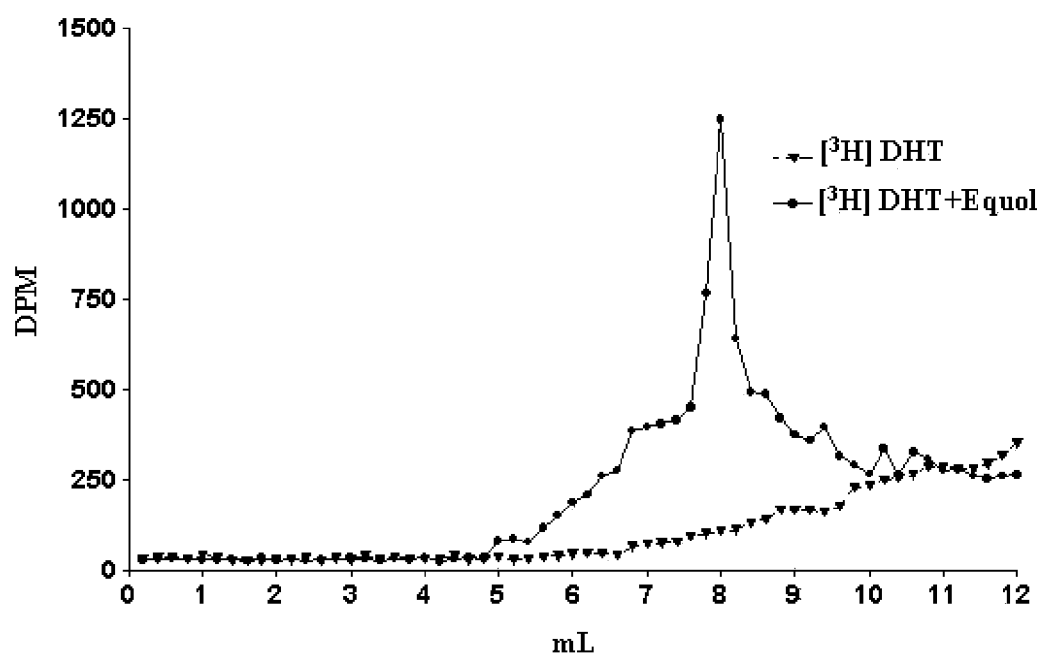
FIG. 3 shows a distinct peak in [$^3$H] 5α-DHT+equol but not [$^3$H] 5α-DHT alone.
Figure 5:
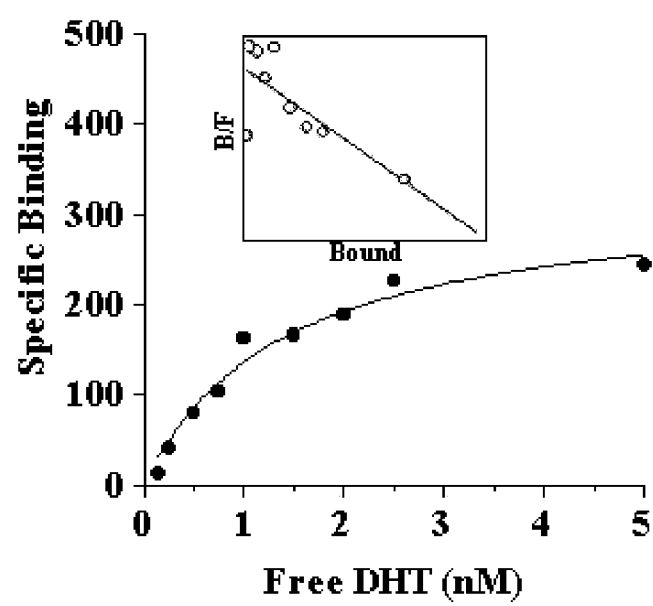
FIG. 5 shows the specific binding of equol to [$^3$H] 5α-DHT.
Figure 4A:
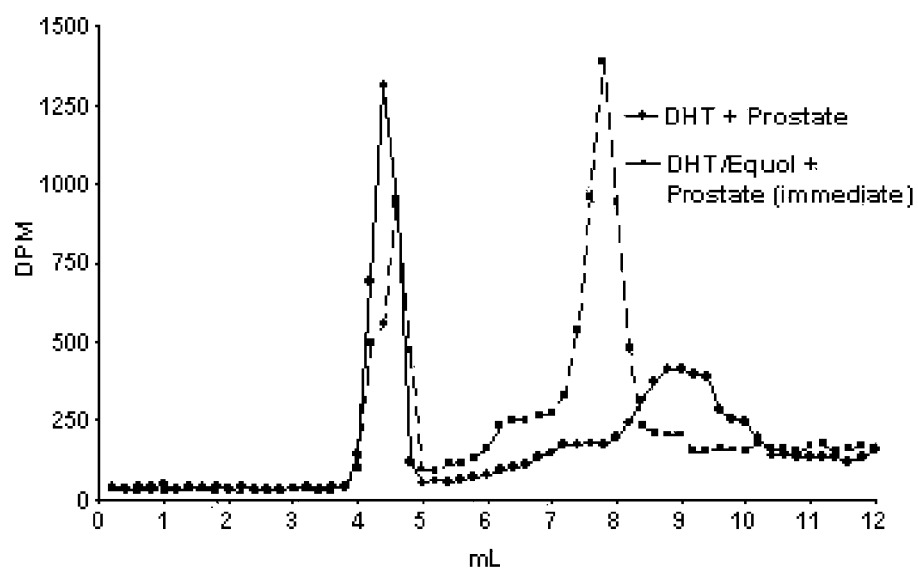
FIG. 4A shows two distinct peaks in [$^3$H] 5α-DHT+equol incubated with prostate (A).
Figure 4B:
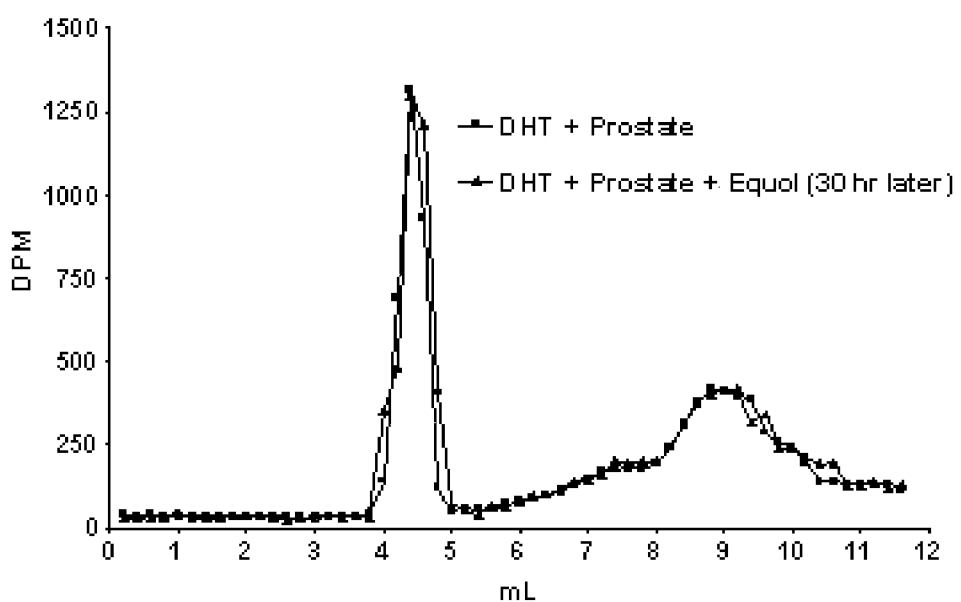
FIG. 4B shows only a single peak is present in [$^3$H] 5α-DHT incubated with prostate (B).

In initial binding competition studies conducted to determine and establish equol's binding affinity for AR, binding of [$^3$H] 5α-DHT was greater in the presence of equol than in its absence. Slight modifications in the protocol where AR was removed from the incubation tube (leaving only [$^3$H] 5α-DHT and equol) resulted in the elution of [$^3$H] 5α-DHT into the eluate containing [$^3$H] 5α-DHT reaction complex. Sephadex LH-20 columns of 30 cm were used in order to identify elution peaks establishing the binding of [$^3$H] 5α-DHT to equol. As shown in FIG. 3, a peak of [$^3$H] 5α-DHT is apparent in the elution fractions between 5 and 9 mL when the [$^3$H] 5α-DHT+equol column incubate was applied. This peak was not present when [$^3$H] 5α-DHT alone was applied to the column. Furthermore, when 5α-DHT or 5α-DHT+equol were incubated with prostate supernatant and then passed through the 30 cm column (FIG. 4A) two distinct binding peaks were identifiable. The first peak of [$^3$H] 5α-DHT represented that bound to the AR in prostate. This was found in the elution fractions between 4 and 5 ml. In addition there was a later peak (between 5 and 9 ml), consistent with the binding of [$^3$H] 5α-DHT to equol. However, when [$^3$H] 5α-DHT was allowed to incubate with the prostate supernatant for 36 hours (until equilibrium) prior to the introduction of equol there was no apparent binding of [$^3$H] 5α-DHT (FIG. 4B). Both [$^3$H] 5α-DHT and [$^3$H] 5α-DHT+equol (equol added 36 hours later) showed a single peak in the elution between 4 and 5 ml, suggesting that equol does not compete with 5α-DHT for the AR nor does it bind [$^3$H] 5α-DHT that was already bound to the receptor. Furthermore, it should be noted that the binding of equol to 5α-DHT appeared to be specific, since similar competition and binding studies have been conducted using other steroids such as [$^3$H]E2, [$^3$H]T, [$^3$H]DHEA, [$^3$H]CORT and [$^3$H]progesterone without any occurrences of significant binding to equol (data not shown). Saturation analysis of equol binding to [$^3$H] 5α-DHT showed an apparent Kd calculated at 1.32±0.4 nM (FIG. 5).

TABLE 4 shows 33 different steroid compounds that were tested in binding assays to determine equol's affinity for binding to each. While equol had modest affinity for 5α-reduced steroids, equol displayed the highest affinity for 5α-DHT and had no affinity for 5β-dihydrotestosterone (5β-DHT) or some of the most common natural sex steroids, such as: estradiol, estrone, estriol, progesterone or testosterone.

TABLE 4

Steroid Compounds used in Equol Binding Assays

| Chemical Name | Trivial Name |
|---|---|
| 4-ANDROSTEN-17β-OL-3-ONE | TESTOSTERONE |
| 5-ANDROSTEN-3β-OL-17-ONE | DHEA |
| 5α-ANDROSTAN-3α,17β-DIOL | 17β-DIHYDROANDROSTERONE |
| 5α-ANDROSTAN-3β,17α-DIOL | NA |
| 5α-ANDROSTAN-3β,17β-DIOL | NA |
| 5α-ANDROSTAN-3,17-DIONE | ANDROSTANEDIONE |
| 5α-ANDROSTAN-17β-OL-3-ONE | 5α-DHT |
| 5β-ANDROSTAN-17β-OL | NA |
| 5β-ANDROSTAN-17β-OL-3-ONE | 5β-DHT |
| 4-ANDROSTEN-3,17-DIONE | ANDROSTENEDIONE |
| 1,3,5(10)-ESTRATRIEN-3,17α∀-DIOL | EPIESTRADIOL |
| 1,3,5(10)-ESTRATRIEN-3,17β-DIOL | ESTRADIOL (E2) |

TABLE 4-continued

Steroid Compounds used in Equol Binding Assays

| Chemical Name | Trivial Name |
|---|---|
| 1,3,5(10)-ESTRATRIEN-3,16α,17β-TRIOL | ESTRIOL (E3) |
| 1,3,5(10)-ESTRATRIEN-3-OL-17-ONE | ESTRONE (E1) |
| 5α-ESTRAN-3,17-DIONE | 5α-DIHYDROANDROSTENEDIONE |
| 5-PREGNEN-3β-OL-20-ONE | PREGNENOLONE |
| 4-PREGNEN-3,20-DIONE | PROGESTERONE (P4) |
| 5α-PREGNAN-3α-OL-20-ONE | ALLOPREGNANOLONE |
| 5α-PREGNAN-11β,21-DIOL-3, 20-DIONE | ALLODIHYDROCOSTERONE |
| 5α-PREGNAN-3α,11β,21-TRIOL-20-ONE | ALLOTETRAHYDRO-CORTICOSTERONE |
| 5α-PREGNAN-3β,21β,21-TRIOL-20-ONE | EPIALLOTETRAHYDRO-CORTICOSTERONE |
| 5α-PREGNAN-3β,11β,17,21-TETROL-20-ONE | 3β, 5α-TETRAHYDROCORTISOL |
| 5α-PREGNAN-11β,17,21-TRIOL-3,20-DIONE | ALLODIHYDROCORTISOL |
| 5α-PREGNAN-17,21-DIOL-3,11,20-TRIONE | ALLODIHYDROCORTISONE |
| 5α-PREGNAN-3β-OL-20-ONE | 5α-DIHYDROPREGNANOLONE |
| 5α-PREGNAN-3, 20-DIONE | 5α-DIHYDROPROGESTERONE (5α-DHP) |
| 5β-PREGNAN-3α-OL-20-ONE | 3α-HYDROXY-5βTETRAHYDROPROGESTONE |
| 5β-PREGNAN-11β,21-DIOL-3,20-DIONE | 5β-DIHYDROCORTICOSTERONE |
| 5β-PREGNAN-3α,11β,21-TRIOL-20-ONE | TETRAHYDRO-CORTICOSTERONE |
| 5β-PREGNAN-3α,11β,17,21-TETROL-20-ONE | TETRAHYDRO-HYDROCORTISOL |
| 5β-PREGNAN-11β,17,21-TRIOL-3,20-DIONE | 5β-DIHYDROCORTISOL |
| 5β-PREGNAN-17,21-DIOL-3,11,20-TRIONE | 5β-DIHYDROCORTISONE |
| 5β-PREGNAN-3,20-DIONE | 5β-DIHYDROPROGESTERONE (5β-DHP) |

Example 2

Long-Evans male rats were raised on either a phytoestrogen-rich diet containing 600 micrograms of isoflavones per gram of diet or 600 ppm of isoflavones (referred to hereafter as the "Phyto-600" diet) or a diet containing very low levels of isoflavones (referred to hereafter as the 'Phyto-Free' diet; containing approximately 10 ppm of isoflavones).

To demonstrate that circulating isoflavone levels are different in Phyto-600- vs. Phyto-Free-fed male and female (75 day-old) rats, serum isoflavone levels were determined by GC/MS as previously performed and described (see methods in K. D. R. Setchell, *Am J Clin Nutr* 129:1333 S-1346S, 1998; and K. D. R. Setchell et al, *J Nutr* 132:3577-3584, 2002.). In each case for the different classifications of isoflavones Phyto-600-fed males displayed significantly higher isoflavone levels compared to Phyto-Free-fed values, shown in TABLE 5 as isoflavone concentrations in adult male and female rats. More importantly, equol levels in the Phyto-600-fed rats accounted for approximately 78% of the total phytoestrogen levels.

TABLE 5

| Isoflavone levels in male rats (ng/ml serum) | | | | |
|---|---|---|---|---|
| | Genistein | Daidzein | Equol | Total |
| Phyto-Free Diet | 9.6 ± 0.3 | 10.8 ± 0.6 | 23.2 ± 0.4 | 43.5 ± 1.0 |
| Phyto-600 Diet | 413 ± 67 | 394 ± 58 | 1,161 ± 325 | 1,967 ± 45 |

To determine if other metabolic hormones were altered by the diet treatments or by age, serum glucose and thyroid (T3) levels are assayed.

Figure 6:
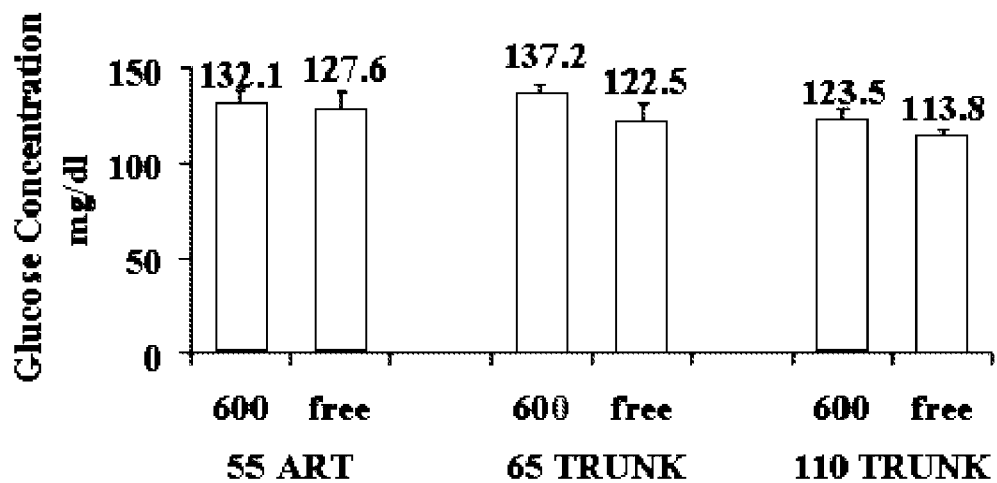
FIG. 6 shows serum glucose levels from male rats (non-fasting) fed either a Phyto-600 or Phyto-Free diet.
Figure 7:
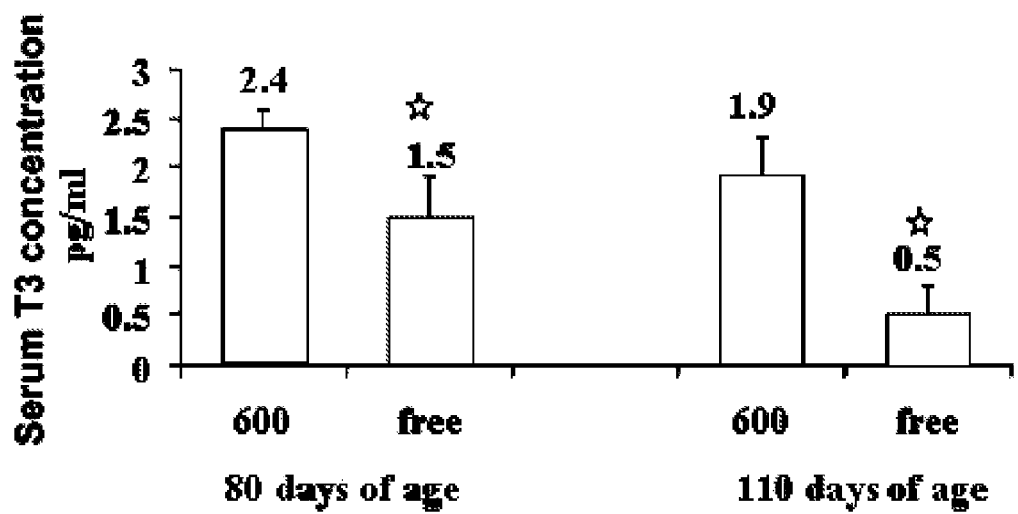
FIG. 7 shows thyroid (T3) serum levels in male rats fed either a Phyto-600 or Phyto-Free diet.

Glucose levels were slightly but not significantly higher in the Phyto-600-fed males compared to Phyto-Free-fed values, independent of age or source of the blood samples [either arterial (ART) or venous (TRUNK)], shown in FIG. 6. However, when T3 levels were quantified, there was a significant increase in T3 serum levels in 80 or 110 day-old male Long-Evans rats fed the Phyto-600 diet compared to Phyto-Free-fed animals, shown in FIG. 7. This demonstrated that thyroid levels were enhanced with soy consumption, consistent with anecdotal evidence of individuals that decreased their thyroid medication or went off of thyroid treatment completely with the consumption of soy based foods in their diets. This was also consistent with reports of a similar increase in T3 levels in humans following consumption of soy foods (Watanabe, S. et al, *Biofactors* 2000: 12:233-41 and Lephart, E. D. et al, *Nutrition Metab* (London) 2004:1:16).

Example 3

Figure 8:
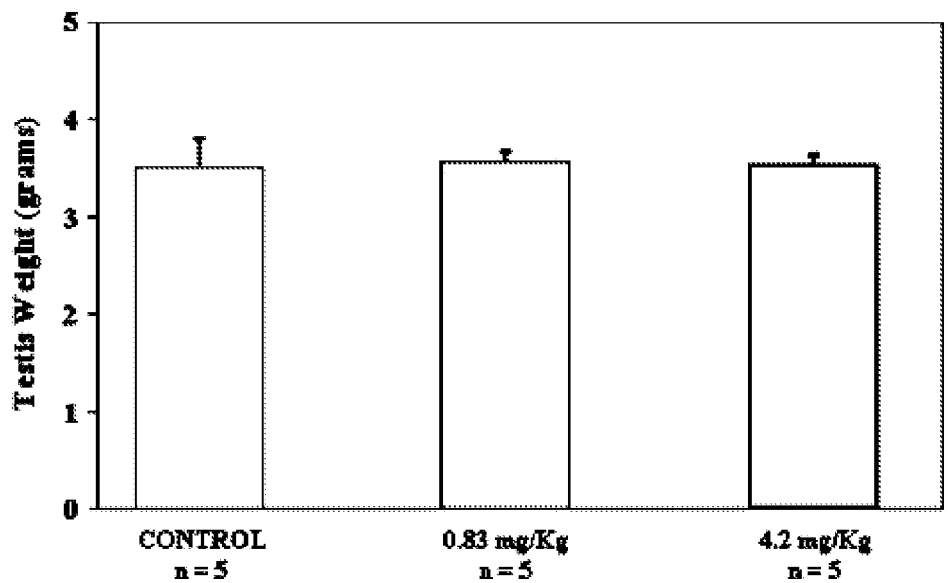
FIG. 8 shows testes weight from three groups of rats on a Phyto-Free diet 28 days after receiving equol or vehicle injections.

Prior to initiation of a Phyto-Free diet period, Male Long-Evans rats were fed a Phyto-200 diet, as described in previous examples. The rats were placed on a diet containing the Phyto-Free diet at approximately 52 days of age and randomly assigned to three groups. Beginning at 73 days of age, rats received daily subcutaneous 0.1 cc injections of vehicle (peanut oil), 1 milligram of a racemic mixture of equol in vehicle (0.83 mg/kg body weight/day), or 5 milligrams of a racemic mixture of equol in vehicle (4.2 mg/kg body weight/day) once every three days. To determine whether equol injections have an adverse effect on male reproductive organs, testis weights were quantified in these animals. There was no significant alterations in testes weight with the equol injections, with testicular weight essentially the same among the injection treatment groups, shown in FIG. 8.

Figure 9A:
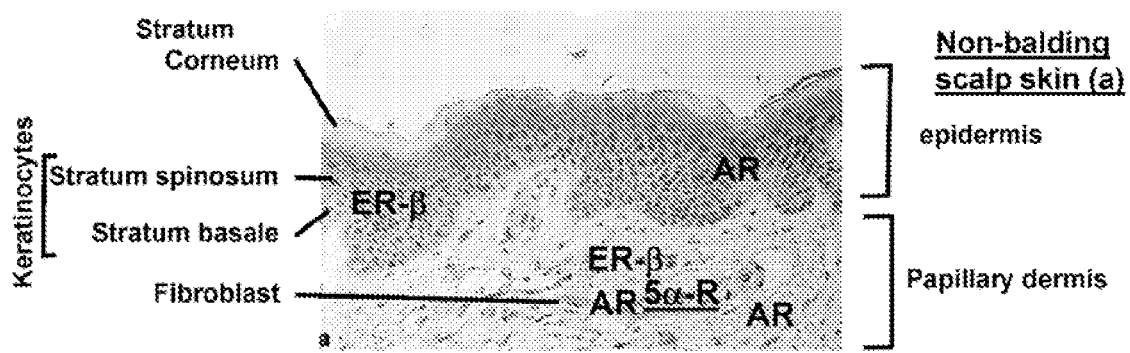
FIG. 9A shows the distribution of estrogen receptor beta (ER-β), 5α-reductase enzyme (5α-R) and androgen receptors (AR) in non-balding skin.
Figure 9B:
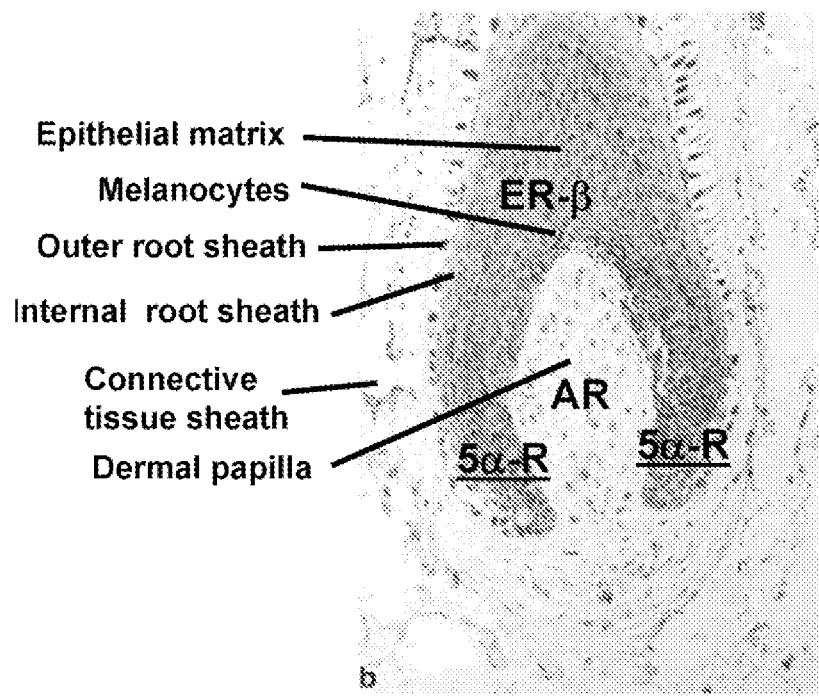
FIG. 9B shows the distribution of ER-β, 5α-R and AR in hair follicle bulb of human skin.
Figure 9C:
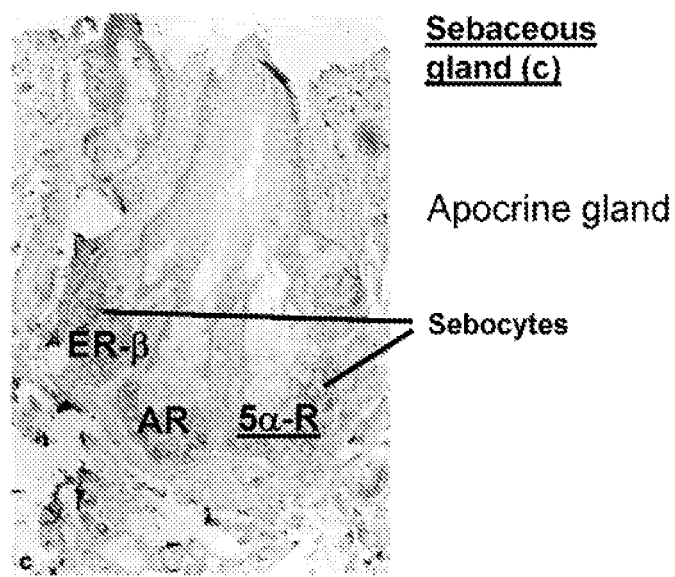
FIG. 9C shows the distribution of ER-β, 5α-R and AR in sebaceous gland of human skin.

FIG. 9 shows the distribution in human skin of estrogen receptor beta (ERβ), the 5α-reductase enzyme (5α-R) and androgen receptors (AR) in balding skin (FIG. 9A), hair follicle bulb (FIG. 9B) and sebaceous gland (FIG. 9C). Familiarity with the locations of these enzymes and receptors is important for discussion of the following examples.

Example 4

Figure 10:
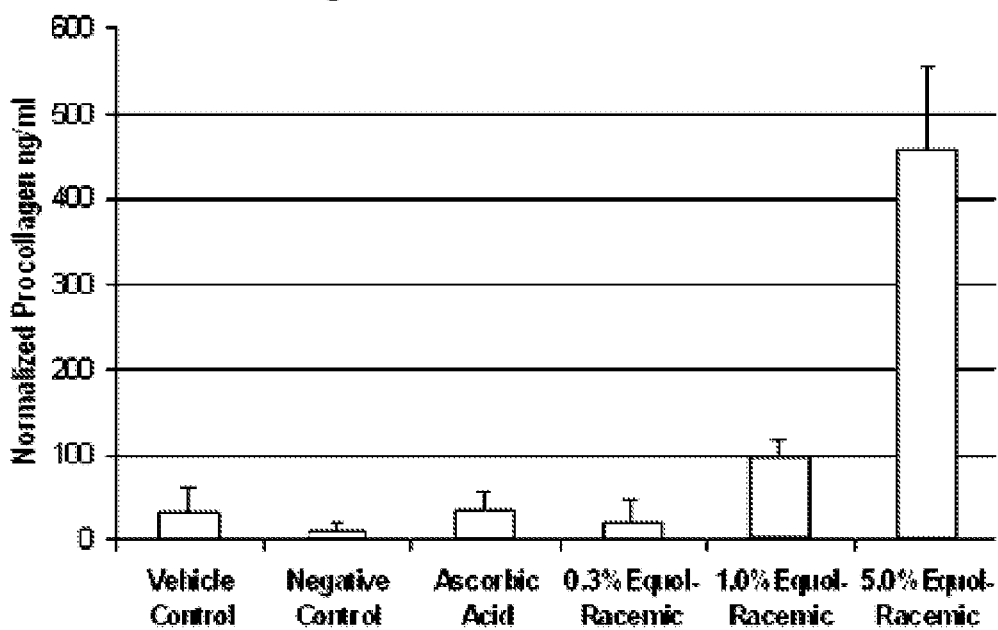
FIG. 10 shows procollagen synthesis in epidermis following incubation with control substances or equol (racemic mixture) added to tissue culture media.

The effect of equol on collagen synthesis in the TestSkin model was assessed. In examining the epidermal region only, vehicle, ascorbic acid, or 0.3% racemic equol had similar amounts of procollagen as measured by the Procollagen Type I C-Peptide-Assay, above, shown in FIG. 10. The negative control substance synthesized less procollagen compared to the control vehicle. However, a 1.0% concentration of racemic equol induced approximately 4 times as much procollagen synthesis, and 5.0% racemic equol induced an 18-fold increase versus vehicle control levels.

Figure 11:
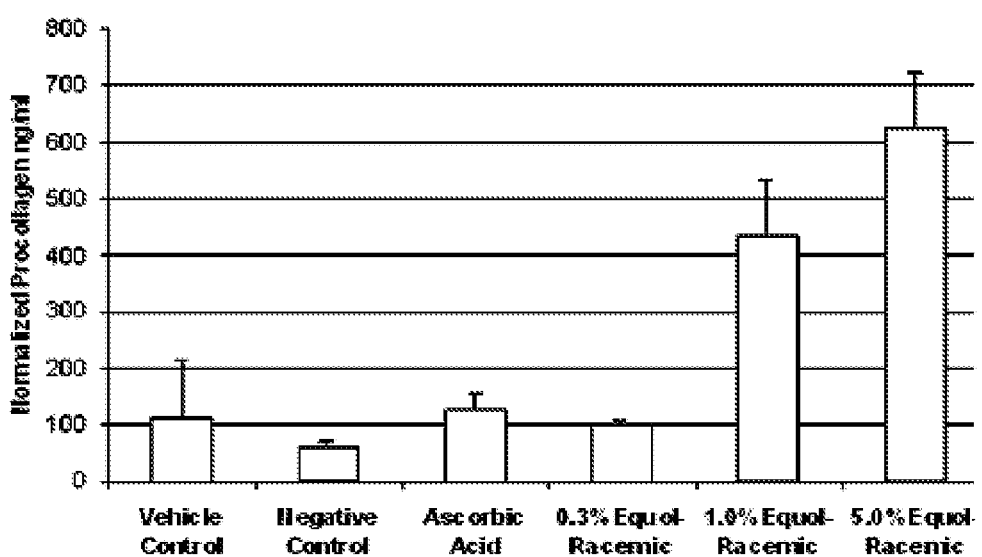
FIG. 11 shows averaged procollagen synthesis in epidermis plus dermis following incubation with control substances or equol (racemic mixture) added to tissue culture media.
Figure 12:
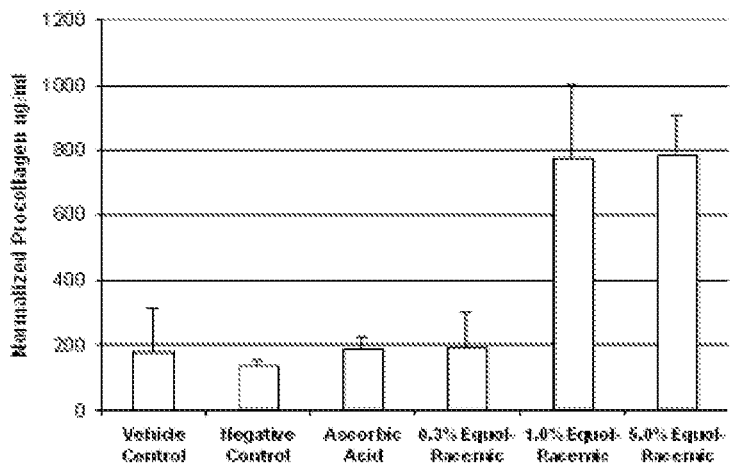
FIG. 12 shows procollagen synthesis in dermis following incubation with control substances or equol (racemic mixture) added to tissue culture media.

The normalized average of epidermal and dermal regions treated with vehicle, ascorbic acid, or 0.3% racemic equol also demonstrated similar amounts of procollagen, shown in FIG. 11, and samples incubated with the negative control substance synthesized less procollagen. Racemic equol at 1% concentration induced approximately 4 times as much procollagen synthesis, and a 5% concentration resulted in an approximate 6-fold increase. In examining the dermal region only vehicle, ascorbic acid, or 0.3% racemic equol had similar amounts of procollagen, shown in FIG. 12, and the negative control substance synthesized slightly less procollagen. Racemic equol at 1% and 5% concentrations induced approximately 4 times as much procollagen synthesized compared to vehicle control levels. Thus, using this artificial (in vitro) skin model, a threshold of 1% equol appeared to be sufficient to provide maximal stimulation of procollagen in the dermal region.

Example 5

This study evaluated the effects of racemic equol and 17β-Estradiol at 3 different concentrations (0.01%, 0.001% and 0.0001%) on primary human dermal fibroblast viability by MTT Assay, and collagen deposition by Collagen Type I C-propeptide ELISA.

Figure 13:
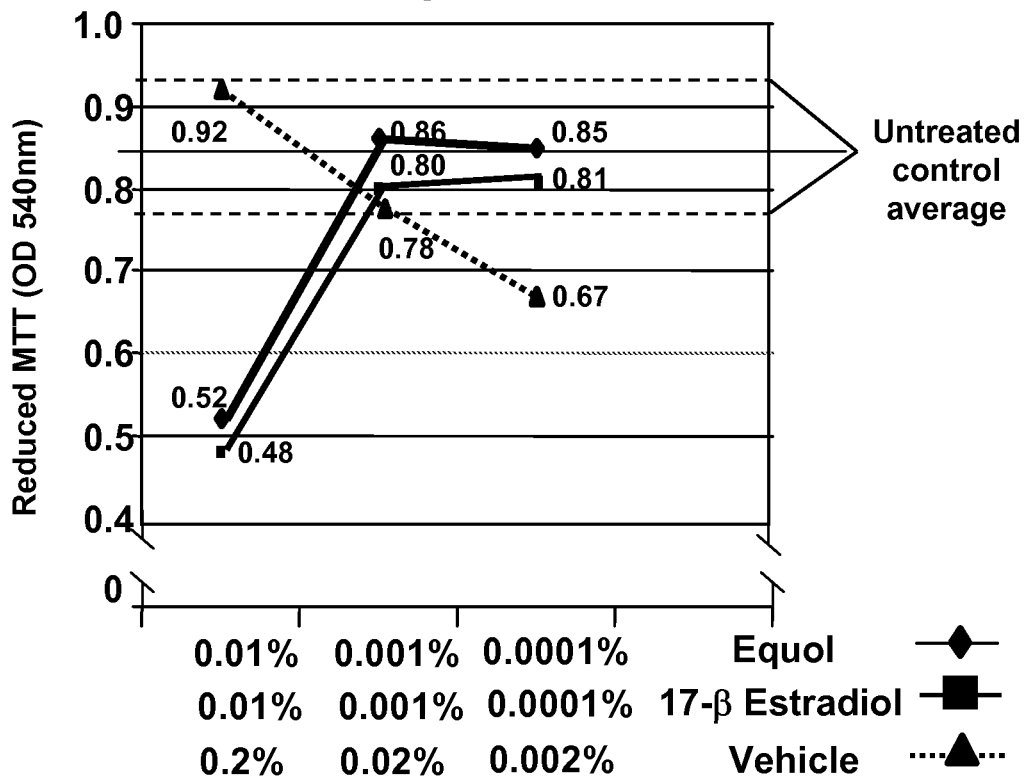
FIG. 13 shows metabolic activity, as measured by MTT Assay following incubation of human dermal monolayer fibroblasts with 0.01%, 0.001%, and 0.0001% equol, 0.01%, 0.001%, and 0.0001% 17β-estradiol, vehicle, or ascorbate added to the culture media.

Equol was tested against the natural steroid hormone, 17-β estradiol to determine cytotoxicity to human dermal monolayer fibroblasts by quantifying reduced MTT as described in the MTT Assay Protocol above (FIG. 13). The test materials, equol and 17-β estradiol were dissolved in dimethysulfoxide (DMSO), a common cell culture vehicle. The test materials were assayed at 0.01, 0.001 and 0.0001% equol in 0.2, 0.02 and 0.002% of DMSO as the vehicle. The range for untreated controls varied from 0.77 to 0.93 OD units. Over the range of concentrations tested equol was no more toxic to human dermal monolayer fibroblasts than 17-β estradiol. Additionally, at concentrations of 0.001% and 0.0001% of the test materials the reduced MTT values were within the range of the untreated controls, indicating that the cytotoxicity levels were equivalent to untreated control values. At the highest concentration of 0.01%, the cytotoxicity levels of the test materials were approximately 0.52 and 0.48 for equol and 17-β estradiol, respectively, which are acceptable results for in vitro assay conditions. Thus, at the concentrations tested, equol was not more toxic to human dermal monolayer fibroblasts compared to the natural steroid hormone, 17β estradiol.

Figure 14:
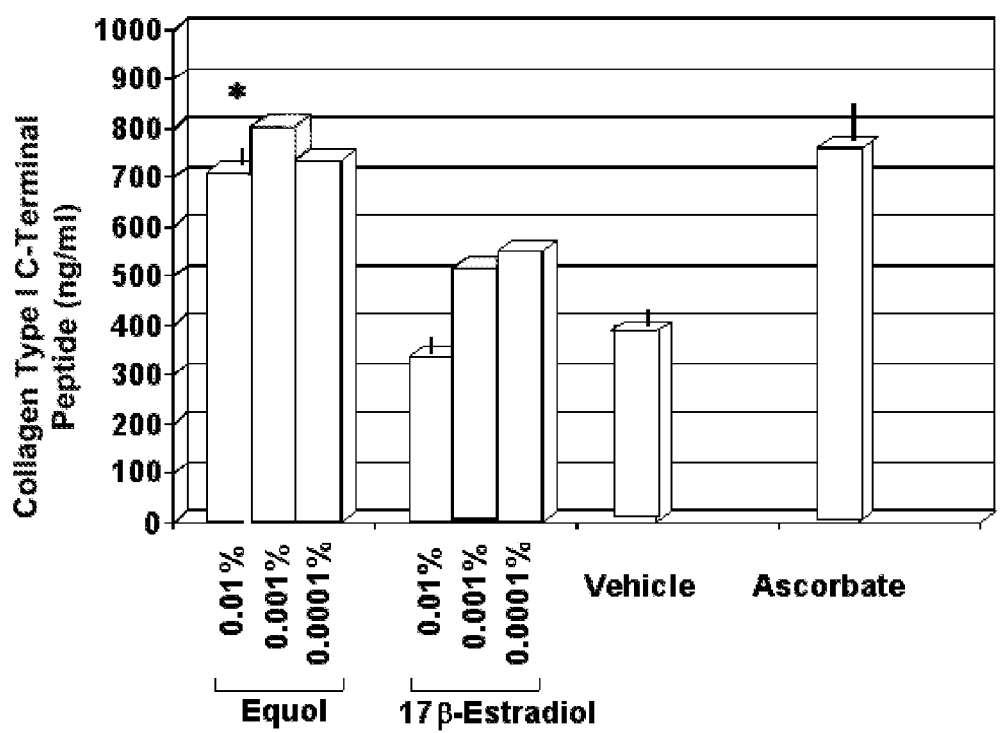
FIG. 14 shows collagen deposition by, as measured by Collagen Type I C-Terminal Propeptide ELISA, following incubation of human dermal monolayer fibroblasts with 0.01%, 0.001%, and 0.0001% equol, 0.01%, 0.001%, and 0.0001% 17β-estradiol, vehicle, or ascorbate added to the culture media.

Collagen deposition was quantified in human dermal monolayer fibroblast by ELISA (FIG. 14). The vehicle DMSO served as the negative control, while ascorbate without DMSO served as the positive control. When groups treated with 100 and 10 µg/ml equol were compared to the same concentrations of 17-β estradiol, significant 2.1-fold and 1.55-fold increases, respectively, in collagen deposition were observed. This example demonstrated that equol had significantly greater collagen stimulating properties compared to the natural steroid hormone, 17-β estradiol. The significant increase in collagen production in this human dermal monolayer fibroblast assay demonstrated that the stimulatory effect of equol on collagen provided an effective way to treat skin parameters such as mechanical, physical and photo-aging damage and the influence of biological aging on wrinkle formation in skin.

Example 6

Figure 15:
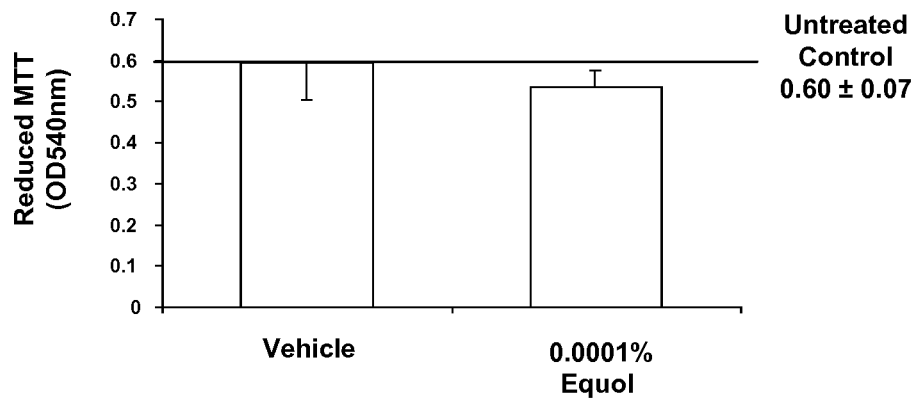
FIG. 15 shows metabolic activity, as measured by MTT Assay following incubation of human dermal monolayer fibroblasts with vehicle or 0.001% equol added to the culture media. Horizontal line indicates baseline as determined by untreated control cultures.

The effects of equol on skin, as assessed by collagen deposition were assessed by Procollagen Type I C-Peptide ELISA using human dermal monolayer fibroblasts in vitro. This study evaluated the effects of a commercially used skin penetrating agent, transcutol in delivering the test material equol in determining human dermal fibroblast viability by MTT Assay, and collagen deposition by Collagen Type I C-terminal Propeptide ELISA. Transcutol, or dipropylene glycol, has been proven safe and effective in the delivery of active ingredients of cosmetic applications for human skin health (Final report on the safety, assessment of butylenes glycol, hexylene glycol, ethoxydiglycol, and dipropylene glycol. *Journal of the American College of Toxicology*, Volume 4, Number 5, 1985, pages, Mary Ann Liebert, Inc. Publishers). When human dermal monolayer fibrobast cytotoxicity was examined, the equol treatment at 0.0001% (w/v of transcutol) was not significantly different compared to the 0.0002% transcutol vehicle or untreated controls (FIG. 15).

Figure 16:
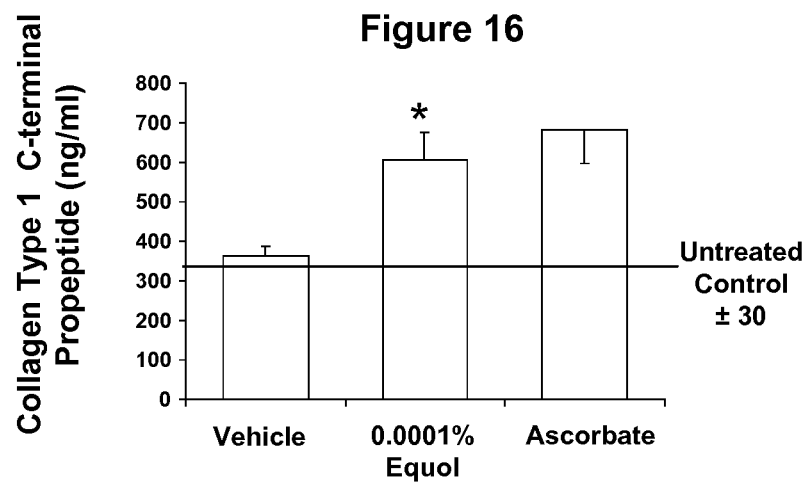
FIG. 16 collagen deposition by, as measured by Collagen Type I C-Terminal Propeptide ELISA, following incubation of human dermal monolayer fibroblasts with transcutol vehicle, 0.0001% equol, or ascorbate added to tissue culture media. Horizontal line indicates baseline as determined by untreated control cultures.

Next, equol was tested in the human dermal monolayer fibroblast assay to determine whether it could stimulate collagen deposition. As shown in FIG. 16, untreated control values were at 330±30 ng/ml (horizontal line) and this level was similar to that of 0.002% transcutol vehicle. However, 0.0001% equol significantly stimulated collagen deposition 1.8-fold above untreated control levels and 1.6-fold above the transcutol vehicle levels, demonstrating that transcutol is an effective method for the delivery of equol to human dermal fibroblasts. Furthermore, treatment with equol did not differ from the positive control treatment with ascorbate, suggesting that 0.0001% equol maximally stimulated collagen deposition in this in vitro human dermal monolayer fibroblast assay system. The significant stimulatory influence of equol on human dermal fibroblasts to significantly increase the deposition of collagen could address several important issues of human skin health such as applications of mechanical, physical and photo-aging damage, and the natural biological and chronological process of skin aging.

Example 7

This is an example of the ability of equol to bind and block 5α-DHT in vitro.

Figure 17:
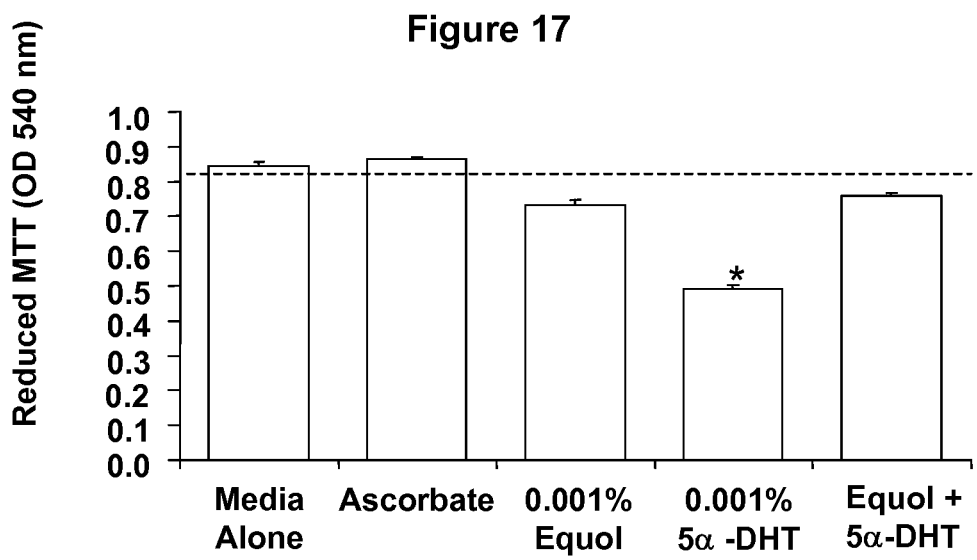
FIG. 17 shows metabolic activity, as measured by MTT Assay following incubation of human dermal monolayer fibroblasts with untreated media, ascorbate, 0.001% equol, 0.001% 5α-DHT, or a combination of 0.001% equol and 0.001% 5α-DHT added to tissue culture media. Horizontal dashed line indicates baseline as determined by untreated control cultures.
Figure 18:
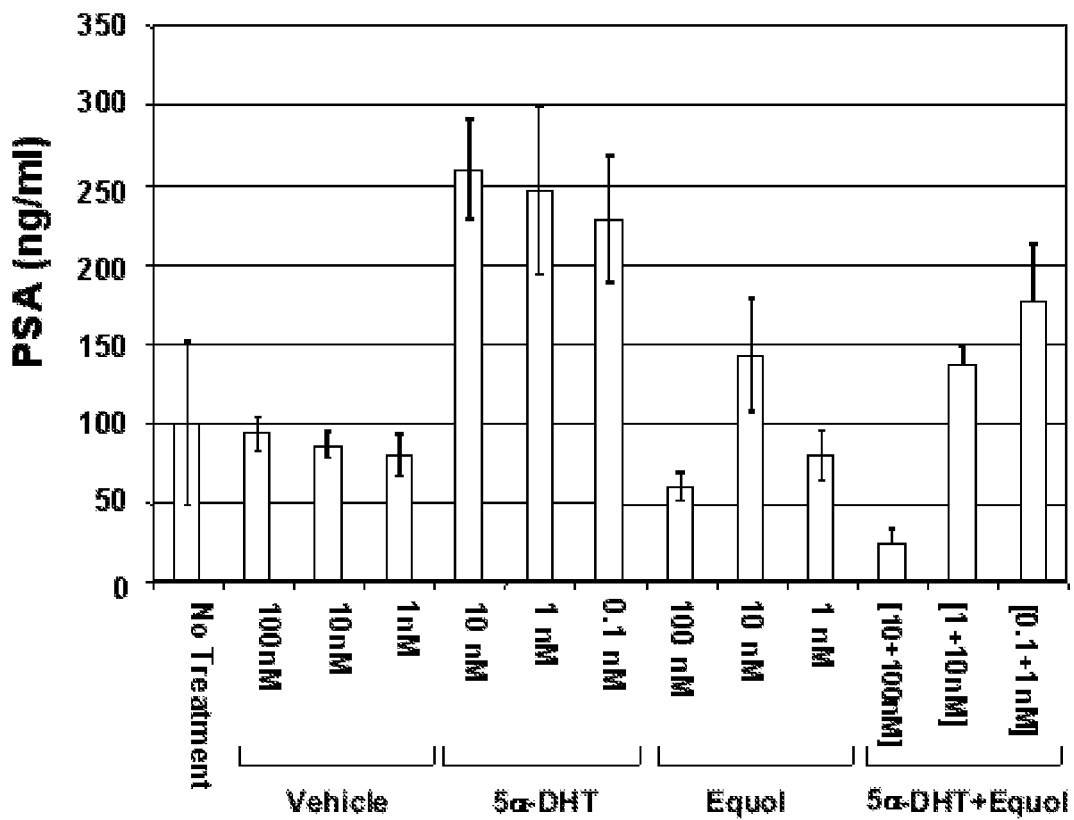
FIG. 18 shows prostate-specific antigen (PSA) levels secreted by prostate cancer cells following the incubation with vehicle, 10, 1, or 0.1 nM 5α-DHT, 100, 10, or 1 nM equol, or combinations of 5α-DHT and equol added to tissue culture media.

Cytotoxicity of equol on human dermal fibroblast cells was determined by MTT Assay (FIG. 17). The negative control consisted of tissue medium (DMEM/HAMS F-12) alone with no DMSO, which yielded cell viability levels of approximately 0.83. This negative control was similar to the positive control, ascorbate which contained no DMSO, at approximately 0.85.

Equol at 0.001% (or 10 micrograms/ml in 0.002% DMSO as the vehicle) displayed viability levels in the human dermal monolayer fibroblasts similar to that of the negative (no DMSO) and positive (ascorbate) controls. However, the potent natural androgen steroid hormone, 5α-DHT displayed the greatest cytotoxicity compared to all other treatment groups. When equol was added to the 5α-DHT samples in vitro, equol completely reversed the cytotoxic effects of 5α-DHT. This provided direct evidence that equol binds 5α-DHT in this in vitro human dermal monolayer fibroblast assay system and validates the in vivo evidence of equol biologically inactivating 5α-DHT's effects. Finally, by blocking the harmful effects of 5α-DHT in human dermal fibroblasts (cytotoxicity) and at the same time stimulating collagen deposition, this example demonstrated that equol has powerful effects on enhancing human skin health.

Example 8

This is an example of the effects of equol preventing the stimulatory effects of 5α-DHT in LNCAP prostate cancer cells in vitro from secreting prostate-specific antigen (PSA), a molecule known to be regulated by 5α-DHT, as measured by PSA ELISA.

Prostate cancer cells were treated with 0.1, 1 or 10 nM 5α-DHT, 1, and 100 nM equol or a combination of 5α-DHT with equol (0.1 nM 5α-DHT and 1 nM equol; 1 nM 5α-DHT and 10 nM equol or 10 nM 5α-DHT and 100 nM equol).

Cytotoxicity, as assessed by MTT Assay, did not influence PSA production by LNCAP prostate cancer cells. As shown in FIG. 18, 1, 10 or 100 nM Vehicle PSA levels did not differ from the No Treatment baseline. Treatment with 0.1, 1 or 10 nM 5α-DHT stimulated PSA secretion to maximal levels. PSA levels from cells treated with 1, 10, and 100 nM equol were below baseline, and did not differ significantly between groups. However, combinations of 10 nM 5α-DHT and 100 nM equol, as well as 1 nM 5α-DHT and 10 nM equol, abrogated the increase in PSA secretion, compared to 5α-DHT alone. Taken together with binding demonstrated in Example 1, this Example demonstrated that equol binds the 5α-DHT molecule and biologically inactivates it in skin and in the prostate.

Example 9

This is an example of equol preventing the stimulatory effects of 5α-DHT in vivo. Rats were injected with 1 mg of equol for 25 consecutive days, and serum 5α-DHT levels and prostate weights were measured since it is known that the prostate is stimulated by circulating 5α-DHT.

Adult (50 day-old) males (n=16), purchased from Charles River Laboratories (Wilmington, Mass., USA), were caged individually and housed in the Brigham Young University Vivarium and maintained on a 11-dark, 13-hour light schedule (lights on 0600-1900). Before purchase, the male animals were fed a diet containing approximately 200 ppm of isoflavones. At 50 days of age, upon arrival, the male rats were placed on a diet containing approximately 10 ppm of isoflavones; referred to hereafter as the Phyto-Free diet (Zeigler Bros., Gardnes, Pa., USA). All animals remained on the Phyto-free diet until 215 days of age. At 150 days of age the rats were divided into two groups (control or equol treatments) that were matched by age and body weight. Starting at 190 days of age the male rats received a daily subcutaneous 0.1 cc injection at the nape of the neck of vehicle (DMSO) or equol at a dose of approximately 2.5 mg/kg for 25 consecutive days.

The body weights for each group were recorded weekly starting a 150 days of age before the treatments were initiated, with weights obtained immediately before and after the treatments were administered. At 216 days of age the animals were anesthetized with Ketamine/acepromazine and blood was collected from the heart. Next the ventral prostate organ was dissected and weighed. The collected blood samples were centrifuged and serum was stored at −20° C. until time of assay.

Serum testosterone, 5α-DHT, and 17β-estradiol were quantified by radioimmunoassay (RIA) kits purchased from Diagnostic System Laboratories (Webster, Tex., USA). Luteininzing hormone (LH) was quantified by an assay utilizing standards from the National Institutes of Health (NIH) pituitary hormone program. The samples were run in duplicate for each RIA, with internal control samples. In all RIAs, the control values were within their normal respective ranges. The intra-assay coefficients of variance for the assays were: testosterone=6.0%; for 5α-dihydrotestosterone=8%, 17β-estradiol=5% and LH=9%.

When LH and testosterone were quantified between the treatment groups there were no significant differences in these hormone levels (TABLE 6). Since LH is the gonadotrophin regulating testosterone synthesis from Leydig cells in the testes, this was not a surprising result. However, equol-injected animals displayed an approximately 50% decrease in serum 5α-DHT compared to vehicle-injected animals. Finally, when 17β-estradiol levels were determined and there were no significant differences between the treatment groups. All hormone levels were within normal ranges of that expected for this strain, age and sex of rat. Prostate weights were significantly decreased by approximately 20% in the equol-injected males compared to control rats. This finding corresponded with the significant decrease in circulating 5α-DHT levels, which are known to regulate prostatic cell proliferation, and hence, prostate weight. Thus, this in vivo study demonstrated that equol can contact and biologically inactive the 5α-DHT molecule as shown by the significant decrease in 5α-DHT levels in blood and significantly reduced prostate weights of equol-treated male rats. Finally, the in vitro and in vivo studies reported above demonstrates that equol would be effective in treating skin and skin diseases/disorders that are regulated by the hormone 5α-DHT.

TABLE 6

Serum 5α-DHT Levels and Prostate Weight in Equol-Treated Male Rats.

| Parameter measured | Vehicle | Equol | Change |
|---|---|---|---|
| Prostate Weight (PW), mg | 535 ± 23 | 429 ± 30* | 20%↓ |
| PW/100 g Body Weight | 76 ± 4 | 61 ± 5* | 20%↓ |
| Luteinizing Hormone (LH), ng/ml | 1.6 ± 0.2 | 1.3 ± 0.1 | NSC |
| Serum Testosterone, ng/ml | 2.1 ± 0.4 | 2.3 ± 0.5 | NSC |
| Serum 5α-DHT, pg/ml | 100 ± 18 | 52 ± 5* | 50%↓ |
| Serum 17β-Estradiol, pg/ml | 3.4 ± 0.6 | 4.8 ± 0.7 | NSC | n = 8 animals per treatment group.
*= p < 0.05
NSC = no significant change

Example 10

This is an example of the effects of equol on stimulating collagen type I and III and elastin protein expression, inhibiting matrix metalloproteinase-3 (MMP-3) protein expression, inhibiting apoptosis, and stimulating cell proliferation in 3-dimensional (3-D) cultures of human dermal fibroblasts by intracellular fluorescence activated cell sorter (FACS) analysis.

In this study the effects of equol on the above parameters were compared to the natural female hormone, 17β-estradiol. Both equol and 17β-estradiol were used at 10 nM concentrations which corresponds to a normal range to study using in vitro experiments and represent an in vivo concentration range of circulating 0.1 to 1.0 nM 17β-estradiol and 1 nM 5α-DHT in women, and 3 nM 5α-DHT men (see Wilson J D et al, Williams Textbook of Endocrinology, $9^{th}$ ed. W. B. Saunders, Philadelphia, Pa., 1998).

Figure 19:
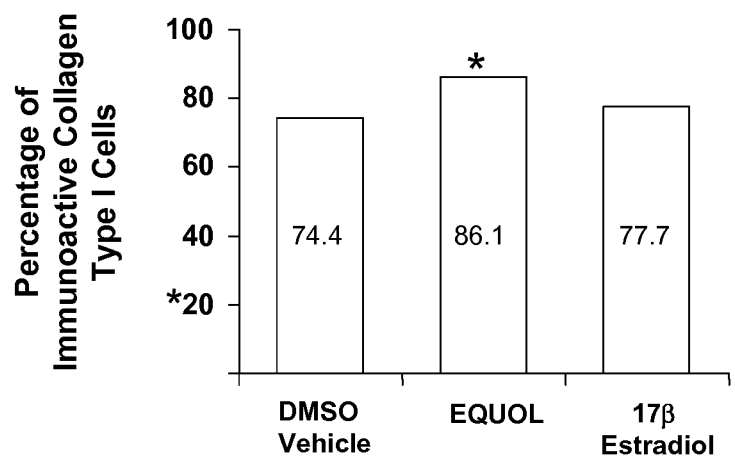
FIG. 19 shows fluorescence activated cell sorter (FACS) analysis of collagen type I protein expression in 3-dimensional (3-D) cultures of human dermal monolayer fibroblast following incubation with vehicle, 10 nM equol or 10 nM 17β-estradiol added to tissue culture media.
Figure 20:
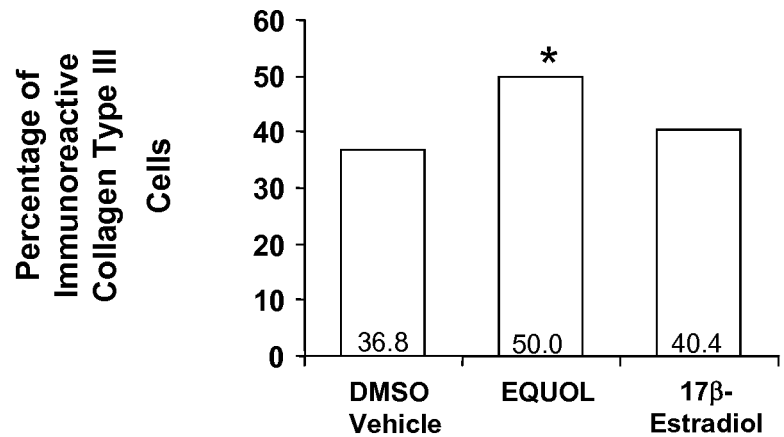
FIG. 20 shows FACS analysis of collagen type III protein expression in 3-D cultures of human dermal monolayer fibroblast following incubation with vehicle, 10 nM equol or 10 nM 17β-estradiol added to tissue culture media.

Using an organotypic three-dimensional dermal model, which closely resembles the intact dermis and allows for tissue-like deposition and maturation of the extracellular matrix by fibroblasts, equol significantly stimulated collagen type I (FIG. 19) and collagen type III (FIG. 20) compared to vehicle when assayed by FACS. These studies were performed partially as a control for the use of this methodology (i.e., FACS analysis) since equol has previously been shown to increase collagen deposition by dermal monolayer fibroblasts in culture.

Figure 21:
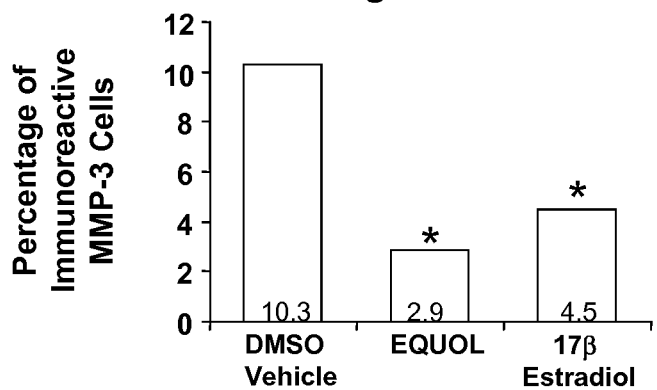
FIG. 21 shows FACS analysis of matrix metalloproteinase-3 (MMP-3) protein expression in 3-D cultures of human dermal monolayer fibroblast following incubation with vehicle, 10 nM equol or 10 nM 17β-estradiol added to tissue culture media.
Figure 22:
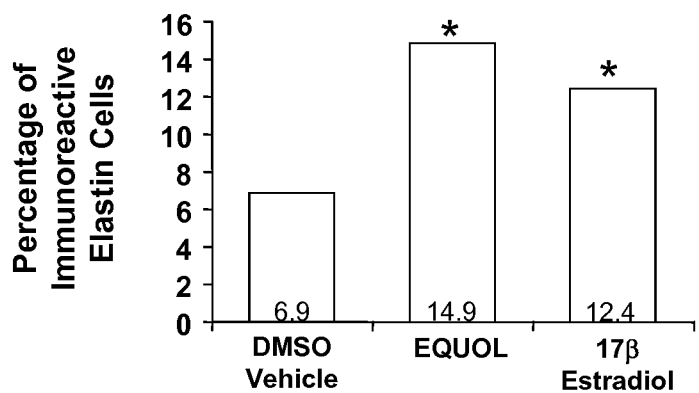
FIG. 22 shows FACS analysis of elastin protein expression in 3-D cultures of human dermal monolayer fibroblast following incubation with vehicle, 10 nM equol or 10 nM 17β-estradiol added to tissue culture media.

Only equol, but not 17β-estradiol, increased both collagen types I and III. Since the net deposition of extracellular matrix molecules was also affected by the presence and activity of matrix-degrading enzymes, the expression of MMP-3/stromelysin-1 by intracellular FACS was also measured (FIG. 21). MMP-3 is an important enzyme which can degrade collagen and elastin, as well as other extracellular matrix constituents. Both equol and 17β-estradiol reduced MMP-3 protein expression. However, equol significantly decreased the expression of MMP-3 by 3.6-fold vs. 2.3-fold for 17β-estradiol compared to vehicle. This indicated that equol is an effective agent for inhibiting the matrix-degrading enzyme that in turn would enhance the expression of collagen and elastin. Since elastin is an important extracellular matrix molecule, along with collagen in the maintenance of good skin health for the prevention and treatment of wrinkles, equol was tested against 17β-estradiol in the FACS analysis. In the 3-D human dermal fibroblast cultures, equol significantly stimulated elastin 2.2-fold over vehicle levels while 17β-estradiol stimulated elastin production by 1.8-fold vs. the control (FIG. 22).

Thus, equol significantly stimulated collagen type I, collagen type III and elastin protein expression while significantly decreasing the matrix-degrading enzyme MMP-3. As shown in FIG. 23, 17β-estradiol significantly increased the elastin-degrading elastase enzyme expression 1.9-fold vs. vehicle levels. However, equol was not different compared to the vehicle, demonstrating that equol promoted elastin protein expression without increasing degradation of elastin.

Further FACS analysis of the same 3-D human dermal fibroblast cultures was performed by staining the cells with propidium iodide (PI) (fluorescent DNA dye). The FACS analysis via PI-stained cells was able to detect by different markers the percentage of cells that were apoptotic (engaged in programmed-cell death) and the percentage of cycling human dermal fibroblasts in S- and G2M-phases of the cell cycle. FIG. 24 shows the cell cycle analysis for the percentage of apoptotic cells expressed in the 3-D cultures. There were no significant differences between the treatments (equol or 17β-estradiol) compared to vehicle. This demonstrated that equol or 17β-estradiol at 10 nM had no significant effect on apoptosis. However, the percentage of cycling human dermal fibroblasts in S- and G2M-phases of the cell cycle showed that equol, but not 17β-estradiol, significantly stimulated fibroblasts to proliferate at 1.5-fold compared to vehicle (FIG. 25). This data set demonstrated that equol stimulates human dermal fibroblasts to proliferate, which is consistent with increased collagen types I and III and elastin protein expression in the same human dermal fibroblast cells. Furthermore, these finding correspond with the doubling of collagen deposition in human dermal fibroblasts following the application of equol.

Example 11

This example demonstrates the effect of equol in regulating skin tail temperature.

Equol effects were tested by injecting 3 mg of equol for 5 consecutive days in adult male rats and quantifying skin tail temperatures at the end of the treatments. In this experiment rodent skin tail temperature was determined by quantifying skin temperature by sensor/radio telemetry. Male Long-Evans male rats were purchased from Charles Rivers Laboratories at 50 days of age. The animals were placed on a diet containing very low isoflavone levels (10-15 ppm of isoflavones per gram of diet) and allowed ad lib access to this diet and water throughout the experiment. At approximately 130 days of age the male rats were observed for sexual activity by mating with receptive females. All males used in this study were sexually active by mating and inseminated receptive females that in turn become pregnant and subsequently delivered normal size litters.

At approximately 160 days of age the male rats were matched by body weight and placed into either a control or equol treatment group. As this time the rats were handled for 5 to 10 minutes per day to habituate the animals to being handled. Handling consisted of placing the rat on the supine forearm surface of laboratory personnel. This handling protocol was continued each day for approximately 2 weeks or when the animal reached 174 days of age. At 175 days of age, the rats were handled as before, but 1-inch wide silk surgical tape was placed around the animal's tail approximately 1 inch from the base of the tail to simulate the placement of the temperature sensor/transponder. This handling/tape protocol took place daily from 175-180 days of age.

At 175 days of age, each animal received a 0.1 cc subcutaneous injection at the nape of the neck of either vehicle (DMSO), or a solution of 3 mg of equol. At the time the animals weighed approximately 700 grams, therefore the dose was about 4.3 mg/kg of equol per day. The treatment injections were given for 5 consecutive days.

Figure 26:
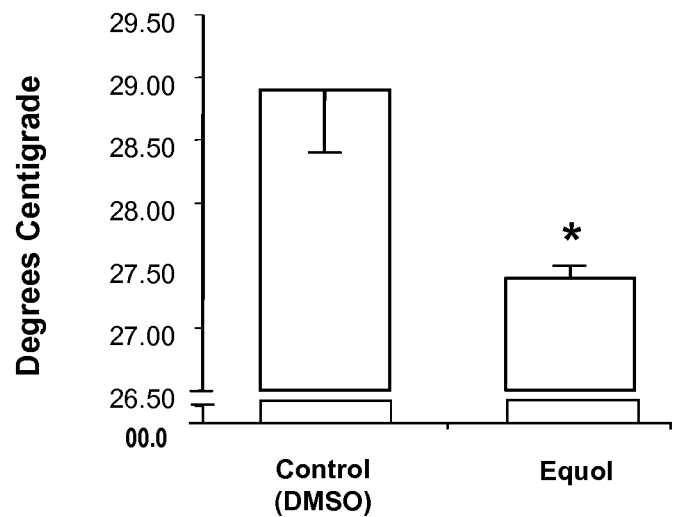
FIG. 26 shows the skin tail temperature of male rats after receiving vehicle or equol injections for 25 consecutive days.

On the $5^{th}$ day of the treatment injections (or 180 days of age) tail skin temperature was quantified by an electronic sensor/transponder taped to the base of the animal's tail. Thirty seconds after the sensor/transponder was taped to the tail the skin temperature was recorded by radiotelemetry (±0.1° C.). The same sensor/transponder was used for all of the animals in the two treatment groups in recording skin tail temperatures. The rats treated with equol had a 1.5° C. decrease in skin temperature, compared to control rats (FIG. 26). Control group, n=5; equol group, n=4, p<0.025. This finding suggested that equol can be used to treat hot flushes associated with perimenopause symptoms or in post-menopausal women.

Example 12

Figure 27:
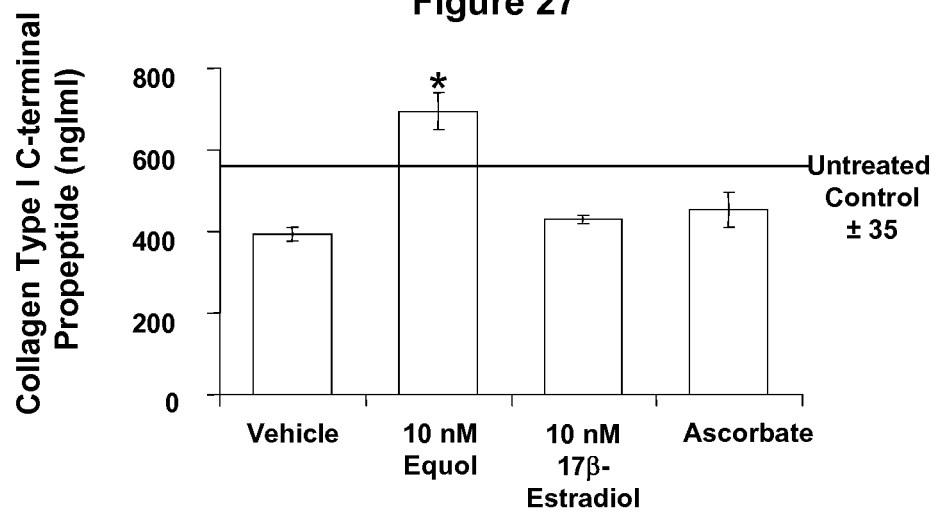
FIG. 27 shows the results of human dermal monolayer fibroblast collagen deposition measured by Collagen Type I C-Terminal Propeptide ELISA following incubation with vehicle, 10 nM equol, 10 nM 17β-estradiol, or ascorbate added to tissue culture media.

This example demonstrated the effects of equol on skin collagen deposition by measuring Collagen Type I C-Propeptide from human dermal monolayer fibroblasts in vitro treated with 10 nM equol or 10 nM 17β-estradiol as in the FACS analysis experiments. There was no cytotoxicity when 10 nM equol or 10 nM 17β-estradiol was added to the tissue cultures. Treatment with 10 nM of equol significantly stimulated collagen deposition 1-8-fold compared to vehicle (FIG. 27), while 17β-estradiol treatment was similar to that found with ascorbate treatment. This example demonstrated that 10 nM equol significantly can stimulate collagen deposition by human dermal fibroblasts.

Example 13

This is an example of the effects of vehicle (ethanol), equol-racemic or 99% S-equol as evaluated with the Irritection® Assay System in order to predict its potential to cause ocular and dermal irritation. To achieve this objective, standard volume-dependent dose-response studies were performed with the Ocular and Dermal Irritection test methods. The proprietary Ocular and Dermal Irritection assays are standardized and quantitative in vitro acute ocular and dermal irritation tests which utilize changes of relevant macromolecules to predict acute ocular and dermal irritancy of chemicals and chemical formulations. The Ocular and Dermal Irritection assay methods can be readily employed to evaluate multiple samples at varying volumes or concentrations and provide highly reproducible results. Thus, these tests serve as extremely useful screening tools that facilitate all stages of raw material selection, formulation development and final product selection.

Figure 28:
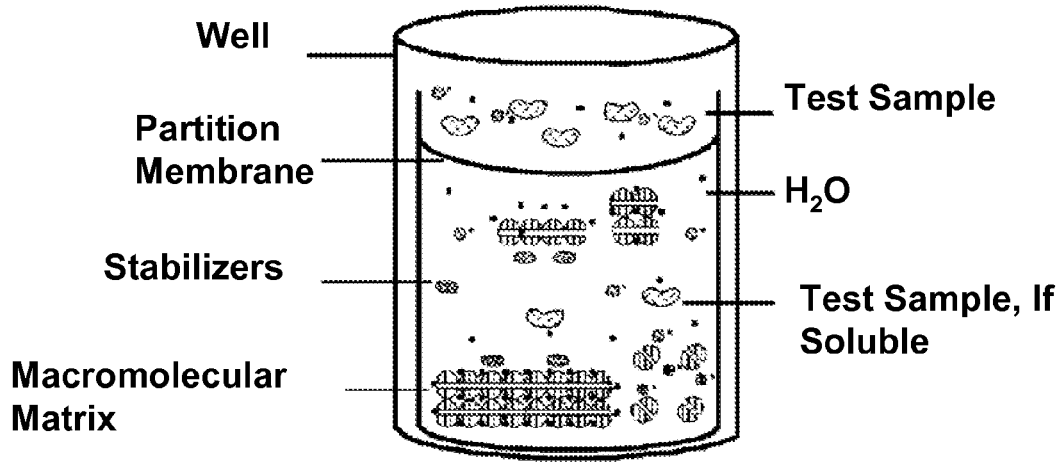
FIG. 28 shows the ocular irritection model for testing irritant characteristics of vehicle (ethanol), equol-racemic or S-equol.

The Ocular Irritection assay, depicted schematically in FIG. 28, provides significant advances over the in vivo Draize test method. The Draize eye irritation assay has been criticized because of the large variability of results obtained from different laboratories that have analyzed the same specimen.

Figure 29:
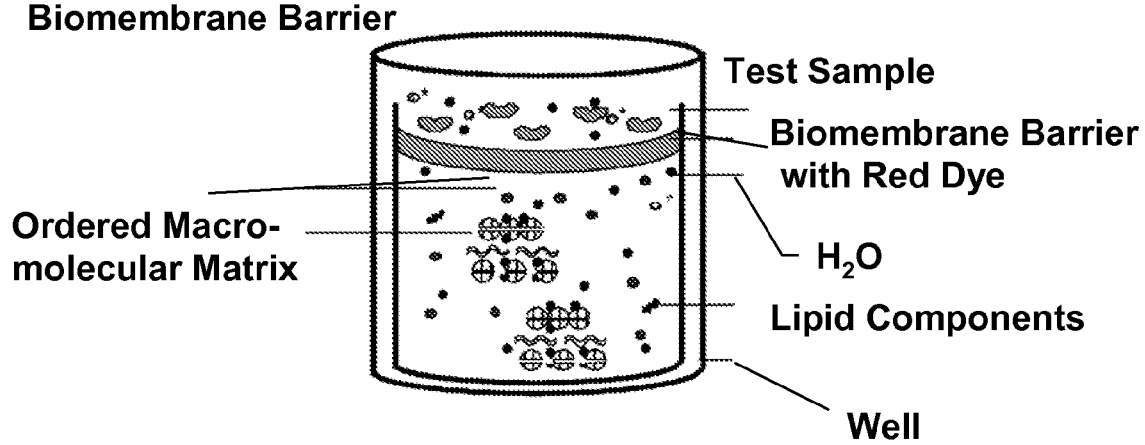
FIG. 29 shows the dermal irritection model for testing irritant characteristics of vehicle (ethanol), equol-racemic or S-equol.

The Dermal Irritection assay, depicted schematically in FIG. 29, is based on the principle that chemical compounds will promote measurable changes in target biomolecules and macromolecular structures. Previous studies have clearly demonstrated that the processes of protein denaturation and disaggregation that are induced in this in vitro assay mimic the effects that are produced when these types of irritants are applied to the skin. Consequently, this in vitro test may be employed to predict the in vivo toxic effects of chemicals and formulations.

The results of the analysis on 4% (v/v) ethanol in physiological buffered saline (PBS) vehicle, 4% (w/v) equol-racemic in vehicle and 4% (w/v) s-equol (99% purity) in vehicle are shown below. The results of the study indicate that the sample of vehicle was classified as a borderline minimal/mild ocular irritant with an IDE score of 12.6. A similar volume-dependent dose-response study was performed with the Dermal Irritection test method. The results demonstrated that the sample was predicted to be a non-irritant with a HIE score of 0.49. TABLES 7 and 8 present a summary of results for the vehicle.

TABLE 7

Ocular Irritection Results - Vehicle Only

| IVI Number | Sample Description | Dose | IDE Score | Predicted Ocular Irritancy Classification |
|---|---|---|---|---|
| E7184 | VEHICLE ONLY | 25 µl | 6.8 | Minimal Irritant |
| | | 50 µl | 8.7 | Minimal Irritant |
| | | 75 µl | 9.4 | Minimal Irritant |
| | | 100 µl | 10.6 | Minimal Irritant |
| | | 125 µl | 12.6[a] | Minimal/Mild Irritant |

[a]Maximum Qualified Score

TABLE 8

Summary of the Dermal Irritection Results - Vehicle Only

| IVI Number | Sample Description | Dose | HIE Score | Predicted Dermal Irritancy Classification |
|---|---|---|---|---|
| S4243 | VEHICLE ONLY | 25 µl | 0.25 | Non-Irritant |
| | | 50 µl | 0.32 | Non-Irritant |
| | | 75 µl | 0.41 | Non-Irritant |
| | | 100 µl | 0.44 | Non-Irritant |
| | | 125 µl | 0.49[a] | Non-Irritant |

[a]Maximum Qualified Score

A standard volume-dependent dose-response study was performed with the Ocular Irritection test method. The following volumes of neat sample were applied for analysis: 25, 50, 75, 100 and 125 µl. The results of the study indicated that the sample of equol racemic was classified as a mild ocular irritant with an IDE score of 14.2. A similar volume-dependent dose-response study was performed with the Dermal Irritection test method. The results demonstrated that the sample was predicted to be a non-irritant with a HIE score of 0.35. TABLES 9 and 10 present a summary of results for the 4% equol-racemic in vehicle.

TABLE 9

Ocular Irritection Results for 4% equol-racemic

| IVI Number | Sample Description | Dose | IDE Score | Predicted Ocular Irritancy Classification |
|---|---|---|---|---|
| E7185 | RACMIC EQUOL | 25 µl | 7.0 | Minimal Irritant |
| | | 50 µl | 9.1 | Minimal Irritant |
| | | 75 µl | 11.9 | Minimal/Mild Irritant |
| | | 100 µl | 12.8 | Minimal/Mild Irritant |
| | | 125 µl | 14.2[a] | Mild Irritant |

[a]Maximum Qualified Score

TABLE 10

Dermal Irritection Results for 4% equol-racemic

| IVI Number | Sample Description | Dose | HIE Score | Predicted Dermal Irritancy Classification |
|---|---|---|---|---|
| S4244 | RACEMIC EQUOL | 25 µl | 0.07 | Non-Irritant |
| | | 50 µl | 0.15 | Non-Irritant |
| | | 75 µl | 0.24 | Non-Irritant |
| | | 100 µl | 0.30 | Non-Irritant |
| | | 125 µl | 0.35[a] | Non-Irritant |

[a]Maximum Qualified Score

TABLES 11 and 12 present a summary of results for 4% s-equol (w/v) in vehicle. A standard volume-dependent dose-response study was performed with the Ocular Irritection test method. The following volumes of neat sample were applied for analysis: 25, 50, 75, 100 and 125 µl. The results of the study indicated that the sample of S-equol was classified as a mild ocular irritant with an IDE score of 16.4. A similar volume-dependent dose-response study was performed with the Dermal Irritection test method. The results demonstrated that the sample was predicted to be a non-irritant with a HIE score of 0.15. The raw test materials: ethanol vehicle, equol-racemic and S-equol were analyzed in the Ocular and Dermal Irritection tests at 4 percent. Since the vehicle results displayed similar values to that of the equol results (racemic equol or S-equol), this demonstrated that most of the irritant effects seen in the equol samples can be attributed to the vehicle. Therefore, for ocular and dermal applications, racemic equol and S-equol are classified as non-irritating based upon the results for skin/cosmetic relevance.

TABLE 11

Ocular Irritection Results for 4% s-equol

| IVI Number | Sample Description | Dose | IDE Score | Predicted Ocular Irritancy Classification |
|---|---|---|---|---|
| E7186 | S-EQUOL | 25 µl | 12.9 | Minimal/Mild Irritant |
| | | 50 µl | 13.5 | Minimal/Mild Irritant |
| | | 75 µl | 14.2 | Mild Irritant |
| | | 100 µl | 14.7 | Mild Irritant |
| | | 125 µl | 16.4[a] | Mild Irritant |

[a]Maximum Qualified Score

TABLE 12

Dermal Irritection Results for 4% s-equol

| IVI Number | Sample Description | Dose | HIE Score | Predicted Dermal Irritancy Classification |
|---|---|---|---|---|
| S4245 | S-EQUOL | 25 µl | 0.06 | Non-Irritant |
| | | 50 µl | 0.08 | Non-Irritant |

TABLE 12-continued

Dermal Irritection Results for 4% s-equol

| IVI Number | Sample Description | Dose | HIE Score | Predicted Dermal Irritancy Classification |
|---|---|---|---|---|
| | | 75 μl | 0.11 | Non-Irritant |
| | | 100 μl | 0.13 | Non-Irritant |
| | | 125 μl | 0.15[a] | Non-Irritant |

[a]Maximum Qualified Score

The in vivo and in vitro examples presented herein demonstrate that equol has the ability to bind 5α-DHT and biologically inactivate its hormonal influence in skin, hair and prostate, and to stimulate skin cells to proliferate and produce collagen type I, collagen type III and elastin protein expression, all of which contribute to improved skin/hair health and treatment applications of androgen-dependent diseases/disorders of the skin/hair.

Example 14

In vitro Binding of Equol (Isomer Ratio) Directly to 5α-DHT

Samples: In a 20 ml amber glass vial, approximately 4,000 to 5,000 dpm of $^{14}$C-Dihydrotestosterone (DHT; Dupont/NEN, Boston, Mass., USA) was added. Additionally, 3.0 nM (or approximately 865 pg/ml) of cold DHT (Sigma Chemical Co., St. Louis, Mo., USA) was added (in all experiments) and where appropriate varying concentrations of equol (70% R-equol and 30% S-equol mixture) (0 to 2,000 nM; LC Labs., Woburn, Mass., USA or Robert Handa Laboratory, Colorado State University, USA) from ethanol stock solutions. This mixture was vortexed for 30 seconds at room temperature. It was then dried down and subsequently 1 ml of TEGMD (10 mM Tris CL, 1.5 mM EDTA, 10% glycerol, 25 mM molybdate and 1 mM dithrothreitol) buffer was added (capped and mixed by inverting vial 3-times). This mixture was incubated at room temperature for 20-24 hours before placing on the Sephadex column.

Columns: Sephadex LH-20 (25-100 μm particle diameter) from Sigma Chemical Co. (St. Louis, Mo., USA), was used to prepare 1.3 cm×25 cm columns, as described by Lund et al (T D Lund et al., *Biol. Reprod.*, 70: 1188-1195, 2004). Sephadex (0.25 grams) was mixed with 1.5 ml of TEGMD buffer. The serological pipette was plugged with a glass bead and 1 ml of Sephadex was loaded onto the column with TEGMD buffer and equilibrated. Flow rates under gravity were approximately 0.5 ml/min and 0.5 ml fractions were collected in plastic scintillation vials.

Five ml of Ultima Gold scintillation fluid (Packard Instr. Co., Meriden, Conn., USA) was added to each vial, mix thoroughly and counted for 5 min. in a Beckmann LS 6500 scintillation counter. The peak $^{14}$C-DHT fraction and profile using 0 nM of equol was used as reference. The shift (advancement) in peak/profile in subsequent experiments using increasing concentrations of equol (70% R-isomer and 30% S-isomer in this experiment) was calculated based upon this reference (as arbitrary binding units as a percentage of the original reference, n=6 for 0 nM of Equol). Note: data not shown, 2,000 nM of Equol was tested in this experiment which yielded 100.0%±0.3 (s.e.m.) binding, n=3.

Figure 30:
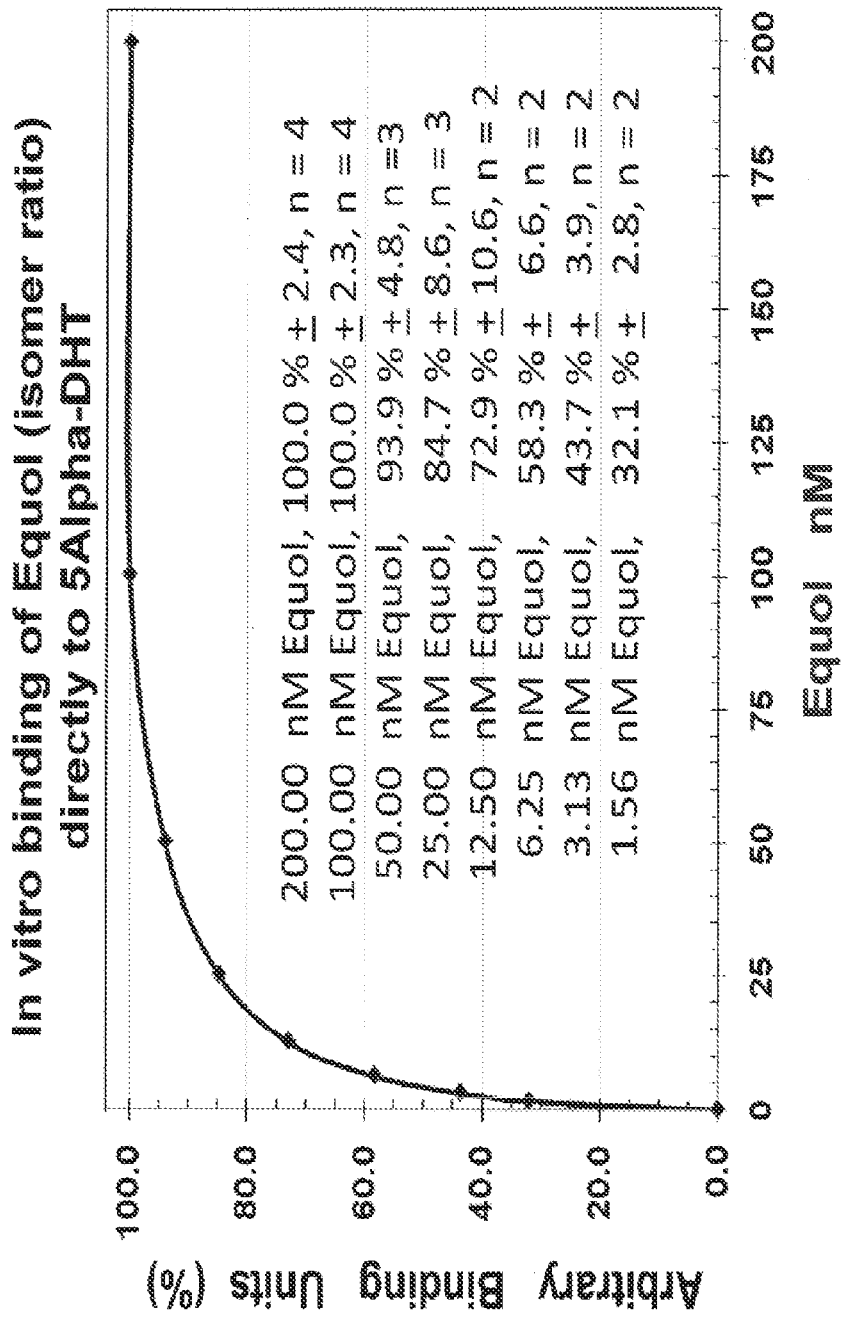
FIG. 30 is a graph showing direct binding (mean±s.e.m.) of an equol isomer ratio to 5α-DHT.

FIG. 30 shows direct binding (mean±s.e.m.) of an equol isomer ratio to 5α-DHT, suggesting important dermal applications for preventing and treating skin disorders and chronological and intrinsic aging.

Example 15

In vitro Blockage of Estrogen Receptor Subtypes by Tamoxifen Demonstrating the Positive Influence of Equol in Stimulating Collagen For the production of organotypic, three-dimensional (3D) cultures, dermal fibroblasts were seeded to nylon mesh and allowed to grow for approximately 8 weeks as described (see Fleischmajer R et al., *J Invest. Dermatol.*, 97:638-643, 1991 and Contrard P et al., *Cell Tissue Res.*, 273:571-575, 1993). This in vitro model closely mimics the development of the dermis, offering a system for study with organotypic properties, such as the ability to support epidermal differentiation (Slivka S et al., *J Invest. Dermatol.*, 100:40-46, 1993) and collagen fibrillogenesis (Contrard P et al., *Cell Tissue Res.*, 273:571-575, 1993). After 2 weeks all 3D cultures were supplemented with 20 μg/ml ascorbate.

To examine the effects of estrogen receptor subtypes by which equol enhancement of collagen synthesis occurred, cultures were grown in phenol red-free medium for at least 2 weeks prior to the addition of the test materials to produce an environment with extremely low levels of estrogenic activity. The estrogen receptor subtype blocker, tamoxifen (Tocris Inc., Cat.# 0999 batch #A/57889) was added approximately 16 hours before the addition of either equol or 17β-estradiol. The cultures were incubated for 4 additional days without feeding, and were then processed for intracellular FACS.

Figure 31:
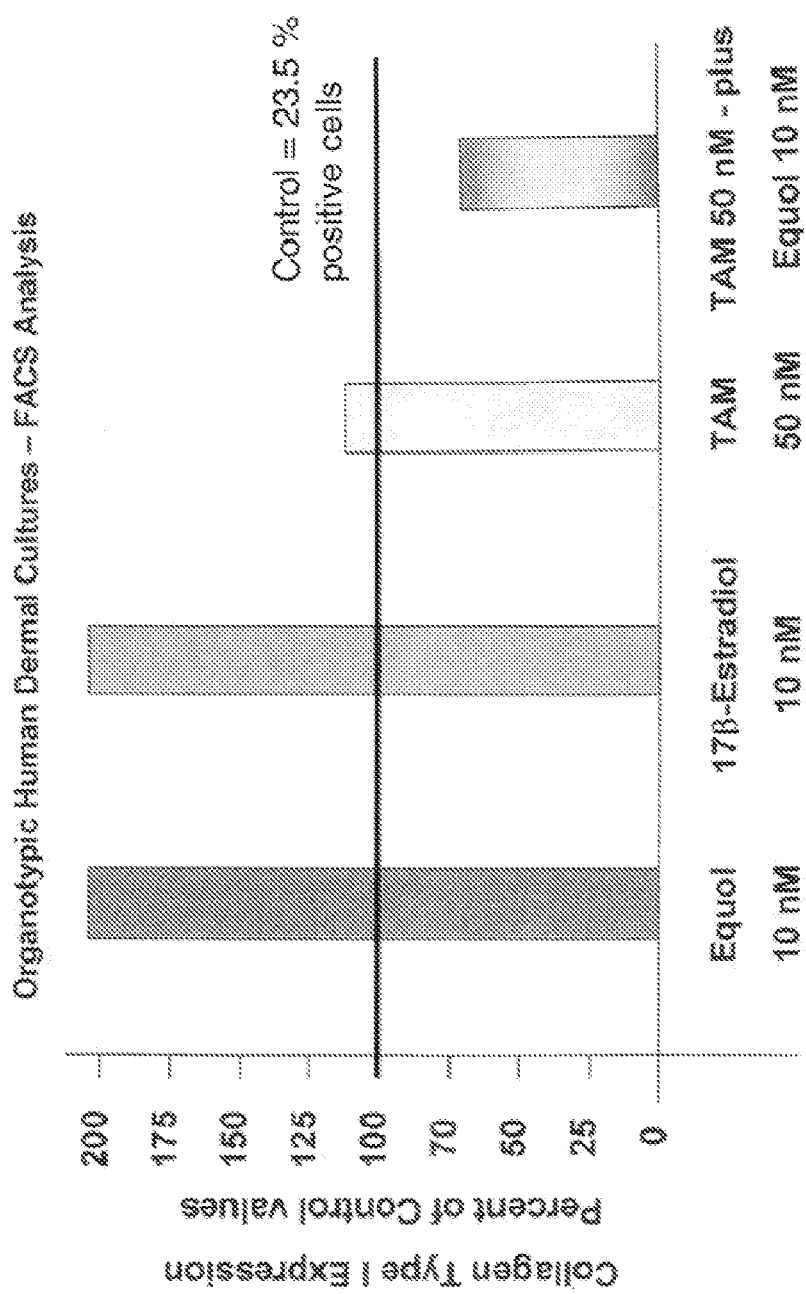
FIG. 31 is a graph illustrating the blockade of equol's positive effects on collagen type I production by estrogen receptor subtype blocker, tamoxifen (TAM) in human dermal organotypic cultures.

As shown in FIG. 31, the vehicle control or positive cells displayed collagen type I expression at 23.5% and this was set at 100% which is represented by the horizontal line in the figure. Both non-racemic equol and 17β-estradiol at 10 nM stimulated collagen expression by over 200%, while TAM alone at 50 nM was not different compared to control values. However, when TAM was added to the cultures before the addition of non-racemic equol, it significantly blocked the estrogen receptor subtypes which prevented the stimulation of collagen. In fact, the TAM plus equol treatment represented a 65% decrease compared to equol alone. This provided direct evidence that equol's positive stimulation of collagen type I can be blocked by a known estrogen receptor subtype blocker tamoxifen and these actions were mediated in the epidermis and dermal regions where estrogen receptor subtypes are abundant (See Thornton M J et al., *Exp. Dermatol.*, 12:181-190, 2003 and Thornton M J et al., *J Invest. Dermatol. Symp. Proc.*, 8:100-103, 2003).

Example 16

In vitro Blockage by Tamoxifen Demonstrating the Positive Influence of Equol in Stimulating Collagen Type I, Collagen Type III and Elastin Via Estrogen Receptor Subtypes Using an organotypic three-dimensional dermal model, which closely resembles the intact dermis and allows for tissue deposition and maturation of the extracellular matrix (ECM) by fibroblasts, collagen type I, collagen type III and elastin deposition was examined by intracellular FACS analysis as described above.

The anti-estrogen receptor blocker, tamoxifen (TAM) was added approximately 16 hours before the addition of non-racemic equol. Cultures were incubated for 4 days in the presence of the test molecules without feeding, and were then processed for intracellular FACS analysis. In this study parallel studies were performed (n=3) and the data (mean±s.e.m.) is shown in the FIG. 33. There were no significant differences in MTT values among the treatment groups (data not shown).

Figure 32:
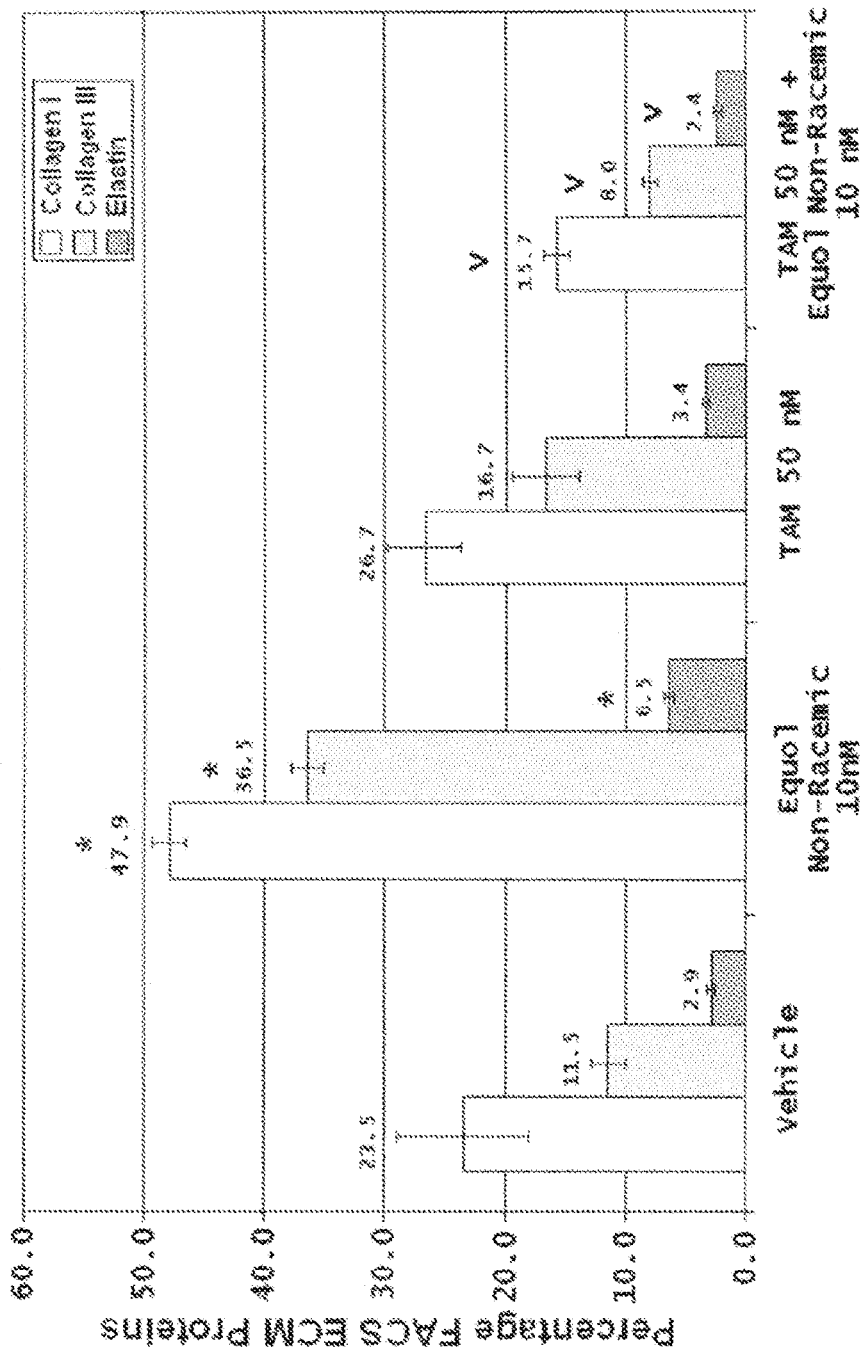
FIG. 32 is a graph illustrating the blockade of equol's positive effects on collagen type I and type III and elastin by estrogen receptor subtype blocker, TAX in human dermal-equivalent cultures.

As shown in FIG. 32, 10 nM of non-racemic equol stimulated collagen type I by over 2-fold; collagen type III by over 3-fold and elastin by over 2.2-fold (see * symbols) compared to vehicle values for these extracellular matrix (ECM) proteins. Tamoxifen alone at 50 nM did not yield significantly different results compared to control vehicle values. However, when tamoxifen and equol were combined all stimulatory effects of non-racemic equol on collagen type I, collagen type III and elastin were blocked (see v symbols; at or below control vehicle levels), demonstrating that equol acts via estrogen receptor subtypes in the skin.

Example 17

Dosing with Different Concentrations of Non-Racemic Equol In Vitro: Determination of Viability and Cytotoxicity in Organotypic Human Full-Thickness Equivalents This study utilized organotypic human full-thickness equivalents (Organogenesis, TestSkin II, Cat. # TS02-001). The skin cultures support normal differentiation of epidermal and dermal cells and components of the extra-cellular matrix. Biopsies from the cultures were obtained after the test materials were exposed to the organotypic human full-thickness equivalents for approximately 72 hours.

Cytotoxicity was determined by spectrophotometric detection of reduced 3-(4,5-dimethylthiazol-2-yl-2,5-phenyltetrazolium bromide (MTT) at 550 nM as previously described herein. After the MTT solution was removed, the biopsies were washed twice in PBS, then 2.0 ml per biopsy of a 0.6 mg/ml solution of thermolysin (Sigma Cat. #T7902) was added. This enzyme can separate the dermis from the epidermis. Additionally, biopsies were chosen for histological evaluation by trichrome staining. Single biopsies were fixed in 10% formalin at 4° C., prior to embedding and sectioning at 3 microns. Trichrome staining is a standard histological stain, which selectively binds collagen and yields a blue-green reaction product which can be observed and quantified microscopically. All histology processing and staining was performed according to standard clinical protocols. The abundance of the observed collagen was standardized by the quantified MTT levels which yielded cell viability and/or cytotoxicity as shown in FIG. 33.

Figure 33:
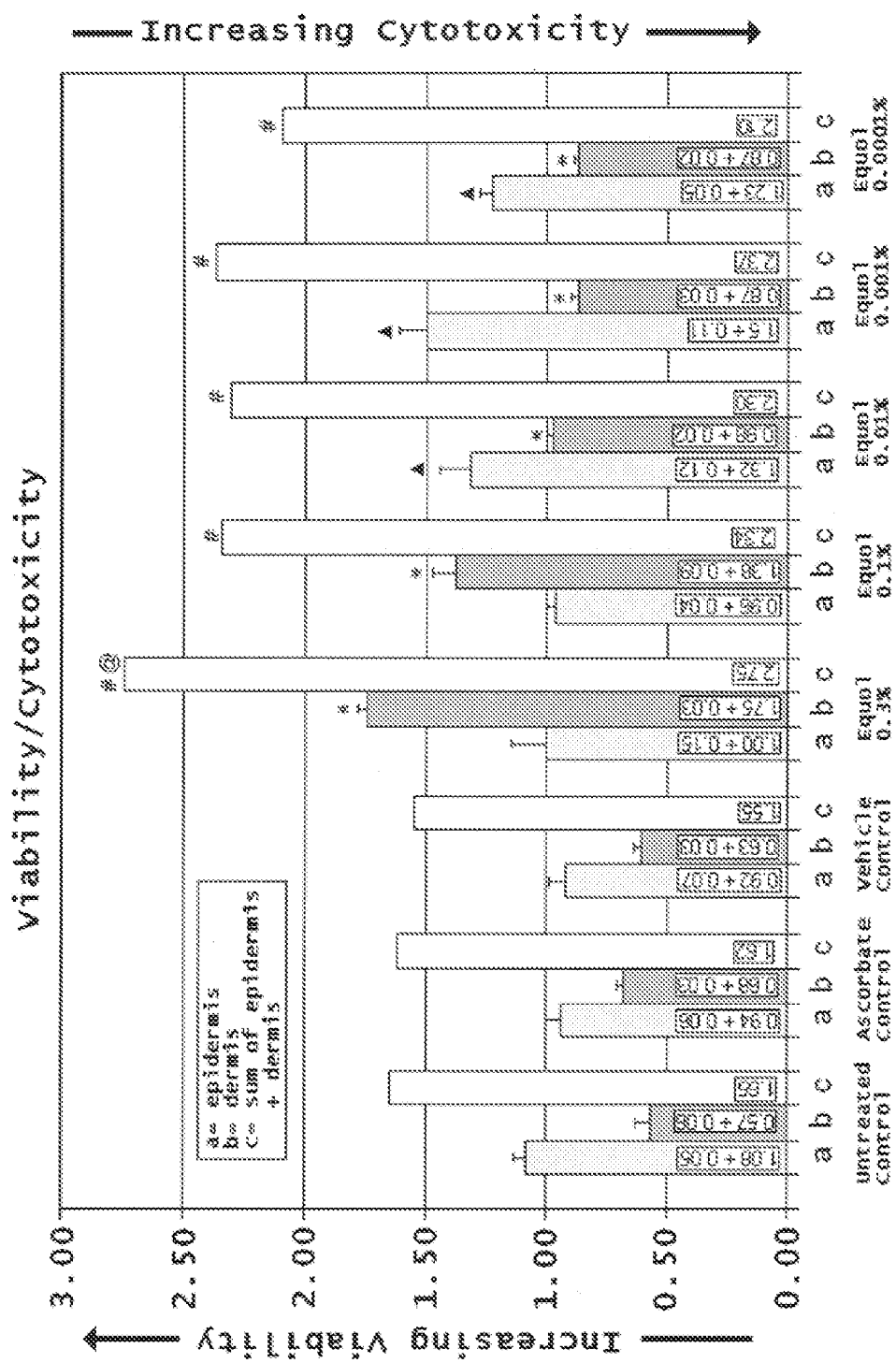
FIG. 33 is a graph displaying dosing with different concentrations of non-racemic equol (0.3 to 0.0001%) in vitro to determine viability and cytotoxicity in organotypic human full-thickness equivalents.

As shown in FIG. 33, the cytotoxicity among the control treatments was not significantly different for the epidermal, dermal or sum of the epidermal and dermal components. However, the non-racemic equol treatment at 0.3% yielded the most optimal concentration where the dermal viability was significantly increased compared to vehicle control values due most likely to an increased renewal of fibroblasts, as report previously herein. Moreover, non-racemic equol concentrations at 0.1, 0.01, 0.001 and 0.0001 percent also displayed significantly higher dermal viability levels compared to controls (see asterisk symbol). In the epidermal component, non-racemic equol concentrations at 0.01, 0.001 and 0.0001 percent showed significantly higher viability levels compared to vehicle control values (see triangle symbol). When the epidermal and dermal values were summed together all equol concentrations from 0.3 to 0.0001% displayed significantly higher values for viability compared to controls (see # symbol). Finally, the equol 0.3% concentration displayed the highest level of viability which was significantly greater than all other equol concentrations tested in addition to control values (see @ symbol). These data suggested that non-racemic equol at very low concentrations can have an important and novel impact on skin health.

Example 18

Figure 34:
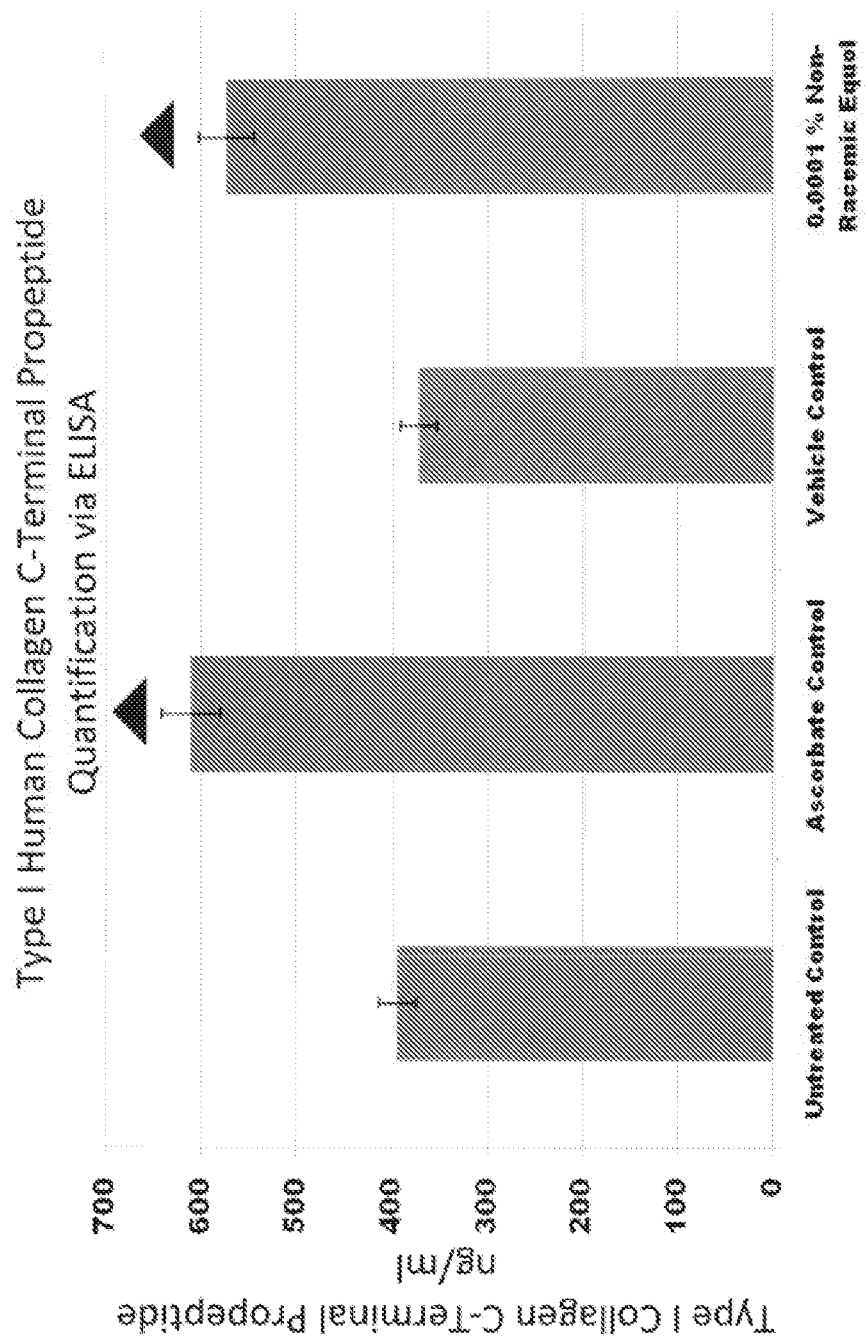
FIG. 34 is a graph showing stimulation of collagen in human dermal fibroblasts using a known tissue penetrating agent with non-racemic equol.

Dosing with 0.0001% Non-Racemic Equol Significantly Increases Type I Collagen C-Terminal Propeptide in Human Monolayer Fibroblasts Human dermal fibroblasts were cultured and the test molecules were exposed to the cells for approximately 48 hours. There were no significant differences in MTT values among the molecules tested and the ability of the dermal fibroblast to synthesis type I collagen was quantified by ELISA for human type I collagen C-terminal propeptide as shown in FIG. 34. This study was performed in the presence of a known tissue penetrating agent used in cosmetics to determine the effectiveness of low concentrations of non-racemic equol in stimulating collagen type I.

As shown in FIG. 34, ascorbate served as the positive control; non-racemic equol at 0.0001% (w/v) significantly stimulated type I collagen (see triangle symbols) over untreated- and vehicle-control values. This shows that using a known tissue penetrating agent with a very low dose of non-racemic equol can significantly stimulate the production of human collagen in fibroblasts.

Example 19

Non-Racemic Equol Outperforms S-Equol in Stimulating Collagen Deposition in Human Dermal Fibroblasts Human dermal fibroblasts were cultured and the test molecules were exposed to the cells for approximately 48 hours, as described herein.

Figure 35:
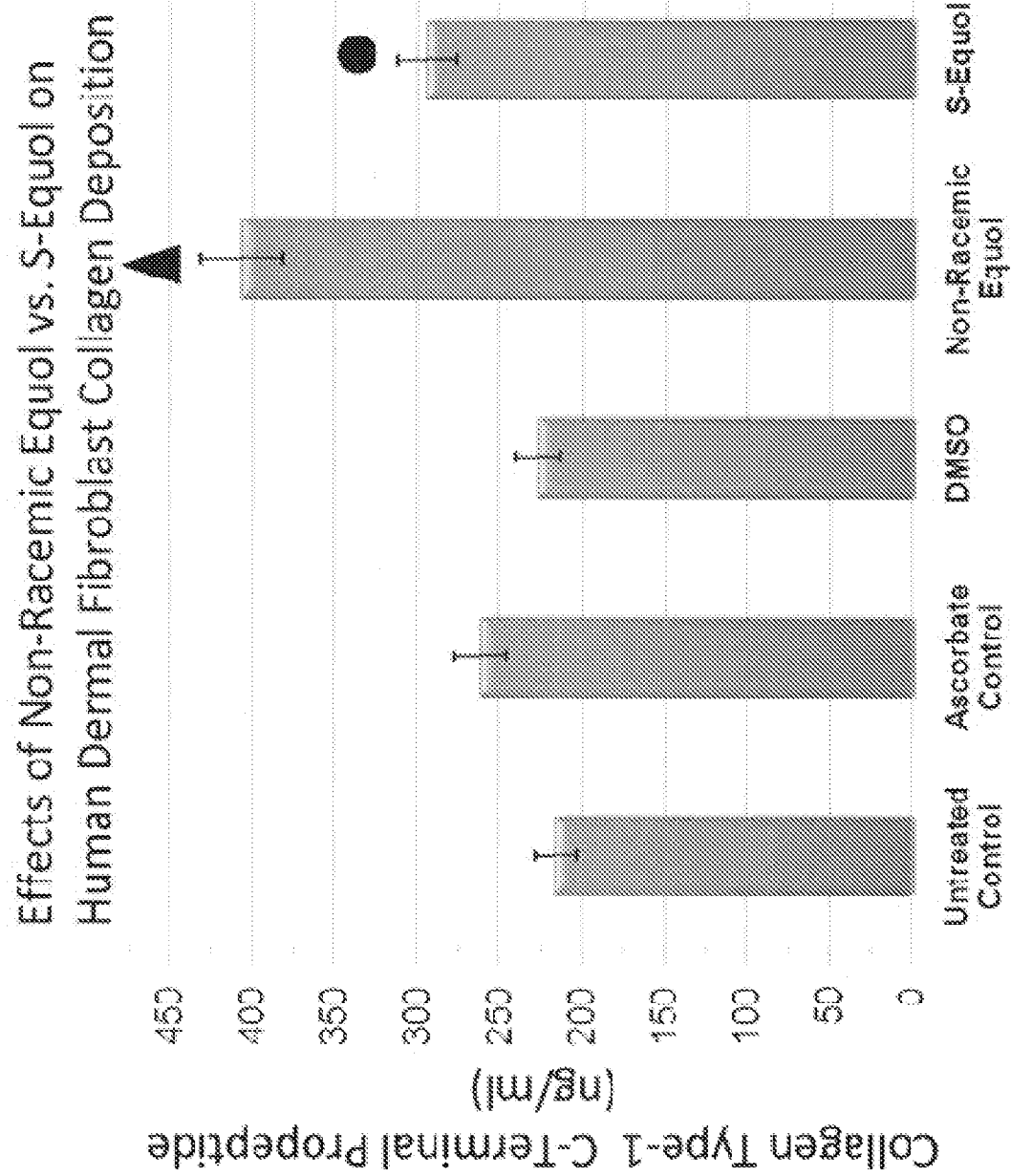
FIG. 35 is a graph showing non-racemic equol effects on stimulating collagen deposition in human dermal fibroblasts.

There were no significant differences in MTT values among the molecules tested and the ability of the dermal fibroblast to synthesis type I collagen was quantified by ELISA for human type I collagen C-terminal propeptide as shown in FIG. 35. This study was performed using dimethylsulfoxide (DMSO) as the vehicle and ascorbate served as the positive control.

As shown in FIG. 35, non-racemic equol at 10 nM outperformed 100% S-equol in significantly stimulating collagen in human monolayer fibroblasts (see triangle symbol) and increased collagen deposition over DMSO control levels by approximately 1.6-fold. Pure S-equol at 10 nM significantly increased collagen levels over DMSO control values (solid circle). However the non-racemic equol treatment represented an improved 40% increase in collagen deposition over the S-equol treatment, suggesting that each isomer of equol has distinct or intrinsic chemical/biological properties which yield different results based upon the combination of equol isomer ratios employed. The potential of using different ratio mixtures of equol isomers represents broad applications for skin and hair health.

Example 20

Human Pilot Study

In Men and Women, Serum 5α-DHT Levels Before and after Treatment with Non-Racemic Equol In a pilot study involving 4 men (ages 50 to 59 years old) and 2 postmenopausal women (ages 60 to 62), baseline levels of serum 5α-dihydrotestosterone (5α-DHT) were determined by ELISA in triplicate. After 7 days of oral dosing with 3 mg of non-racemic equol per day, 5α-DHT levels were again determined.

TABLE 13

| MEN | Baseline: 5α-DHT levels before the 1st morning dose on the 7th day of treatment | 5α-DHT levels on day 7 of oral dosing (two to four hours after the 1st morning dose) |
|---|---|---|
| Subject A | 692 + 10 pg/ml | 600 + 13 pg/ml* |
| Subject B | 724 + 18 pg/ml | 612 + 18 pg/ml* |
| Subject C | 658 + 23 pg/ml | 534 + 16 pg/ml* |
| Subject D | 747 + 27 pg/ml | 596 + 28 pg/ml* |

*= significant decrease compared to baseline values

TABLE 14

| WOMEN | Baseline: 5α-DHT levels before the 1st morning dose on the 7th day of treatment | 5α-DHT levels on day 7 of oral dosing (two to four hours after the 1st morning dose) |
|---|---|---|
| Subject E | 221 + 5 pg/ml | 170 + 6 pg/ml* |
| Subject F | 265 + 14 pg/ml | 193 + 20 pg/ml* |

*= significant decrease compared to baseline values

This studies demonstrated that oral consumption of equol significantly decreased serum 5α-DHT levels in men (by approximately 17%) and in women (by approximately 26%) that provided androgen hormone modulation in dermal applications for preventing and treating skin disorders and chronological and intrinsic aging.

Example 21

Photo-Analysis of Dosing with Non-Racemic Equol at 0.3% in a Half-Face Experiment over 7 Weeks Non-racemic equol at 0.3% was prepared in a known skin tissue penetrating agent and applied twice per day (approximately 0.5 grams per application) for a total of 7 weeks (see FIG. 36) to the right-side of the face (only) of a man approximately 50 years old.

Figure 36:
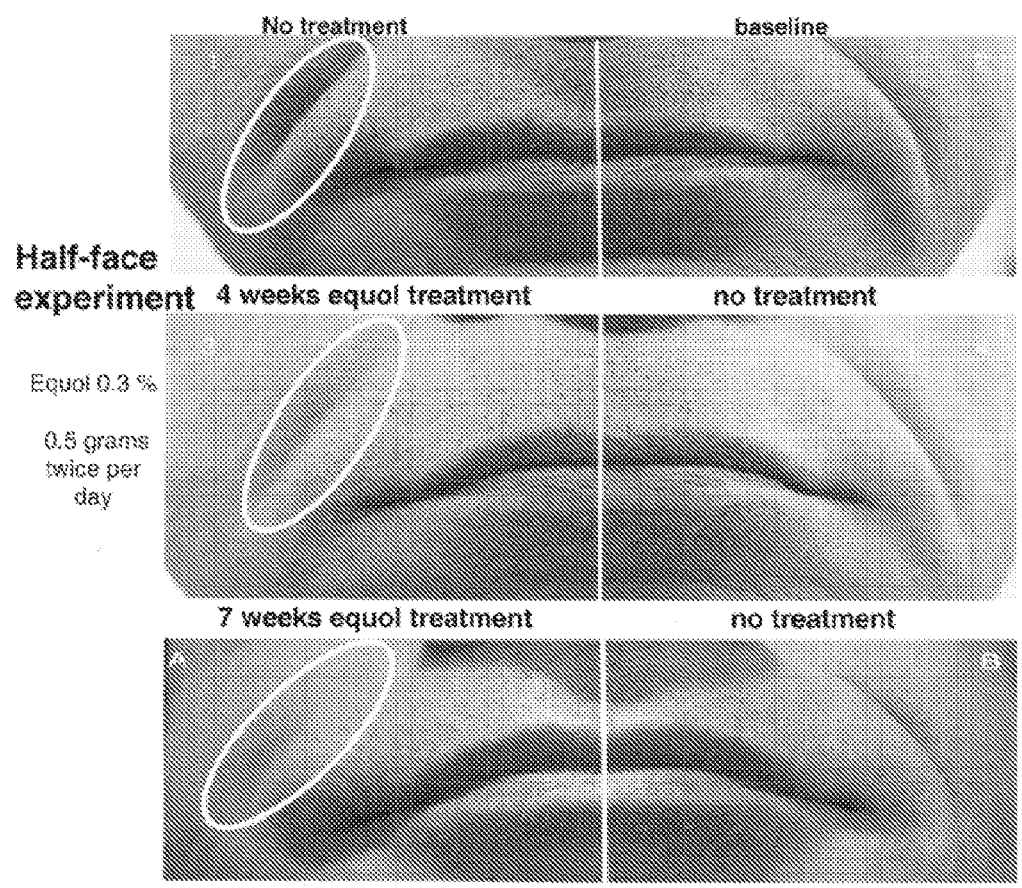
FIG. 36 is a photograph of a photo-analysis by dosing with non-racemic equol in a half-face experiment.

As shown in FIG. 36, the upper panel (1 and 2) displays the no treatment or baseline condition for both sides of the face of the man. After 4 weeks of the equol treatment on the right-side only depicting the nasolabial fold outlined by the white sphere (3) showed dramatic improvement of lines and wrinkles. After 7 weeks on the equol treatment (the right-side only) outlined by the white sphere (A) showed further remarkable improvement in skin tone, texture and significant reduction in the skin (nasolabial) fold and fine lines. This data showed impressive improvement of skin components, which underline the positive influences of equol on epidermal and dermal parameters along with striking changes in the extracellular matrix such as collagen, elastin and matrix metalloproteinases, etc. in regulating skin texture and health.

While various embodiments of the present invention have been described in detail, it will be apparent that further modifications and adaptations of the invention will occur to those skilled in the art. It is to be expressly understood that such modifications and adaptations are within the spirit and scope of the present invention.

The invention claimed is:

1. A method of mediating androgen hormone action so as to ameliorate at least one condition of the skin or hair of a subject, comprising
administering a non-racemic mixture of R- and S-equol, wherein R-equol binds free 5α-dihydrotestosterone and inhibits its binding with androgen receptor, and
wherein at the least one condition of the skin and hair is selected from the group consisting of:
a) inducing increased skin integrity by cell renewal;
b) enhancing water content or moisture of skin;
c) enhancing glycoaminoglycans and hyaluronic acid for improved skin radiance;
d) reducing trans epidermal water loss, skin flaking and scaling;
e) invigorating for energetically healthy skin;
f) improving skin thickness and enhanced cellular durability;
g) strengthening skin collagen and improving skin health;
h) enhancing skin tensile properties and improving the protective nature of the skin;
i) increasing elastin production and improving skin elasticity;
j) protecting against and inhibiting elastase;
k) protecting against and inhibiting collagenase;
l) protecting against and decreasing matrix metalloproteinases;
m) improving skin texture and tone;
n) reducing skin pores size and enhancing skin smoothness;
o) rejuvenating and renewing skin;
p) improving the appearance of scars and skin abrasions and enhancing skin repair and wound healing;
q) decreasing oily skin by minimizing sebaceous gland secretion and improving sebaceous gland function;
r) enhancing hair pigmentation;
s) increasing blood flow in the skin;
t) improving skin temperature and thermoregulation of the skin;
u) inhibiting fibroblast cell apoptosis;
v) stabilizing skin color changes and hair pigmentation and enhancing skin lightening;
w) treating, ameliorating and protecting against hyperpigmentation, age-spots and photo-aging;
x) decreasing or eliminating acne;
y) decreasing scalp hair loss or enhancing the retention of scalp hair (in male and female pattern baldness);
z) retarding facial and body hair growth, decreasing facial and body hair growth, and reducing hirsutism;
aa) reducing vaginal dryness; and
bb) attenuating skin and hair abnormalities in steroid hormone synthesis and function and metabolism of steroids and binding steroid receptors involving androgenic and/or estrogenic effects.

2. The method of claim 1, wherein the non-racemic mixture of R- and S-equol comprises at least 5% of R-equol.

3. The method of claim 1, wherein the non-racemic mixture of R- and S-equol comprises at least 10% of R-equol.

4. The method of claim 1, wherein the non-racemic mixture of R- and S-equol comprises at least 20% of R-equol.

5. The method of claim 1, wherein the non-racemic mixture of R- and S-equol comprises at least 25% of R-equol.

6. The method of claim 1, wherein the non-racemic mixture of R- and S-equol comprises S-equol in an amount sufficient to bind estrogen receptor subtypes.

7. A method of ameliorating at least one condition of the skin or hair of a subject, comprising:
administering a composition comprising a non-racemic mixture of R- and S-equol, wherein R-equol binds free 5α-dihydrotestosterone and inhibits its binding with androgen receptors
wherein at the least one condition of the skin and hair is selected from the group consisting of:
a) inducing increased skin integrity by cell renewal;
b) enhancing water content or moisture of skin;

c) enhancing glycoaminoglycans and hyaluronic acid for improved skin radiance;
d) reducing trans epidermal water loss, skin flaking and scaling;
e) invigorating for energetically healthy skin;
f) improving skin thickness and enhanced cellular durability;
g) strengthening skin collagen and improving skin health;
h) enhancing skin tensile properties and improving the protective nature of the skin;
i) increasing elastin production and improving skin elasticity;
j) protecting against and inhibiting elastase;
k) protecting against and inhibiting collagenase;
l) protecting against and decreasing matrix metalloproteinases;
m) improving skin texture and tone;
n) reducing skin pores size and enhancing skin smoothness;
o) rejuvenating and renewing skin;
p) improving the appearance of scars and skin abrasions and enhancing skin repair and wound healing;
q) decreasing oily skin by minimizing sebaceous gland secretion and improving sebaceous gland function;
r) enhancing hair pigmentation;
s) increasing blood flow in the skin;
t) improving skin temperature and thermoregulation of the skin;
u) inhibiting fibroblast cell apoptosis;
v) stabilizing skin color changes and hair pigmentation and enhancing skin lightening;
w) treating, ameliorating and protecting against hyperpigmentation, age-spots and photo-aging;
x) decreasing or eliminating acne;
y) decreasing scalp hair loss or enhancing the retention of scalp hair (in male and female pattern baldness);
z) retarding facial and body hair growth, decreasing facial and body hair growth, and reducing hirsutism;
aa) reducing vaginal dryness; and
bb) attenuating skin and hair abnormalities in steroid hormone synthesis and function and metabolism of steroids and binding steroid receptors involving androgenic and/or estrogenic effects.

8. The method of claim 7, wherein the non-racemic mixture of R- and S-equol comprises at least 5% of R-equol.

9. The method of claim 7, wherein the non-racemic mixture of R- and S-equol comprises at least 10% of R-equol.

10. The method of claim 7, wherein the non-racemic mixture of R- and S-equol comprises at least 20% of R-equol.

11. The method of claim 7, wherein the non-racemic mixture of R- and S-equol comprises at least 25% of R-equol.

12. The method of claim 7, wherein the composition is administered topically, transdermally, or subdermally.

13. The method of claim 7, wherein the composition is a topical composition comprising from at least about 0.001% to about 10% equol.

14. The method of claim 7, wherein the composition further comprises a pharmaceutical active or an excipient.

15. The method of claim 7, wherein the composition is administered orally at a dose of at least about 0.005 mg of equol per kg body weight.

16. The method of claim 7, wherein the composition is in a delayed or a sustained release formulation.

17. The method of claim 7, wherein the composition is administered via a lotion, a spray solution, a pad, a bandage, or a transdermal patch.

18. The method of claim 7, wherein the non-racemic mixture of R- and S-equol comprises S-equol in an amount sufficient to bind estrogen receptor subtypes.

* * * * *